United States Patent
Nordstrom

(10) Patent No.: US 11,883,097 B2
(45) Date of Patent: Jan. 30, 2024

(54) METHOD AND APPARATUS FOR TESTING FOR COLOR VISION LOSS

(71) Applicant: Innova Systems, Inc., Burr Ridge, IL (US)

(72) Inventor: Cheryl Nordstrom, Hinsdale, IL (US)

(73) Assignee: Innova Systems, Inc., Burr Ridge, IL (US)

(*) Notice: Subject to any disclaimer, the term of this patent is extended or adjusted under 35 U.S.C. 154(b) by 755 days.

(21) Appl. No.: 17/068,417

(22) Filed: Oct. 12, 2020

(65) Prior Publication Data

US 2021/0076932 A1    Mar. 18, 2021

Related U.S. Application Data

(63) Continuation-in-part of application No. 15/888,553, filed on Feb. 5, 2018, now Pat. No. 10,799,108, which
(Continued)

(51) Int. Cl.
*A61B 3/06* (2006.01)
*A61B 3/00* (2006.01)
*A61B 3/02* (2006.01)

(52) U.S. Cl.
CPC ............ *A61B 3/066* (2013.01); *A61B 3/0025* (2013.01); *A61B 3/0041* (2013.01); *A61B 3/022* (2013.01)

(58) Field of Classification Search
CPC ..... A61B 3/066; A61B 3/0025; A61B 3/0041; A61B 3/022; A61B 3/12; A61B 3/032;
(Continued)

(56) References Cited

U.S. PATENT DOCUMENTS

| | | | | |
|---|---|---|---|---|
| 6,203,157 | B1 * | 3/2001 | Lee | A61B 3/066 351/242 |
| 6,260,970 | B1 * | 7/2001 | Horn | A61B 3/032 351/246 |
| 2019/0125180 | A1 | 5/2019 | Arnold et al. | |

FOREIGN PATENT DOCUMENTS

WO    WO2019/089963    5/2019

OTHER PUBLICATIONS

Rabin, Jeff, et al. "Rapid Quantification of Color Vision: The Cone Contrast Test," Investigative Ophthalmology & Visual Science; Feb. 2011, vol. 52, No. 2, pp. 816-820.
(Continued)

*Primary Examiner* — Collin X Beatty
(74) *Attorney, Agent, or Firm* — Simpson & Simpson, PLLC

(57) ABSTRACT

A method for administering a cone contrast color vision test includes displaying a first color at a first contrast level in a first region of a display and a second color at a first contrast level in a second region of the display, receiving a first input signal via an input device that indicates whether the patient recognizes the first region, displaying the first color at a second contrast level in a third region of the display and the second color at a second contrast level in a fourth region of the display, receiving a second input signal indicative of whether the patient recognizes the third region, assigning a score related to cone sensitivity of the first color at the first and second contrast levels, storing the score, and comparing the score to a previous score to calculate a progression of a cone sensitivity loss.

20 Claims, 42 Drawing Sheets

Related U.S. Application Data is a continuation-in-part of application No. 14/819,046, filed on Aug. 5, 2015, now Pat. No. 9,883,794, which is a continuation of application No. 14/251,286, filed on Apr. 11, 2014, now abandoned, which is a continuation of application No. 13/887,272, filed on May 3, 2013, now abandoned.

(60) Provisional application No. 61/642,378, filed on May 3, 2012, provisional application No. 61/642,292, filed on May 3, 2012.

(58) Field of Classification Search
CPC .. A61B 3/14; A61B 3/112; A61B 3/06; A61B 3/0008; A61B 3/102; A61B 3/063; A61B 3/0033; A61B 3/0325; A61B 3/024; A61B 3/028; A61B 3/1015; A61B 3/145; A61B 3/10; A61B 3/113; A61B 3/13; A61B 3/0058; A61B 3/02; A61B 3/1025; A61B 5/0075; A61B 2560/0223; A61B 3/00; A61B 3/0091; A61B 3/1225; A61B 3/152; A61B 5/0079; A61B 5/117; A61B 5/4058; A61B 5/6821; A61B 2576/02; A61B 3/0075; A61B 3/15; A61B 5/0033; A61B 5/0082; A61B 2560/0431; A61B 3/0016; A61B 3/103; A61B 3/107; A61B 3/1173; A61B 3/18; A61B 2018/205547; A61B 3/036; A61B 5/161; A61B 8/06; A61B 8/0816; A61B 1/00165; A61B 2562/046; A61B 3/005; A61B 3/0066; A61B 3/085; A61B 3/111; A61B 3/1208; A61B 3/125; A61B 3/158; A61B 5/0084
USPC ....................................................... 351/242
See application file for complete search history.

(56) References Cited

OTHER PUBLICATIONS

Rabin, Jeff. "Quantification of Color Vision with Cone Contrast Sensitivity," Visual Neuroscience, Cambridge University Press, 2004, 21, pp. 483-485.

Rabin, Jeff. "Cone-Specific Measures of Human Color Vision," Visual Sciences Branch, Aircrew Health and Performance Division, US Army Aeromedical Research Laboratory, Fort Rucker, Alabama, Jul. 23, 1996, (Dec. 1996) vol. 37, No. 13, pp. 2771-2774.

http://spyder.datacolor.com/products; Spyder 3tm sold by Datacolor of Lawrenceville, NJ, last accessed Apr. 10, 2017.

"Perception Lecture Notes: Spatial Frequency Channels." (Prof. Michael Landy, https://www.cns.nyu.edu/~david/courses/perception/lecturenotes/channels/channels/html, last accessed Oct. 9, 2020).

* cited by examiner

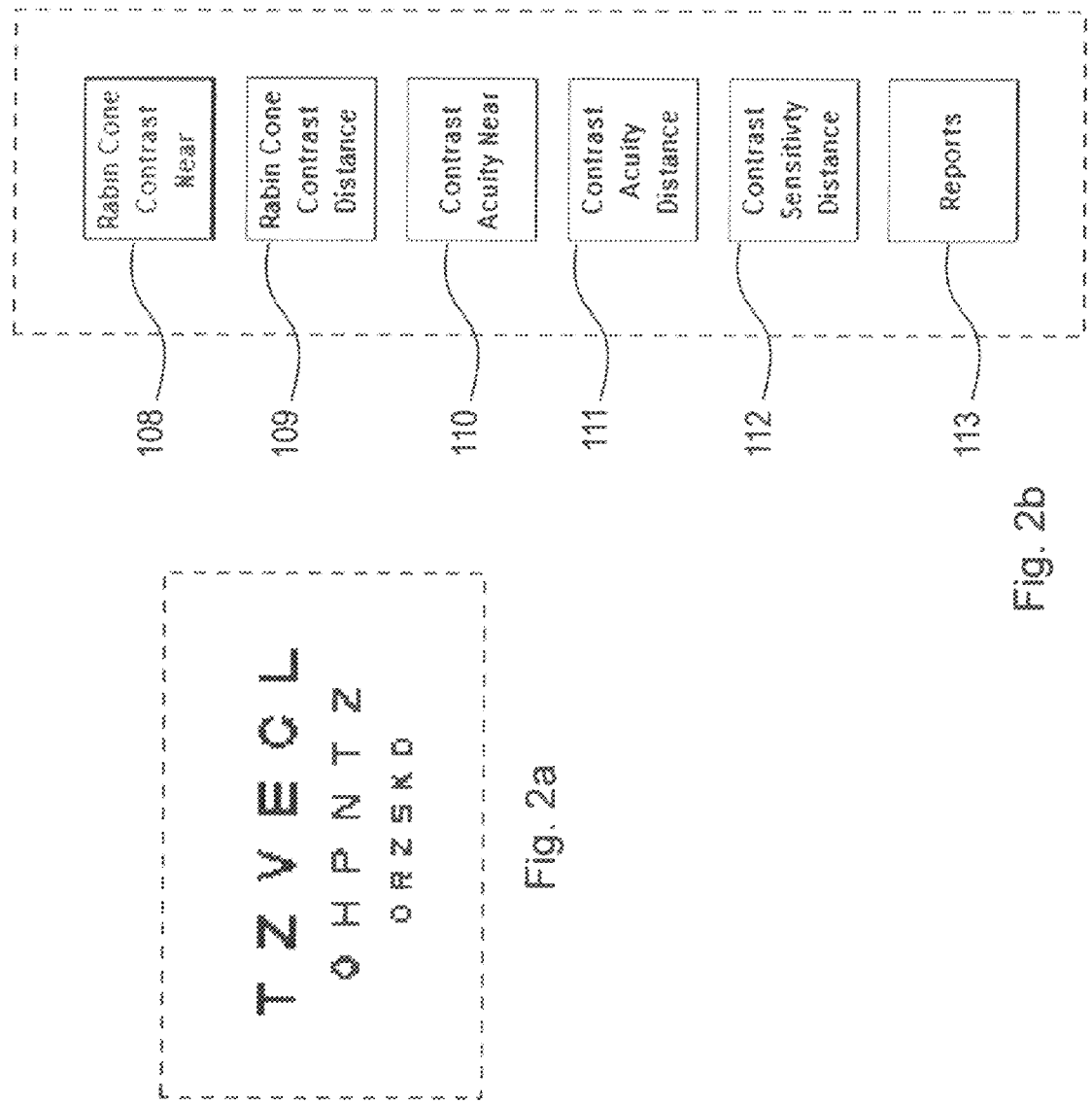

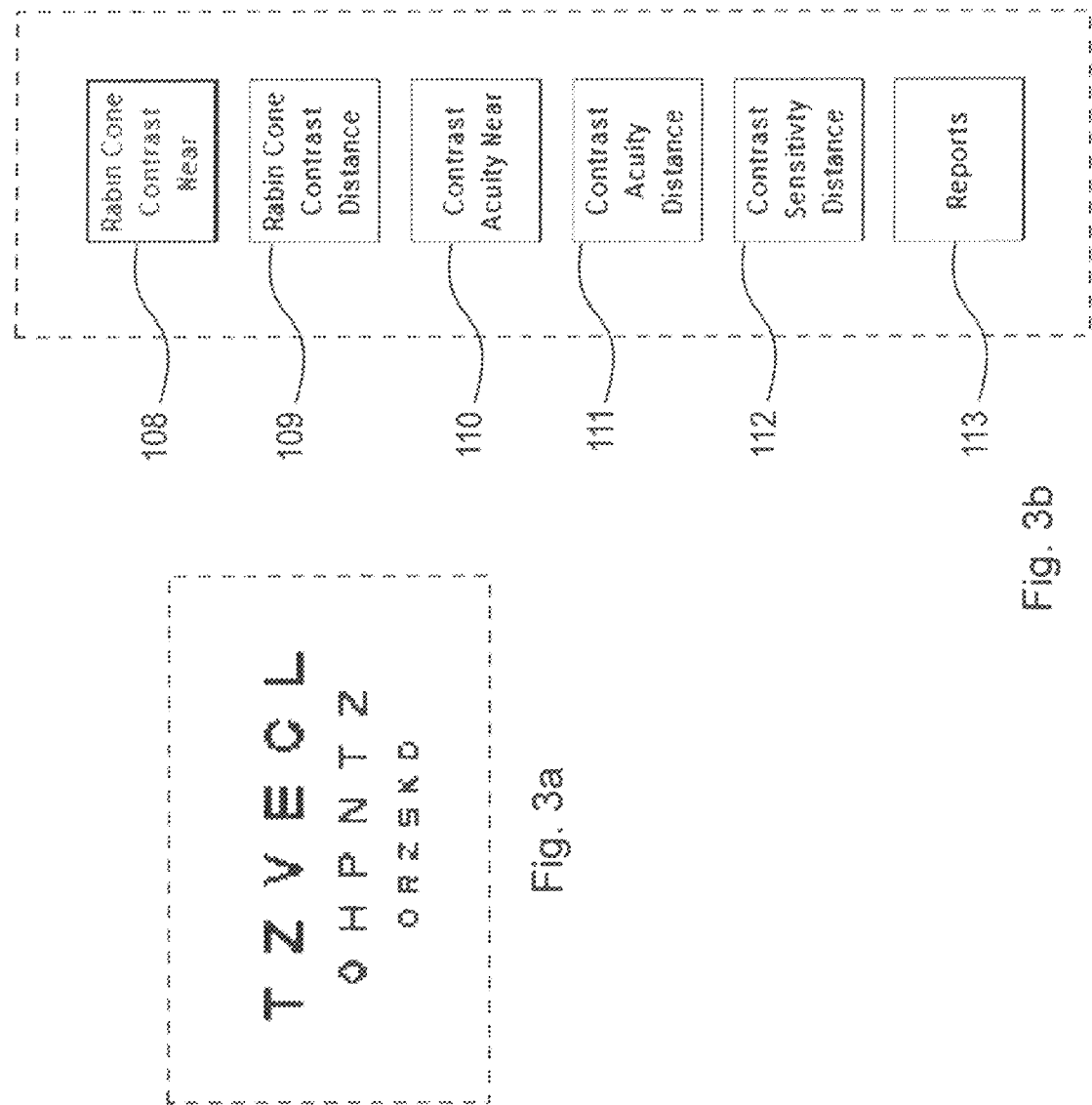

Fig. 20

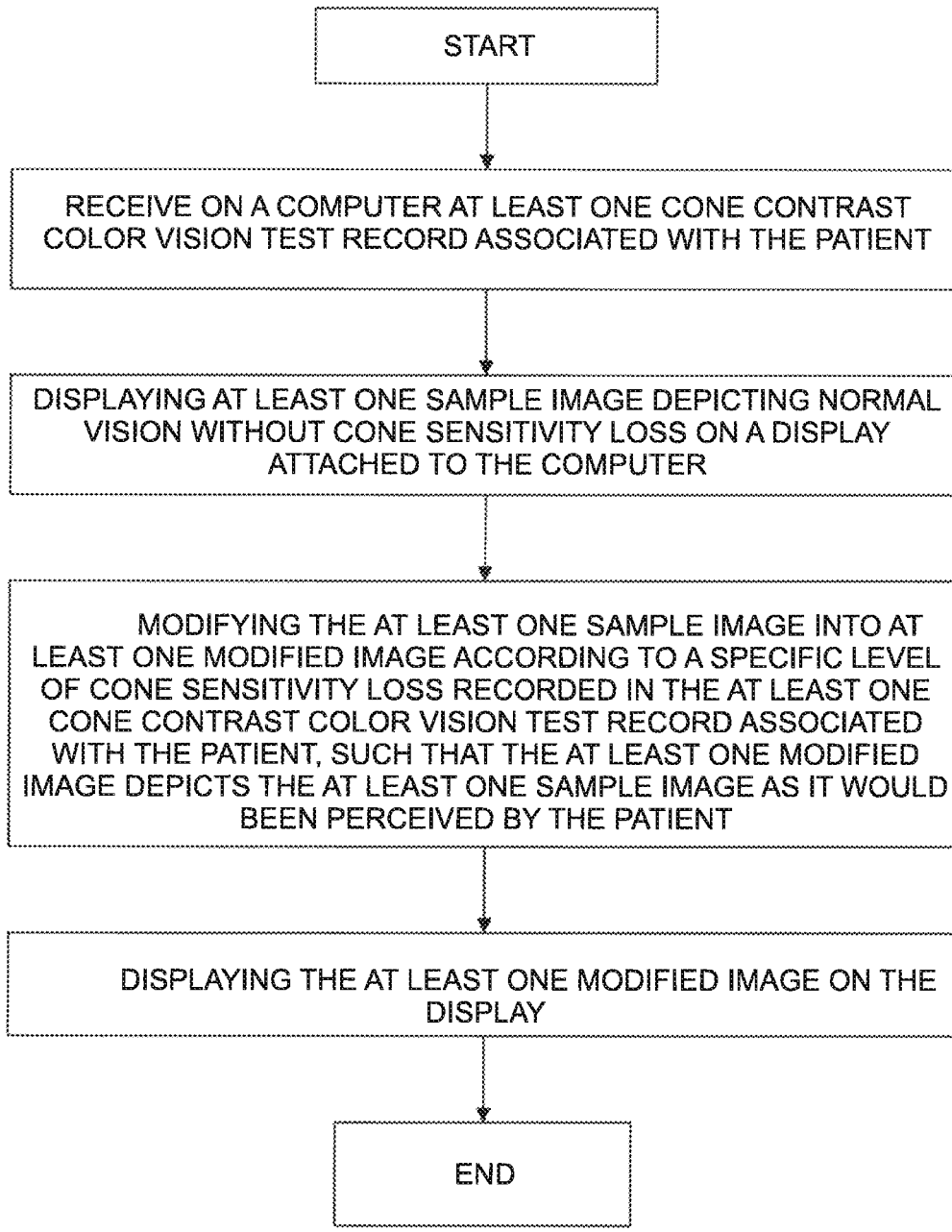
Fig, 25

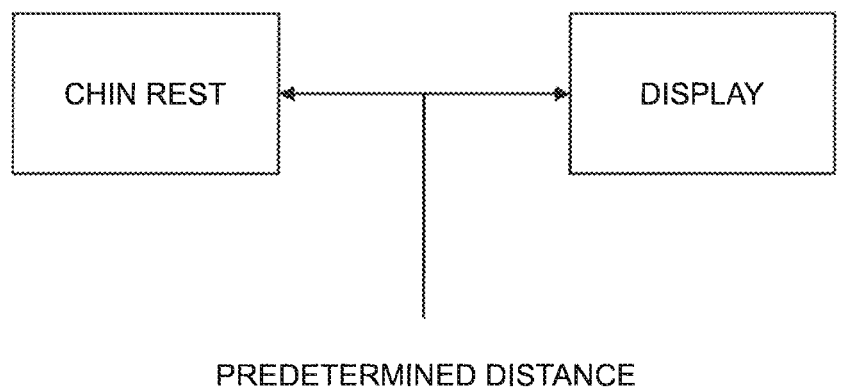
Fig, 26

METHOD AND APPARATUS FOR TESTING FOR COLOR VISION LOSS

CROSS-REFERENCE TO RELATED APPLICATIONS

This application is a continuation-in-part application filed under 35 U.S.C. §§ 111(a) and 120 of U.S. patent application Ser. No. 15/888,553, filed Feb. 5, 2018, which application is a continuation-in-part application of U.S. patent application Ser. No. 14/819,046, filed on Aug. 5, 2015, which application is a continuation of U.S. Nonprovisional patent application Ser. No. 14/251,286, filed Apr. 11, 2014, which is a continuation of U.S. Nonprovisional patent application Ser. No. 13/887,272, filed May 3, 2013, which claims the benefit under 35 U.S.C. § 119(e) of U.S. Provisional Patent Application No. 61/642,378, filed May 3, 2012 and U.S. Provisional Patent Application No. 61/642,292, filed May 3, 2012, each of which applications are incorporated herein by reference in their entireties.

FIELD

The present method and apparatus relate to eye tests for hereditary and acquired color vision loss and may be used for the early detection, progression and treatment monitoring of eye conditions including retinal diseases, glaucoma, neurological diseases, TBI and concussion, as well as retinal toxicity due to high-risk medications. Particularly, the systems and methods disclosed herein use a Cone Contrast Test (CCT) to identify hereditary color deficiency and acquired color vision loss associated with early disease/damage/toxicity to (a) alert for early disease/damage/toxicity and (b) monitor progression and treatment of such disease/damage/toxicity in an effort to (i) provide opportunity for earlier treatment, and (ii) prevent permanent eye damage.

BACKGROUND

The human eye sees color as a result of three types of receptors, called cones, listed in the chart below. A range of wavelengths of light stimulates each of these receptor types to varying degrees. Yellowish-green light, for example, stimulates both L and M cones equally strongly, but only stimulates S-cones weakly; red light stimulates L cones much more than M cones, and S cones hardly at all; blue-green light stimulates M cones more than L cones, and S cones a bit more strongly; and blue light stimulates S cones more strongly than red or green light, but L and M cones more weakly. The brain combines the information from each type of photoreceptor to give rise to different perceptions (i.e., colors) of different wavelengths of light.

| Cone type | Name | Range | Peak wavelength |
| --- | --- | --- | --- |
| S | B | 400-500 nm | 420-440 nm |
| M | Γ | 450-630 nm | 534-555 nm |
| L | P | 500-700 nm | 564-580 nm |

Test procedures such as optical computed tomography (OCT), visual field analyzers, etc., are used primarily to screen and diagnose specific eye disease. OCTs and visual field analyzers are tests generally used once the patient is symptomatic, well after permanent eye damage has occurred.

A test, called the Cone Contrast Test (CCT), is used to determine deficiencies of these cones in an individual's eye. The CCT is explained in greater detail in the published articles titled "Rapid Quantification of Color Vision: The Cone Contrast Test" by Rabin et al. published in *Investigative Ophthalmology & Visual Science*, February 2011, Vol. 52, No. 2, and "Quantification of Color Vision with Cone Contrast Sensitivity" by Jeff Rabin (2004), 21, pp. 483-485, the disclosures of which are hereby incorporated by reference.

The CCT is a functional test, making it a broad, non-disease-specific test. These features make CCT an affordable screening tool able to detect cone sensitivity degradation associated with a broad spectrum of disease/condition/toxicity early enough to, with treatment, potentially prevent permanent eye damage. The CCT may also be used as an early indicator for eye, systemic, and neurological disease and retinal toxicity, as well as a monitoring test for disease/toxicity progression and treatment.

Current testing procedures typically present a single colored letter, number, or symbol (e.g., a directionally oriented symbol or letter) at different contrast levels, with subsequent presentation at a higher or lower color contrast levels based on a patient's response, until the visual threshold is reached for that color. A patient typically responds to such stimulus by touching a response pad on separate region of a computer display, providing a verbal indication of the letter, number or symbol, or using a separate response pad and selecting the matching letter, number or symbol. Each of the above requires that a patient recognize a particular letter, number, or symbol that is presented, which requires both color vision and visual acuity.

The patient must often look away from the stimulus; a patient's poor visual acuity can interfere with testing procedures and results; and/or such types stimulus matching do not present well on computerized devices having small displays, such as smart phones, headsets (e.g., virtual reality-type headsets, or smart watches including displays, etc.).

When presented with a stimulus requiring matching, in most case, the patient must refocus their gaze and search for a correct answer from a plurality of possibilities in order to provide an input via a separate computer display region or, which can lengthen test time considerably. Accordingly, as test time is important to a clinician, lengthy test times can hinder the acceptance or usefulness of a product. While a directional stimuli, such as Landolt C's, used in combination with a directional response pad may eliminate the need to look away from the stimulus, this method still requires both color vision and visual acuity to perceive the stimulus. Moreover, a response pad may prove difficult for patients for patients that have problems with fine motor skills or are easily confused because any letter presentation inherently requires that the patient perform some type of matching, even if it is by feel—this can prove challenging both from physical and mental standpoints.

While letters, numbers, and symbols can be presented at a large acuity size, e.g., 20/200 or larger to minimize issues with visual acuity, a ceiling effect exists for low vision patients. That is, patients with visual acuity greater than 20/200 may be unable to identify a letter, number, or symbol due to limitations in their visual acuity, not their ability to see color. For example, patients with progressive diseases such as Retinitis Pigmentosa routinely have visual acuity less than 20/200, therefore, such types of stimulus may not be particularly effective at managing the disease. Moreover, in the case of smaller display areas, such as smartphone devices, it may not be possible to properly present letters, numbers, or symbols of larger acuity size for testing purposes limiting its usefulness for disease management even further.

Response pads displayed on a screen can be overly space-consuming in the case of smaller displays such as smartphones as these devices have limited display space. Separate response pads typically require connection via available communications ports or the use of such ports making them impractical for smaller displays such as smartphones, as they may not have the required ports. Moreover, wireless technologies, such as BlueTooth may be cost prohibitive to incorporate into a response pad. Hence, letter, number, or symbol matching is impractical for a smaller, computer-based devices such as smartphones.

What is needed, then, are methods and devices that address the above deficiencies.

SUMMARY

At the outset it should be understood that while the following disclosure, figures, and/or claims, etc., describe subject matter including one or more aspects described as either alone or in combination with one or more other aspects, the subject matter of the instant disclosure is not intended to be so limited. That is, the instant disclosure, figures, and claims are intended to encompass the various aspects described herein, either alone or in one or more combinations with one another. For example, while the instant disclosure may describe and illustrate a first aspect, a second aspect, and a third aspect in a manner such that the first aspect is only specifically described and illustrated relative to the second aspect, or the second aspect is only described and illustrated relative to the third aspect, the instant disclosure and illustrations are not intended to be so limiting and may encompass the first aspect alone, the second aspect alone, the third aspect alone, or one or more combinations of the first, second, and/or third aspects, e.g., the first aspect and the second aspect, the first aspect and the third aspect, the second and third aspect, or the first, second and third aspects.

According to aspects described and illustrated herein, there are provided methods and apparatuses for administering a cone contrast color vision test to a patient using a computer. The methods generally include the steps of simultaneously displaying a first color at a first contrast level in a first region of a display and a background color in the remaining regions of the display, which display is in communication with the computer, receiving a first input signal from the patient via an input device in communication with the computer, where the first input signal is indicative of whether the patient recognizes the first color displayed in the first region at the first contrast level, displaying the first color at a second contrast level in a third region of the display, where the first and third regions are chosen randomly, receiving a second input signal from the patient via the input device, where the second input signal is indicative of whether the patient recognizes the first color displayed in the third region at the second contrast level, assigning a score to the first and second input signals, the score related to a cone sensitivity of the patient to the first color at the first contrast level, storing the score in a storage device, comparing the score to at least one previous score associated with the patient to calculate a progression of a cone sensitivity loss in the patient, and displaying a graphical representation of the progression of the cone sensitivity loss in the patient. In an additional aspect, the first color at different contrast levels may be presented simultaneously in differing regions, e.g., first, third, and fifth regions, etc., where the input signal is indicative of the lower color contrast level the patient is able to see.

In an additional aspect, the first color comprises one of red, green, or blue, and the second color is grey. In further aspects, the second contrast level of the first color is different than the first contrast level of the first color. In some aspects, when the first and second region are simultaneously displayed, the first region does not simultaneously occupy the second region.

In some aspects, the first and third regions are disposed in one of an upper, leftward, rightward, or lower region of the display and a position of the first and third regions are randomly selected.

In some aspects, the first and second input signals comprise at least one of a touch input, a voice input, or an eye tracking input, and the input device is attached to and implemented via the computer.

In some aspects, at least one of the first and second contrast levels is set to a predetermined default value if there are no prior cone contrast color vision test records associated with the patient.

In some aspects, steps (a) through (f) are repeated sequentially using values for the first and second contrast levels based on the values for the patient response of the first and second contrast levels in a prior iteration of the cone contrast color vision test to determine a lowest cone sensitivity of the patient.

In additional aspects, sine wave gratings are presented to measure a patient's contrast sensitivity as a function of their spatial frequency. The first and second contrast levels of the first and third regions are created by modifying the color saturation or intensity level of the first color using linear or concentric circle sinusoidal gratings, spatial dithering, or temporal dithering. In some aspects, the first and third regions comprise a sign wave grating pattern formed using the first color presented between the first and second color saturation or intensity level, and thereby creating a specific color contrast level s. The patient's threshold for contrast sensitivity of the sine wave grating is determined by increasing or decreasing the color saturation or intensity level based on the patient response until he can no longer see the linear or concentric circle gratings. In some aspects, the first and second color contrast levels of the sign wave grating pattern presented by varying the spatial frequency (measured in cycles/degree) of the first color presented between the first and second intensity levels.

In some aspects including sine wave grating, the first and third regions are displayed in one of an upper, leftward, rightward, or lower region of the display and a position of the first and third regions is randomly selected. In some aspects including sine wave grating, the first and third regions are displayed in a quadrant of the display and the quadrant of the first and third regions is randomly selected.

In some aspects, the first contrast level of the second color is the same as the second contrast level of the second color. In some aspects, the first contrast level of the second color is different from the second contrast level of the second color.

In some aspects, there is described a method for displaying a simulated depiction of the vision of a patient with cone sensitivity loss, including the steps of receiving on a computer at least one cone contrast color vision test record associated with the patient, displaying at least one sample image depicting normal vision without cone sensitivity loss on a display attached to the computer, modifying the at least one sample image into at least one modified image according to a specific level of cone sensitivity loss recorded in the at least one cone contrast color vision test record associated with the patient, such that the at least one modified image depicts the at least one sample image as it would been perceived by the patient, and displaying the at least one modified image on the display.

While the inventive aspects are susceptible of embodiments in many different forms, there is shown in the drawings and will herein be described in detail preferred aspects with the understanding that the present disclosure is to be considered as an exemplification of the principles of the inventive aspects and is not intended to limit the broad inventive aspects to the specific embodiments illustrated.

The inventive aspects include a method and apparatus for screening and monitoring progression and treatment of retinal disease, glaucoma, neurological disorders and other systemic pathologies affecting the eye. The method and apparatus include a Cone Contrast Test (CCT) which measures and scores color perception by cone type and assigns a score by cone type. The method and apparatus further include a comparison of such scores to a base line. Using CCT for the screening of potential disease/toxicity is an efficient, fast and low-cost procedure.

The apparatus comprises a computer, including input device and display device, for administering the CCT to individuals and, based on the test results and other factors, determining the early and late stages of one of Glaucoma, Retinopathy, Age-Related Macular Degeneration, Multiple Sclerosis, potentially Alzheimer's Disease and Parkinson's Disease, as well as Retinal Toxicity due to high-risk medications, as disclosed in the Appendices. The method is implemented by the apparatus.

The Cone Contrast Test preferably presents random colored regions or areas—instead of letters numbers, or characters requiring visual acuity—so as to excite the red, green and blue cones in decreasing contrast sensitivity levels to identify the patients' Cone Contrast threshold and score for each cone type in each eye. The colored regions or areas are presented at a size well above a "normal" 20/20 acuity level so that the patient's cone contrast score is not affected by a limited acuity ability.

Upon each presentation of a colored region or area, the patient selects the perceived corresponding region by means of touching that region or area of a touchscreen display upon which the colored region is displayed, by mean of providing a voice command in conjunction with voice recognition software executed on a computer, for example, or by mean of an eye tracking input as may be provided by eye-tracking software executed on a computer. If the patient does not see a colored region, a "Pass" option may be provided using any of the above methods.

The patient interface consists of a computer (e.g., a desktop, a laptop, or smartphone, etc.), a display, and an input mechanism, which may include a touch screen, a microphone in communication with a controller executing voice recognition software, or a camera or optical sensor in conjunction with a controller executing eye-tracking software capable of tracking eye movements or patient gaze or camera in conjunction with a controller executing gesture-tracking software capable of tracking hand gestures.

The Cone Contrast Test is fully automated, presenting each region or area for a specific, limited duration. Limiting the presentation time speeds up the test and may prevent a color deficient patient from potentially perceiving visual clues to aid in a response and potentially affecting the score.

Further, elderly patients may not be familiar with computers, and thus may not be as responsive even though they are not color deficient. A "blanking period" option may be selected for patients requiring more time with the response unit. Specifically, after the region or area is presented for a fixed duration, the target region or area is removed from the screen. The "blanking period" allows older patients, as well as patients with physical or cognitive limitations enough time to respond without introducing visual clues that could potentially alter their actual threshold and score.

Alternatively, an Orientation Screen, presented prior to the test for each eye, may detect the actual response time for the individual patient and adjust the presentation time for each region or area to achieve a Patient-Specific Presentation Time that would accommodate the need for additional response time due to computer, physical or cognitive limitations of each individual patient.

The blanking option or patient-specific presentation time is a key component for the Early Eye Disease Detection and Monitoring component of the Cone Contrast Test, as the majority of patients developing eye disease are elderly and may need extra time to respond due to unfamiliarity with a computer or smartphone or physical or cognitive limitations.

In an example embodiment, the administration of the test is sped up by using a "learning" test algorithm based on the patient's prior CCT test results. The CCT test updates the patient's record automatically on completion of the CCT test. Alternately, the contrast scores may be entered manually from the patient's prior CCT exam. This learning test algorithm significantly reduces the number of cone contrast levels presented on future presentations.

The following fields are included on the Patient Record to be accessed by the CCT test: Last red cone contrast score left eye, Last green cone contrast score left eye, Last blue cone contrast score left eye, Last red cone contrast score right eye, Last green cone contrast score right eye, Last blue cone contrast score right eye.

At the commencement of the CCT test, the patient record is read for last cone contrast scores. If no previous scores are found, it is assumed that this is a new patient and the test continues with the normal algorithm. And, if any last cone contrast values from the patient record listed above have a value, the starting cone contrast level is altered based on the last cone contrast score for that eye/cone. If a last cone contrast score is found in the patient record, the test calculates the corresponding cone contrast level and begins the CCT Test for that cone 1-2 levels above the corresponding cone contrast score for that eye. If multiple values are found, the CCT test alters each corresponding part of the test accordingly.

In an example aspect, a staircase method is used to present color contrast levels by cone type, allowing the test to be administered more quickly. The contrast presentations are reduced by two levels at a time if the patient correctly identifies the character at that contrast level. The contrast level is increased if two or more regions or areas within a contrast level are incorrectly identified. The algorithm for each cone can be altered individually or in combination based on the fields populated in the patient record.

The colors presented are precisely selected to excite only one cone type at a time, allowing each cone type to be measured and scored independently.

Off-the-shelf equipment is calibrated for both color and contrast. The color presentation must be accurate so that each cone type is tested individually (i.e., only one cone type responds). In turn, the accuracy of the color contrast levels is important to determine threshold level. Custom equipment with superior displays may not require ongoing calibration.

The current system can include software that does not allow other software to change color or contrast calibration settings, to achieve a reliable computerized color vision test using a low-cost colormeter.

The disclosed system can utilize display calibrating colormeter hardware, such as SPYDER X™ and related versions, manufactured and sold by DATACOLOR of Lawrenceville, NJ.

Since the CCT begins with establishing a baseline for each cone type for an individual and looks for degradation of the individual's color perception through repeated testing over time, stable color contrast levels are critical. This may be accomplished through system calibration for custom hardware. Computer equipment and colormeters can be changed, drift or fail over time, allowing color and contrast values to become out of calibration. To ensure that equipment stays within calibration and test results remain valid, the software forces an automatic in-field periodic calibration check. The CCT is self-calibrating, requiring the user only to position the photometer on the monitor and start the calibration. The calibration verification is done automatically and checks calibration values to original calibration values done at initial manufacturing. If the calibration is outside of tolerance, the system forces a complete calibration. If the calibration is still outside of tolerance, the system will alert the user and disable the use of the Cone Contrast Test until calibration can be completed within tolerance.

The duration between each calibration is established during set-up and may be adjusted based on clinic testing policy and procedure. The calibration time frame can be pre-set for every seven days but may be set according to individual testing policy and preference. Preferably, calibration automatically occurs at a predetermined interval of time. The automation alleviates the fear by some that the calibration may be skipped and test results may be rendered invalid.

Automated calibration verification enables a user to check for failing/failed hardware, including colormeter, monitor, or computer changes to ensure valid test scores. The calibration verification of the present system is preferably set at a seven (7) day interval, requiring calibration be checked against the original calibration settings. Any significant change from original calibration settings requires a full calibration. If a full calibration is still outside of tolerances, the Cone Contrast Test is disabled until a calibration can be completed within tolerance. Replacing equipment, such as a photometer, monitor or CPU, may be required to achieve a valid calibration.

Since the equipment may be used for both screening and monitoring of disease/toxicity, the equipment has both a screening mode and a comprehensive testing mode to allow for Medicare or other insurance billing, with the comprehensive mode providing more thorough examination and reporting. A doctor specifies the mode based on the use of the instrument for the specific exam before conducting the test.

Variations in the testing method may include, but are not limited to (1) altering distance between a display screen and an individual (e.g., 3, 4 or 6 meters), (2) a user interface such as voice recognition commands, wireless keyboards or other wired or wireless input devices, (3) blanking period or patient-specific response time, and (4) screening and testing modes.

Each test is scored by cone type and any cone deficiency is determined by comparing the patient's scores over time. Accuracy of CCT is very high in detecting Red, Green and Blue cone deficiencies. Deficiencies which present over time are predictive of early ocular, systemic and neurological disease as well as retinal toxicity, whereas such deficiencies may otherwise be overlooked as anomalies.

Storing of cone contrast sensitivity scores and reporting data in a way that shows cone contrast sensitivity changes over time allows for potential disease/toxicity alerts. Reports show a change in cone contrast sensitivity by patient, per eye, by cone type and display an alert when the cone contrast sensitivity change is statistically significant. The reports can be viewed or printed to alert doctors and patients of potential disease or toxicity that should be further investigated.

Currently, significant change is thought to be the normal distribution of color normal patients score, >15 points. Further research may show that changes less than 15 points may also be significant to a specific patient baseline.

This type of tracking and reporting mechanism has never before been available, limiting prior art systems and methods to hereditary color deficiency scoring use or research where time permits for manual comparison. The disclosed system and methods are the first CCT usable as an early eye, systemic and neurological disease and retinal toxicity detection system in a clinic setting, where time with the patient is limited. Comparison data and alerts are critical to interpret test results in the time frame required in a clinical setting.

Patient reports may be stored on a non-transitory computer readable medium such as a hard drive or memory device and may be uploaded to electronic medical records. In addition to running the test and computing and storing the test results on a single computer, the test may be run on any of a number of smartphones, smartwatches, headsets, laptops, networked or standalone computers, and the test results may be computed and/or stored on any of a network of computers. This arrangement ensures that a patient need not take a subsequent test on the same computer to ensure his record is present, and it allows for the sharing of the test results and patient records between computers in distant physical locations. The network of computers may include locally networked computers or computers connected through shared access to the Internet or a cloud of computers.

In an example embodiment, the computers implementing the CCT test use a sync function consisting of three steps: 1. identifying the CCT computers in the network to be synced into a central network database, 2. identifying and uploading the records from each CCT device on the network which need to be synced with the central network database; 3. identifying and download the records in the central network database which need to be downloaded and which local CCT device requires the download.

A sync file containing the practice name and unique device identifier for each CCT device is established as part of the setup of the central network database to control which devices get synced to the central network database. Proprietary sync software, located on the network, accesses all devices in the sync file network, syncs activity from the local databases into a single network database, and syncs each local device database with the contents of the central network database. The sync function can be scheduled for the same day and time or started manually. A sync timer setting is available as a system setting, residing on the network database which establishes the day and time for a scheduled sync.

An upload sync flag is part of the patient file as well as the patient test records file. Upon the completion of the addition or change to a patient record, the upload sync flag in the patient file is set to 1, flagging the file to be uploaded to the central network database upon the next sync. Upon the completion or deletion of a patient test, the patient test record upload sync flag is set to 1, flagging the file for upload to the central network database upon the next sync.

Upon the execution of the upload sync function, each uploaded patient or patient test record sync flag is set to 0, flagging the record as already synced. Download sync flag(s) 1 through x, based on the number of local CCT devices in the sync file, are also part of both the patient file as well as the patient test records file. As each record is uploaded to the network database, a download sync flag is set to the unique device identifier of the contributing CCT device.

Upon the download sync function, the first local CCT device in the sync file is accessed. Records in the central database that do not include the download sync flag for that local device are downloaded. After each record is downloaded to the local machine, the unique device identifier is added to the record on the central network database. Each local CCT device listed in the sync file is accessed in a similar manner. Since each record tracks the devices that have been synced, additional devices may be added at any point in time and are able to be synced into the network.

The patient test file also has a test device field. Upon the completion of the CCT test, the unique device identifier is recorded in the test device field. The test device field is used to identify the device on which the test was taken in the event that the test has erroneous or outlying results that may signify a device which needs to be recalibrated or otherwise serviced.

In an example aspect, all records are copied to the central network database and repopulated to each local database.

As previously discussed, patient response time is captured and recorded for each cone type for every Cone Contrast Test. Mean response time by cone type, and by eye, is calculated and reported. Response times have been shown to correlate closely with cone deficiency, with color normal patients responding consistently within two seconds and color deficient patients responding much slower. Cone Contrast Sensitivity Response Time may serve as a new sensitive metric of color deficiency and early indicator of eye, systemic or neurological disease.

These and other aspects, features, and advantages of the present disclosure will become readily apparent upon a review of the following detailed description of the disclosure, in view of the drawings and appended claims.

BRIEF DESCRIPTION OF THE DRAWINGS

Various aspects are disclosed, by way of example only, with reference to the accompanying drawings in which corresponding reference symbols indicate corresponding parts, in which:

FIG. 2a is a screen shot of an inventive aspect;
FIG. 2b is a screen shot of an inventive aspect;
FIG. 3a is a screen shot of an inventive aspect;
FIG. 3b is a screen shot of an inventive aspect;
FIG. 20 is a screen shot of an inventive aspect;
FIG. 25 is a flow chart of an inventive aspect;
FIG. 26 is a schematic view of an inventive aspect.

DETAILED DESCRIPTION

Figure 1:
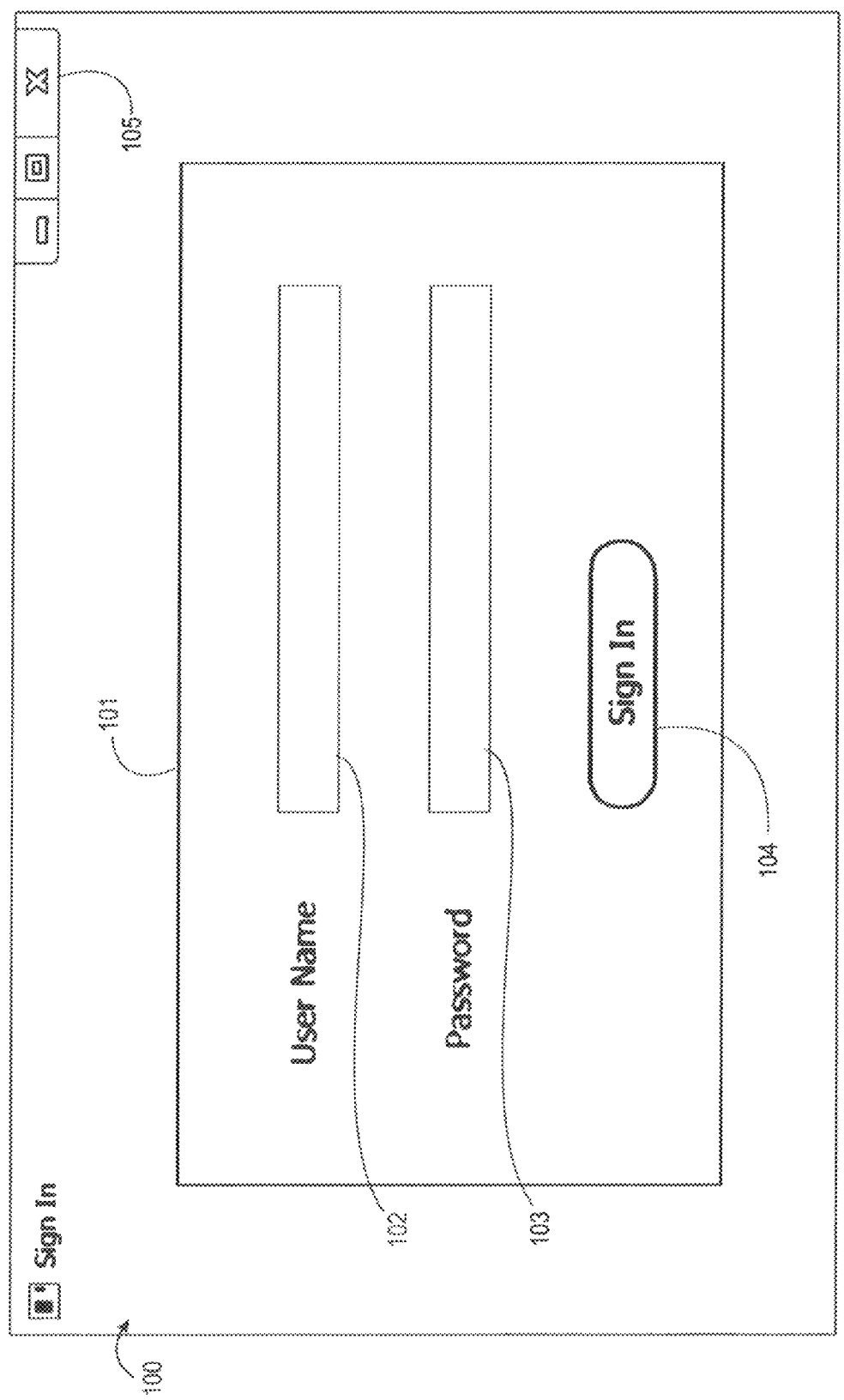
FIG. 1 is a screen shot of an inventive aspect.

At the outset, it should be appreciated that like drawing numbers on different drawing views identify identical, or functionally similar, structural elements of the embodiments set forth herein. Furthermore, it is understood that these embodiments are not limited to the particular methodology, materials and modifications described and as such may, of course, vary. It is also understood that the terminology used herein is for the purpose of describing particular aspects only and is not intended to limit the scope of the disclosed embodiments, which are limited only by the appended claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice the example aspects.

It should be appreciated that the terms "substantially" and "generally" are synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

As set forth herein, the term "computer" is intended to refer to an electronic type computing device generally including a processor and a memory device, and may include one or more of display device, an input device such as a keyboard, mouse, touchscreen, microphone, camera or photosensor, etc., or other input electronic device, as well as other output devices such as loudspeakers or other visual or devices capable of outputting sensory indicia, e.g., sounds, lights, vibrational cues. etc. A "computer", thus, may include devices such as a desktop or laptop computer, a so-called tablet computer, a smartphone, and/or a so-called smartwatch or virtual reality headset device that may or may not be in communication with another device, and like devices.

It should be understood that use of "or" in the present application is with respect to a "non-exclusive" arrangement, unless stated otherwise. For example, when stating that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

As previously set forth, while the following disclosure and accompanying figures, and/or claims, etc. describe subject matter including one or more aspects described as either alone or in combination with one or more other aspects, the subject matter of the instant disclosure is not intended to be so limited. That is, the instant disclosure, figures, and claims are intended to encompass the various aspects described herein, either alone or in one or more combinations with one another. For example, while the instant disclosure may describe and illustrate a first aspect, a second aspect, and a third aspect in a manner such that the first aspect is only specifically described and illustrated relative to the second aspect, or the second aspect is only described and illustrated relative to the third aspect, the instant disclosure and illustrations are not intended to be so limiting and may encompass the first aspect alone, the second aspect alone, the third aspect alone, or one or more combinations of the first, second, and/or third aspects, e.g., the first aspect and the second aspect, the first aspect and the third aspect, the second and third aspect, or the first, second and third aspects.

It will be appreciated that various aspects of the disclosure and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

As discussed above, a cone contrast test may use a staircase method of detecting a patient's cone contrast threshold by presenting colored letters specific to each cone type in decreasing and/or increasing contrast steps until reaching the patient's threshold for that specific cone type. It tests all three color values—red, green and blue—in both right and left eyes. Characters or optotypes are presented at 20/200 (red, green) and 20/300 (blue) to avoid acuity function interference. The CCT presents letters at 5 color contrast levels, decreasing by two color contrast levels or jumps until the patient responds incorrectly. At that time, the color contrast level presentations begin at the next higher color contrast level and proceeds in a sequential fashion through the duration of the test. The patient's cone score is determined based on the number of correct responses at each level.

Adverting now to the Figures, the following Figures show screenshots of testing software 100. FIG. 1 shows sign in screen 101 driven by a computer. Sign in screen 101 comprises user name field 102, password field 103, and sign in button 104. Upon commencing testing software 100, sign in screen 101 appears. In order to access testing software 100, a patient taking a CCT or an administrator directing the CCT, must input a user name and a password into user name field 102 and password field 103, respectively. A user can exit testing software 100 by selecting exit button 105 located at the top right of sign in screen 101.

Figure 2:
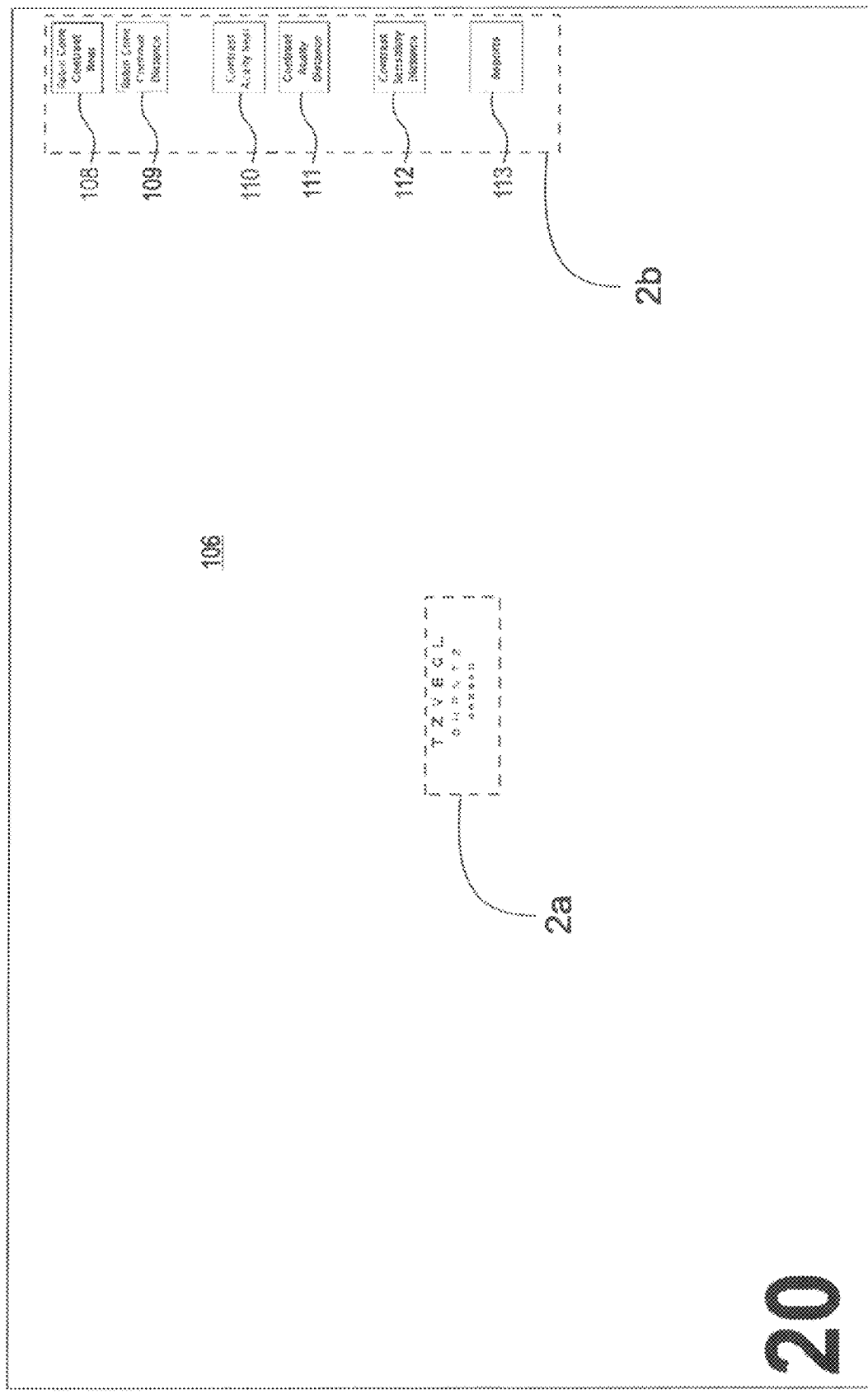
FIG. 2 is a screen shot of an inventive aspect.

Once sign in button 104 is selected, presentation option screen 106 of testing software 100 appears as shown in FIG. 2. Presentation option screen 106 comprises CCT near button 108, CCT distance button 109, contrast acuity near button 110, contrast acuity distance button 111, contrast sensitivity distance button 112, and reports button 113. The CCT may be conducted while a patient is seated at a desk with the computer displaying the CCT mounted thereon. In this case, a patient can use a computer mouse or some other means to select buttons in testing software 100 to be described in more detail below. Alternatively, the CCT may be conducted while a patient is seated or standing a distance from the computer displaying the CCT. In this case, an administrator directing or overseeing the CCT can operate a mouse in communication with the computer displaying the CCT or some other interface may be involved to input a patient's responses. For example, voice recognition software could be used to transmit a patient's selections in or responses to the CCT, or a wireless mouse could be used. In an example embodiment, the patient responds by verbally announcing the character or symbol displayed on the display monitor. In addition to the aforementioned case in which the technician enters the patient's verbal response, the patient's verbal response may be received by a microphone attached to the computer. Voice recognition software running on the computer then translates the patient's verbal response into a textual response identical to text input from a keyboard. Use of computer voice recognition is selectable and may be turned off on a case by case basis. In an example embodiment, speakers, and wireless or wired headphones or headsets may be used to relay audible instructions or indications to the patient. Headphones may better accommodate both voice recognition and the voice confirmation of patient responses for patients at longer distances or in test environments in which multiple devices are being used in a small area.

Regardless of the method used, CCT can be administered with a patient arranged proximate the display screen and at a distance away from the display screen. If CCT near button 108 or contrast acuity near button 110 is selected, testing software 100 is directed to use characters at a default size based on the calibration of testing software 100. If CCT distance button 109 is selected, testing software 100 is directed to display higher quality characters, down to 20/10, during the CCT depending on the patient's distance from the computer display. Selecting CCT distance button 109 will cause testing software 100 to produce a distance field and the patient's distance from the computer display will need to be inputted into the distance field and transmitted to testing software 100 so the properly sized characters are used. For best results, the patient should be parallel to the display. Selecting contrast acuity distance button 111 or contrast sensitivity distance button 112 will similarly direct testing software 100 to use higher quality characters, down to 20/10, during the acuity or sensitivity tests depending on the patient's distance from the computer display. Reports button 113 will be discussed in more detail below.

In an example embodiment, the CCT test is presented to the patient as an enclosed device. Specifically, the enclosed device includes the computer implementing the CCT test, the display to be viewed by the patient, a chin rest arranged at a predetermined distance from the display (see FIG. 26), and the input device. The patient places his forehead and chin on the chin rest and the characters or symbols are presented on the display. In an example embodiment, the enclosed device uses mirrors, projection or magnification to size the letters to the desired test distance. The enclosed device allows the distance CCT test to be administered in a much smaller area, such a pre-test or screening room and enforces a predetermined distance between the display and the patient's eyes.

For consistent results, lighting should controlled. The CCT should be conducted in dim room lighting. No light should be directed at the CCT display. However, some indirect lighting is acceptable and will not interfere with the test.

Figure 3:
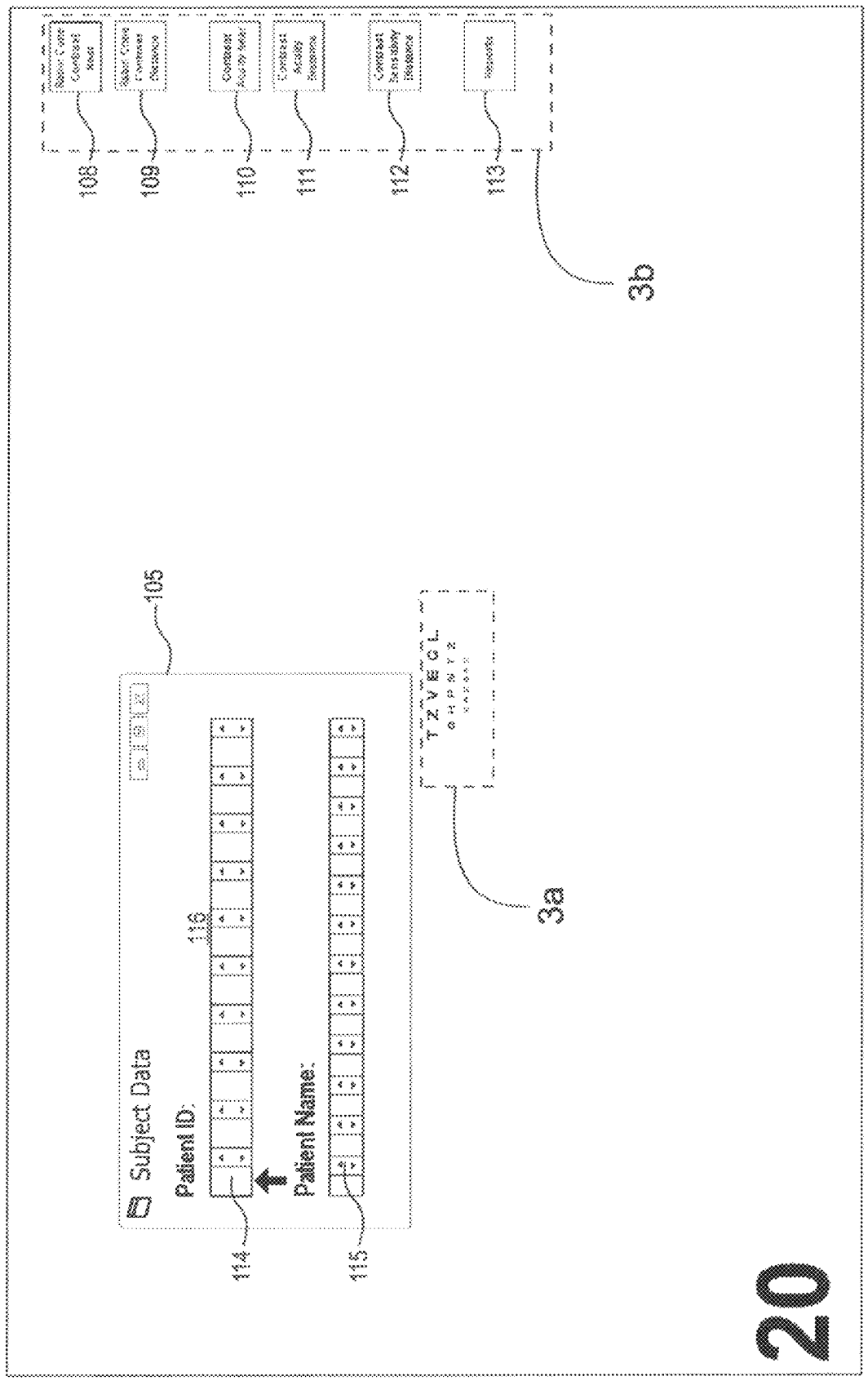
FIG. 3 is a screen shot of an inventive aspect.

Selection of the type of test desired (CCT near button 108, CCT distance button 109, contrast acuity near button 110, contrast acuity distance button 111, or contrast sensitivity distance button 112) will direct testing software 100 to produce subject data screen 116. Subject data screen 116 comprises patient ID field 114 and patient name field 115 shown in FIG. 3. Patient ID field 114 of testing software 100 is arranged to receive a 1-10 digit number identifying a patient. The number can be input using a keyboard, for example. A patient's name, for example, John Doe is inputted into patient name field 115 using a keyboard, for example. It should be appreciated that other means such as, voice recognition software could be used to populate patient ID field 114 and patient name field 115. To start the test, a patient or an administrator presses the "Enter" button on a keyboard. The test can be started without inputting data into patient ID field 114 and patient name field 115. A user can exit testing software 100 by selecting exit button 105 located at the top right of subject data screen 116.

The CCT test can be implemented using any characters preferably, letters or numbers. For Dyslexic patients, conducting the test using numbers may yield more favorable results. In an example embodiment, Snellen letters and/or non-character symbols may be used in the administration of the test. Examples of these non-character symbols include, but are not limited to, children's symbols, such as Allen Symbols, Lea Symbols or Patti Pics Symbols, as well as other ophthalmic symbols such as Tumbling Es or Landolt Cs. In the case of Tumbling Es or Landolt Cs, the responses would include left, right, up and down.

Figure 4:
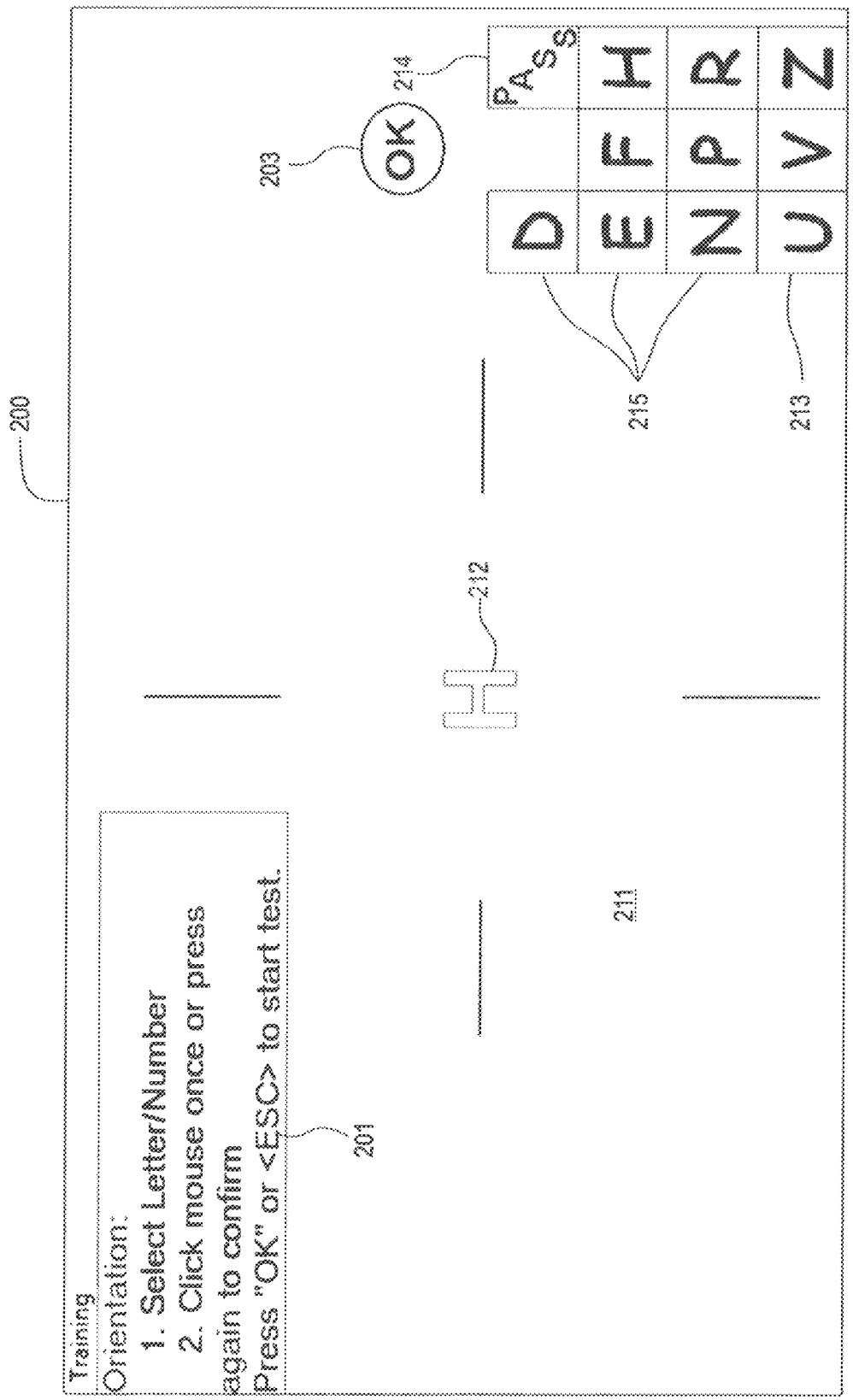
FIG. 4 is a screen shot of an inventive aspect.

FIG. 4 shows orientation testing screen 200. Orientation testing screen 200 comprises orientation instruction pane 201, confirmation button 203, testing field 211, testing symbol 212, response table 213, and pass button 214. Response table 213 comprises plurality of response symbols 215. In some embodiments of the invention, orientation testing screen 200 is displayed immediately upon commencement of the CCT process. By displaying orientation testing screen 200 prior to other portions of the CCT, the method of taking the CCT can be relayed and practiced by the patient taking the CCT. Orientation instruction pane 201 contains written instructions on the specific steps the patient taking the CCT should take during the testing process. Orientation instruction pane 201 also contains instructions for advancing to the other portions of the CCT.

In the embodiment of the invention shown in FIG. 4, the written instructions in orientation instruction pane 201 instruct the patient taking the CCT to identify testing symbol 212 in testing field 211 and select the equivalent symbol from the plurality of response symbols 215 in response table 213. In some embodiments of the invention, the specific symbols included in response table 213 will be selected randomly, but in all embodiments of the invention, a symbol equivalent to testing symbol 212 must be one of response symbols 215 in response table 213.

This initial selection of one of the symbols of the plurality of response symbols 215 in response table 213 highlights the selected symbol for review by the patient. In some embodiments of the invention, selecting one of the plurality of response symbols 215 will cause testing software 100 to produce a sound corresponding to the symbol selected, such as saying the name of the letter if the plurality of response symbols 215 are letters. Selecting the same symbol again will act as a confirmation and indicate to testing software 100 that the patient believes the symbol selected from the plurality of response symbols 215 in response table 213 to be the same as the testing symbol 212.

If the patient taking the CCT cannot identify testing symbol 212, the patient may select pass button 214. This will indicate to testing software 100 that the patient is unable to identify testing symbol 212. In some embodiments of the invention, selecting the pass button will be recorded as an incorrect identification for patient color vision assessment purposes.

Upon confirmation of a symbol from the plurality of response symbols 215 in response table 213 or selection of pass button 214, testing software 100 will record the response and orientation testing screen 200 will refresh. Upon refreshing, orientation testing screen will display a new testing symbol 212. The patient taking the CCT will then select one of the plurality of response symbols 215 in response table 213 or pass button 214, continuing the orientation process. When the patient is confident that he or she understands the method of taking the CCT, the orientation process can be ended by selecting the confirmation button 203.

Figure 5:
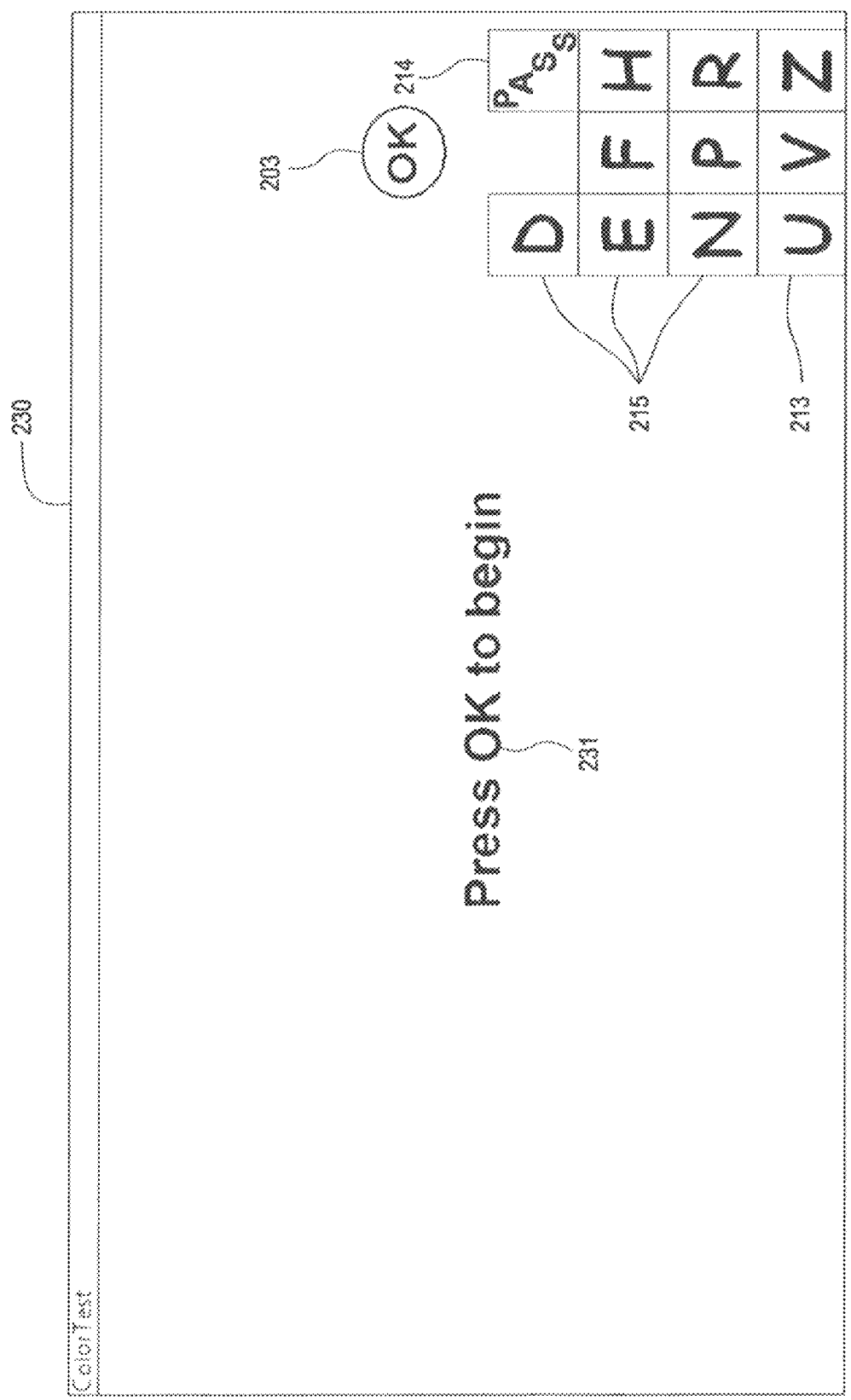
FIG. 5 is a screen shot of an inventive aspect.

FIG. 5 shows test commencement screen 230. Test commencement screen 230 comprises commencement message 231, confirmation button 203, response table 213, and pass button 214. Response table 213 comprises plurality of response symbols 215. Test commencement screen 230 is displayed immediately prior to the commencement of the testing portions of the CCT to announce that the test process is ready to begin. The patient taking the CCT will select confirmation button 203 when they are ready to begin the testing process. Although response table 213 and pass button 214 are components of test commencement screen 230, they are not active, i.e., they cannot be selected.

Figure 6:
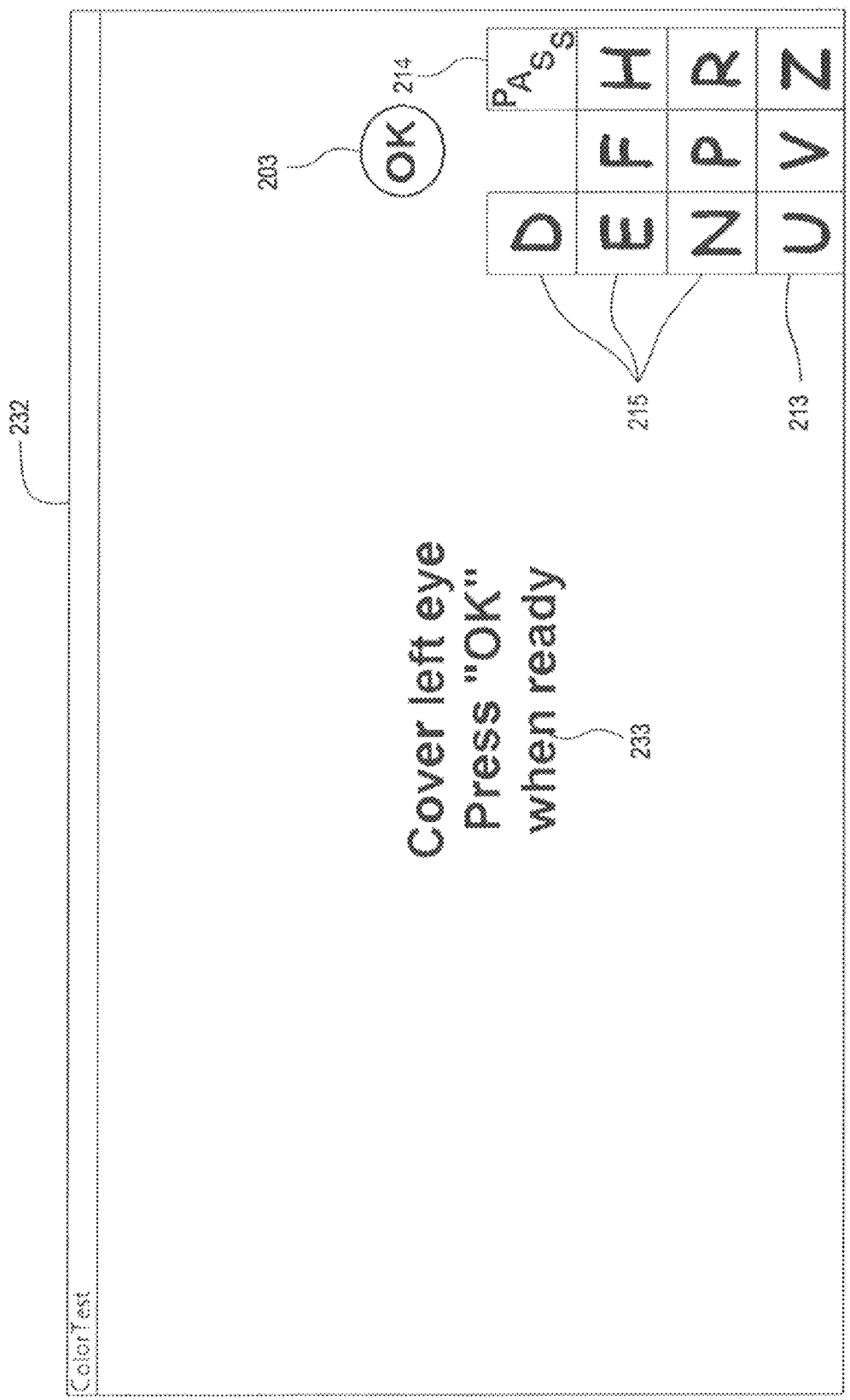
FIG. 6 is a screen shot of an inventive aspect.

FIG. 6 shows eye selection screen 232. Eye selection screen 232 comprises eye selection message 233, confirmation button 203, response table 213, and pass button 214. Response table 213 comprises plurality of response symbols 215. Eye selection screen 232 is displayed immediately prior to each of the two eye-specific portions of the CCT. As color vision can be different in the left and right eyes of the patient taking the CCT, it is beneficial to test the left and right eyes individually. By testing the left and right eyes individually, a more thorough understanding of the patient's color vision can be obtained.

Eye selection message 233 indicates which eye will be tested in the following test portion. For example, if the right eye is to be tested in the following test portion, eye selection message 233 would instruct the patient to cover their left eye and perform the test with their right eye only. The patient taking the CCT will select confirmation button 203 when they are ready to begin the testing process for the eye indicated in eye selection message 233. Although response table 213 and pass button 214 are components of eye selection screen 232, they are not active, i.e., they cannot be selected.

Figure 7:
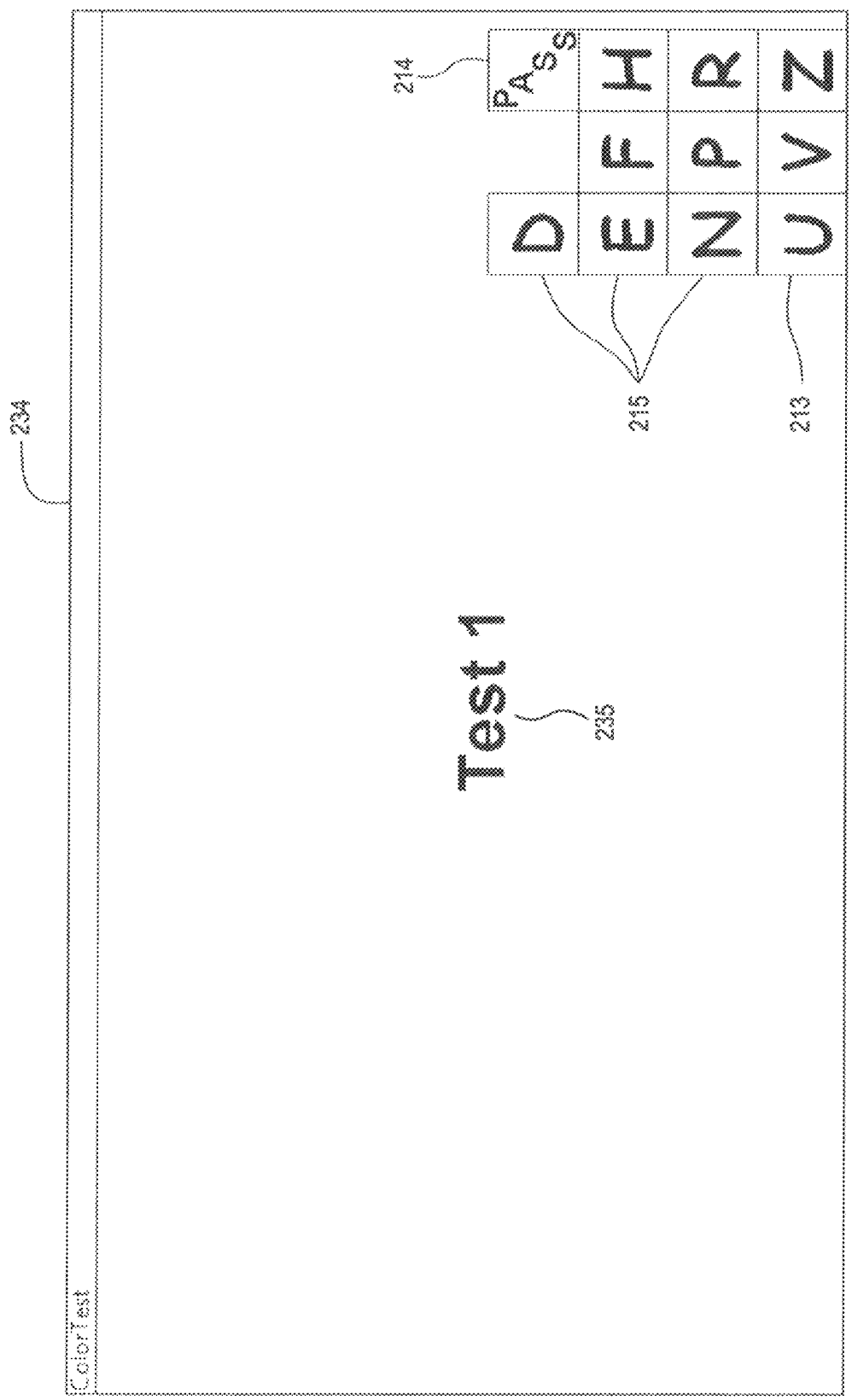
FIG. 7 is a screen shot of an inventive aspect.

FIG. 7 shows color phase screen 234. Color phase screen 234 comprises color phase message 235, response table 213, and pass button 214. Response table 213 comprises plurality of response symbols 215. Color phase screen 234 is displayed immediately prior to each of the three color-specific phases of the visual acuity test.

The ability of humans to perceive different colors of light is made possible by specialized photoreceptor cells in the retina called cone cells. Each of the three different types of cone cells detects a different portion of the visual spectrum, and each type is most sensitive to a certain color of light. The three different types of cone cells are most sensitive to colors that correspond approximately to the colors of red, green, and blue. Colors other than red, green, and blue are perceived via the combination in the human brain of signals from multiple types of cone cells and their relative intensities. For example, the color yellow is perceived when the red and green cone cells are stimulated approximately equally. The phenomenon of perceiving the full spectrum of visible light based on the combination of signals from three types of cells, each of which detects a different color, is called trichromacy.

As human vision is trichromatic, deficiencies in one or more of the types of cone cells can impair the ability of an individual to perceive certain colors. However, because each type of cone cell is most sensitive to a certain color of light, it is possible to individually assess the sensitivity of cone cells of a certain type by testing the ability to distinguish image components made of the color that the corresponding type of cone cell is most sensitive to. For this reason, the CCT has three phases for each eye, a red phase, a green phase, and a blue phase. For example, in the red phase, the sensitivity of the red-type cone cells is assessed. In this way, the sensitivities of the red-type, green-type, and blue-type cone cells in each eye can be assessed.

Color phase message 235 announces to the patient taking the visual acuity test which color phase is about to begin. As the patient does not need to prepare for the specific color phases, the patient does not have to select any particular interface component to continue to the portion. The test process will continue automatically after a predetermined amount of time. Although response table 213 and pass button 214 are components of color phase screen 234, they are not active, i.e., they cannot be selected.

Figure 8:
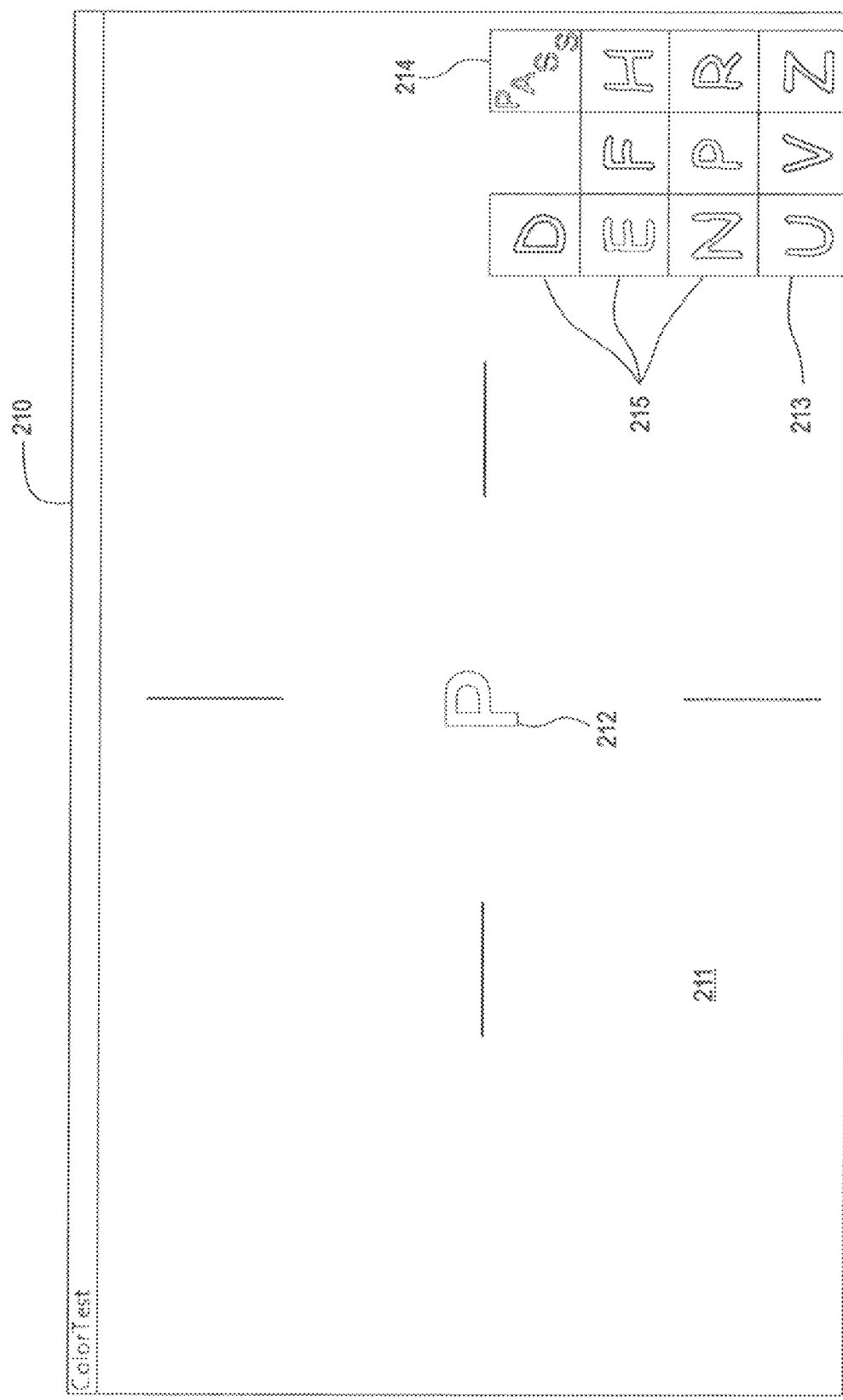
FIG. 8 is a screen shot of an inventive aspect.

FIG. 8 shows testing screen 210. Testing screen 210 comprises testing field 211, testing symbol 212, response table 213, and pass button 214. Response table 213 comprises plurality of response symbols 215. Having familiarized themselves with the testing method during the orientation portion of the CCT, the patient taking the test will be able to perform the test without further instruction. Testing symbol 212, is either red, green, or blue, depending on which color phase the testing process is currently in. For example, in the red color phase of the testing process, testing symbol 212 will be red.

The sensitivities of the different types of cone cells is assessed by showing the patient taking the CCT a testing symbol 212 of the color exciting only the cone type of the present color phase on testing field 211. Initially, there is a large contrast differential between testing symbol 212 and testing field 211. Due to this high contrast differential, it is easier for the patient to distinguish the shape of testing symbol 212 and select the equivalent symbol from the plurality of response symbols 215 in response table 213. By iteratively reducing the contrast differential between testing symbol 212 and testing field 211 and asking the patient to select the equivalent symbol from the plurality of response symbols 215 in response table 213, until the patient is unable to correctly identify testing symbol 212, the ability of the specific cone cell types of the patient's specific eye can be assessed.

In embodiments of the invention, a symbol equivalent to testing symbol 212 must be one of response symbols 215 in response table 213.

This initial selection of one of the symbols of the plurality of response symbols 215 in response table 213 highlights the selected symbol for review by the patient. In some embodiments of the invention, selecting one of the plurality of response symbols 215 will cause testing software 100 to produce a sound corresponding to the symbol selected, such as saying the name of the letter if the plurality of response symbols 215 are letters.

If the patient taking the CCT cannot identify testing symbol 212, the patient may select pass button 214. This will indicate to testing software 100 that the patient is unable to identify testing symbol 212. In some embodiments of the invention, selecting the pass button will be recorded as an incorrect identification for patient visual acuity assessment purposes. Additionally, in some embodiments of the invention, if the patient does not select any of the plurality of response symbols 215 in response table 213 in a predetermined amount of time, such inaction will be recorded as an incorrect identification for patient color vision assessment purposes. The predetermined amount of time before an incorrect identification is registered may be varied depending on the purpose of the color vision test. For example, if the purpose of the test is to measure hereditary color vision deficiency of pilots and/or pilot applicants, the ability to make timely determinations may be more important than if the purpose of the test is to test for acquired color vision loss. In such a case, the predetermined amount of time before an incorrect identification is registered may be reduced.

If the patient correctly identifies testing symbol 212 by selecting the equivalent symbol from the plurality of response symbols 215 in response table 213, testing software 100 will record a correct identification and continue the test process. In one embodiment of the invention, two correct identifications in succession by the patient at a specific contrast differential level will cause testing software 100 to display a testing screen 210 with a testing symbol 212 two contrast differential levels lower than the immediately preceding testing symbol 212. In some tests, however, only one presentation may occur.

If the patient selects an incorrect response symbol from the plurality of response symbols 215 in response table 213, then testing software 100 will record an incorrect identification. If the patient selects pass button 214, then testing software 100 will record that the patient chose to pass. In an embodiment of the invention, if the patient selects an incorrect response symbol from the plurality of response symbols 215 in response table 213, the testing software will display a testing screen 210 with a testing symbol 212 one contrast differential level higher than the immediately preceding testing symbol 212.

In yet another embodiment, if the patient correctly identifies two testing symbols 212 of a given contrast differential level, even if such correct identification is separated by an incorrect identification, or a selection of pass button 214, or the registering of an incorrect identification by the lapsing of the predetermined amount of time, then the testing software will display a testing screen 210 with a testing symbol 212 one contrast differential level lower than the immediately preceding testing symbol 212.

Generally, testing software 100 will start each phase of the test process by displaying a testing screen 210 with a testing symbol 212 of a higher contrast differential with testing field 211. Upon registering a predetermined number of correct identifications of testing symbols 212, testing software 100 will begin displaying a series of testing screens 210 with testing symbols 212 of a lower contrast differential with testing field 211. Upon registering a predetermined number of incorrect identifications, or selections of pass button 214, or lapses of the predetermined amount of time, testing software 100 will begin displaying a series of testing screens 210 with testing symbols 212 of a higher contrast differential with testing field 211. The testing process in a specific color phase will end after a predetermined number of correct identifications are registered at a specific contrast differential level. Registering a large number of correct identifications at a specific contrast differential level indicates that the patient cannot reliably distinguish and identify a testing symbol 212 of lower contrast differential levels. The testing process in a specific color phase may also end after pass button 214 has been selected a predetermined number of times. Repeatedly selecting pass button 214 indicates that the patient can no longer reliably distinguish and identify the series of testing symbols 212 that are being displayed.

Figure 9:
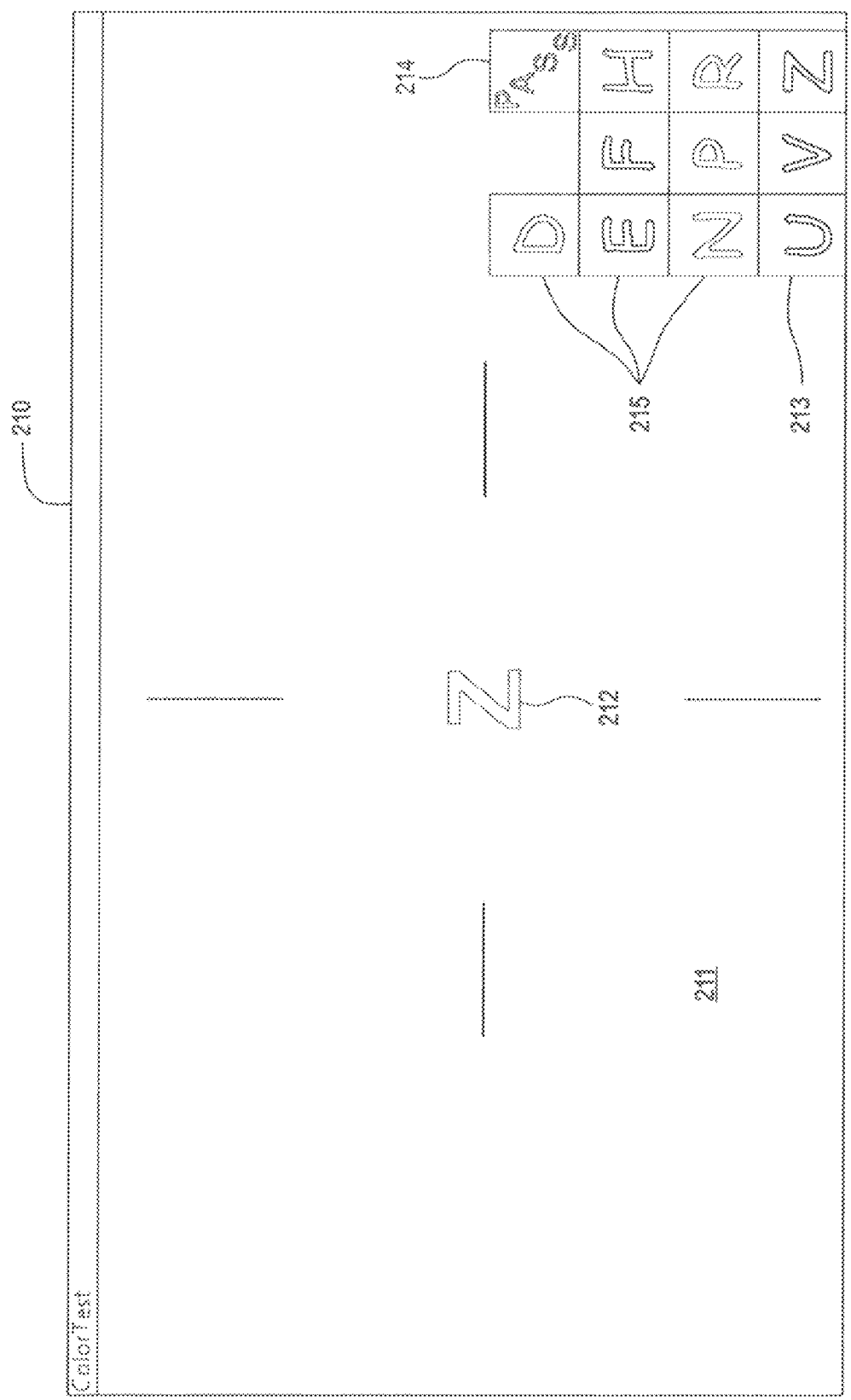
FIG. 9 is a screen shot of an inventive aspect.

FIG. 9 shows refreshed testing screen 210 comprising testing field 211, testing symbol 212 of reduced contrast differential with testing field 211, response table 213, and pass button 214. Response table 213 comprises plurality of response symbols 215. The patient taking the CCT will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Figure 10:
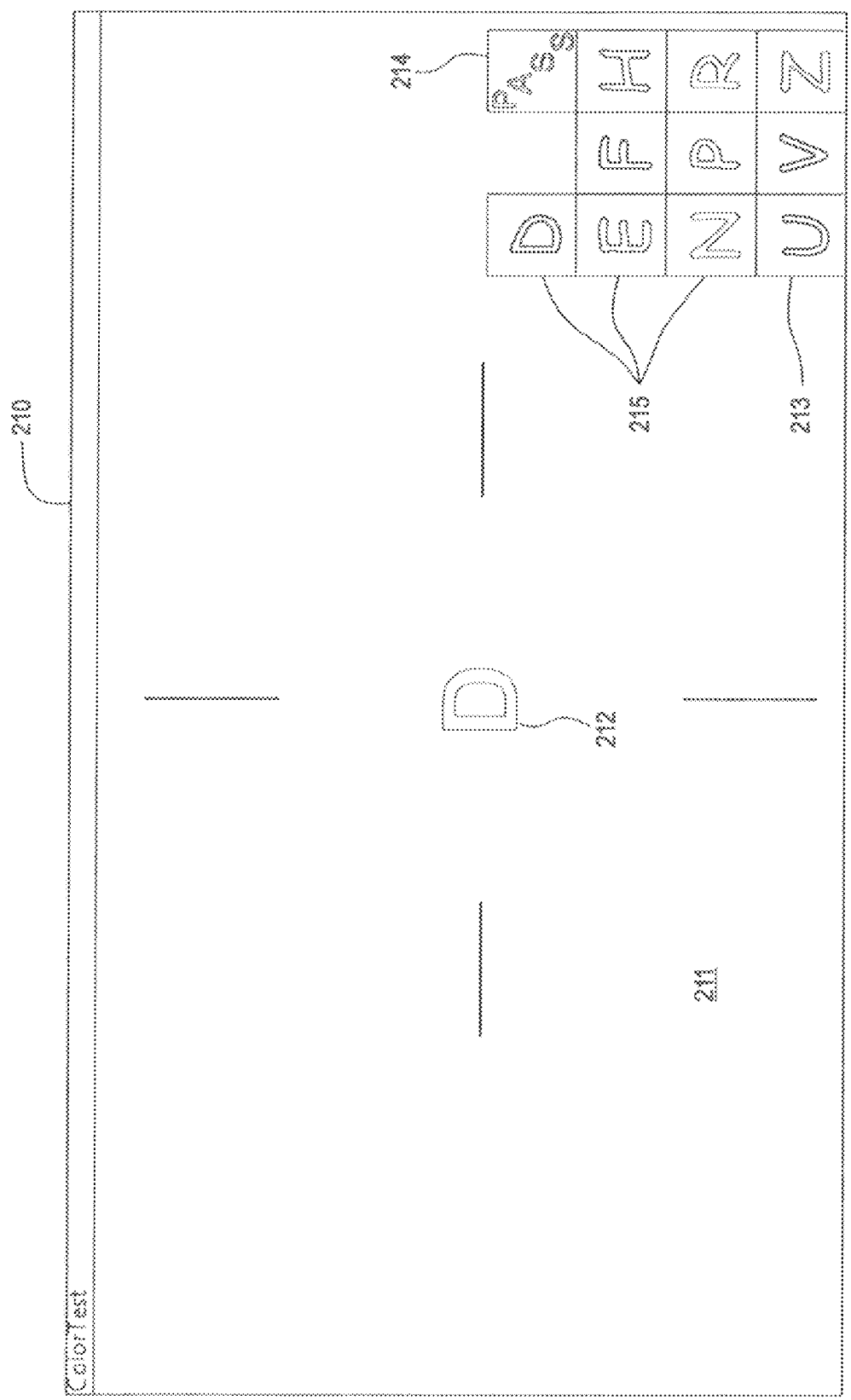
FIG. 10 is a screen shot of an inventive aspect.

FIG. 10 shows refreshed testing screen 210 comprising testing field 211, testing symbol 212 of further reduced color contrast differential with testing field 211, response table 213, and pass button 214. Response table 213 comprises plurality of response symbols 215. The patient taking the CCT will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Figure 11:
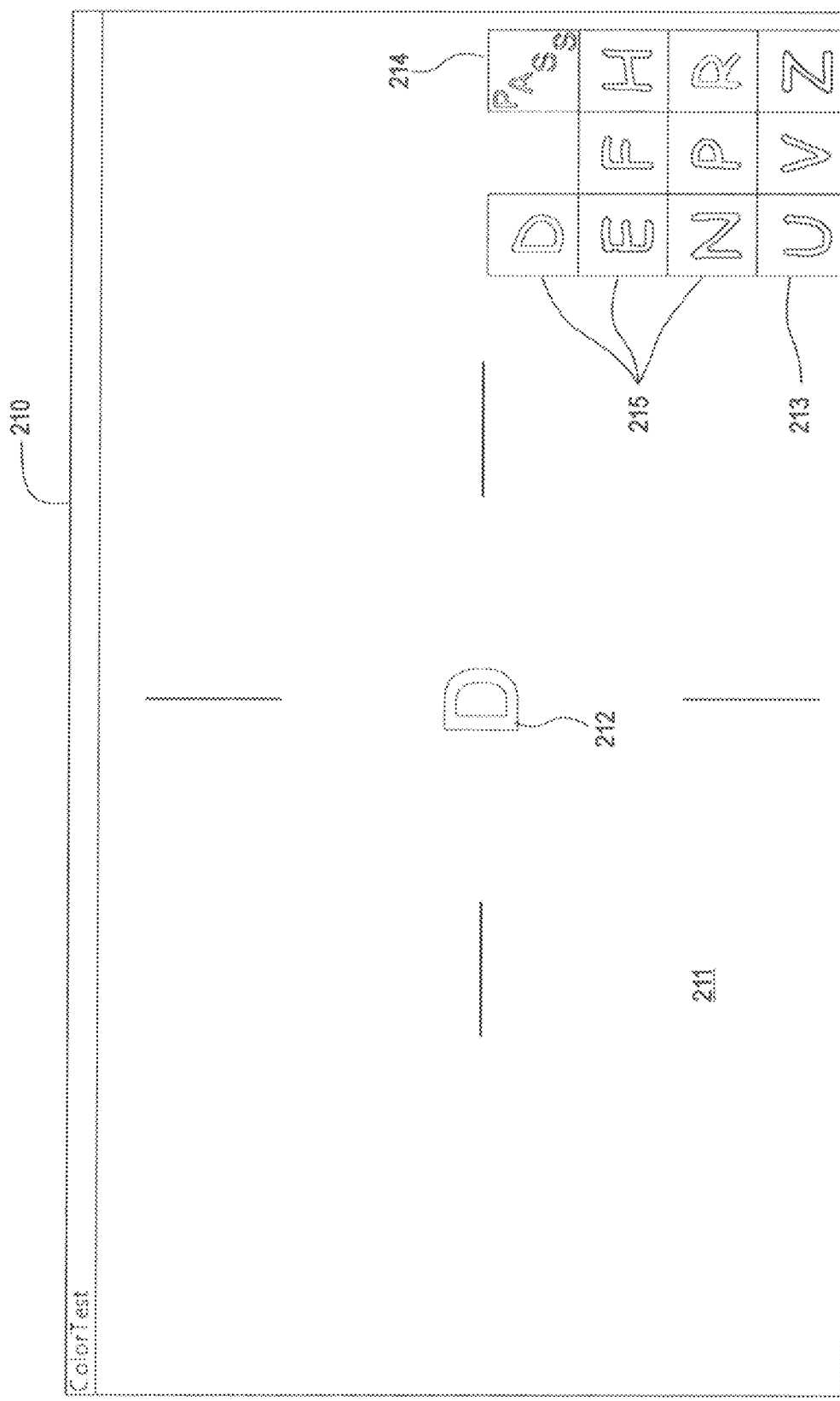
FIG. 11 is a screen shot of an inventive aspect.

FIG. 11 shows refreshed testing screen 210 comprising testing field 211, testing symbol 212 of even further reduced color contrast differential with testing field 211, response table 213, and pass button 214. Response table 213 comprises plurality of response symbols 215. The patient taking the CCT will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Figure 12:
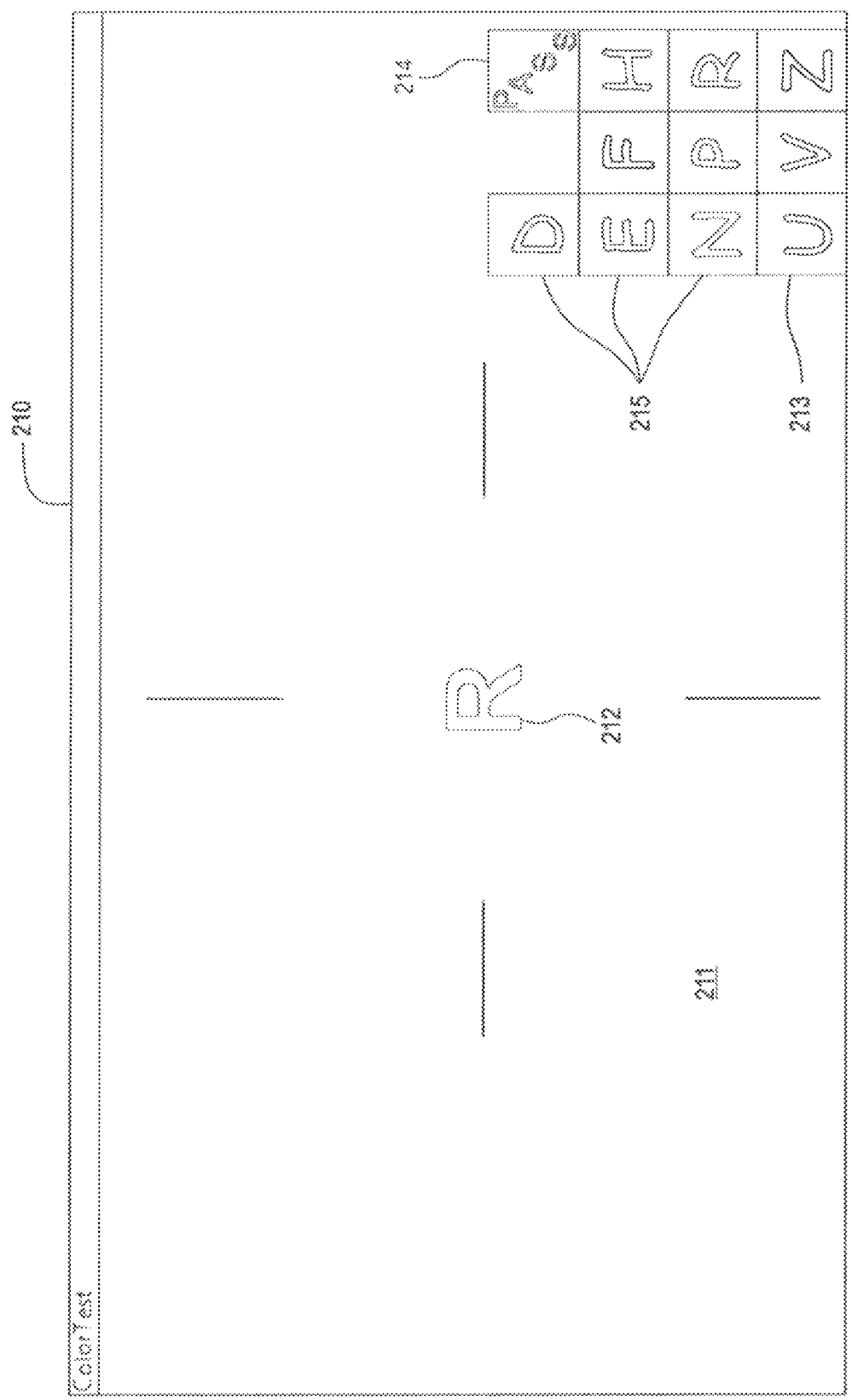
FIG. 12 is a screen shot of an inventive aspect.

FIG. 12 shows refreshed testing screen 210 comprising testing field 211, testing symbol 212 of minimal color contrast differential with testing field 211, response table 213, and pass button 214. Response table 213 comprises plurality of response symbols 215. The patient taking the CCT will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Upon completion of a specific color phase in the testing process, testing software 100 will continue to the next color phase for the currently tested eye. If all color phases have been completed for the currently tested eye, testing software 100 will display eye selection screen 232 and continue the testing process with the next eye to be tested. If all color phases for both eyes have been completed, the test process is complete.

Figure 13:
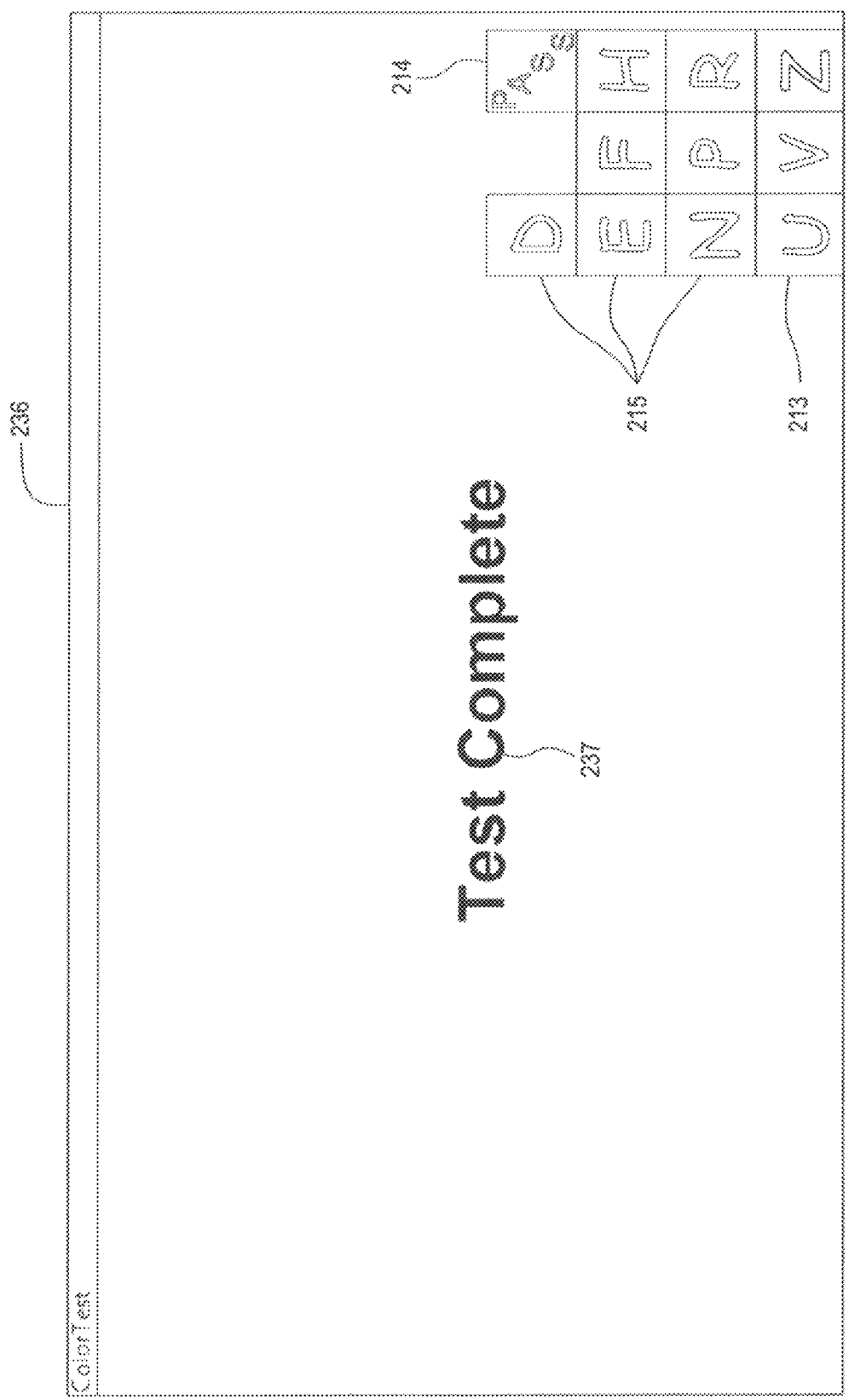
FIG. 13 is a screen shot of an inventive aspect.

FIG. 13 shows test conclusion screen 236. Test conclusion screen 236 comprises conclusion message 237, response table 213, and pass button 214. Conclusion message 237 informs the patient that the test process is complete. Although response table 213 and pass button 214 are components of test commencement screen 230, they are not active, i.e., they cannot be selected.

Alternately, the CCT test may be performed as a low cone contrast screening test. A separate cone contrast screening mode allows for the quick determination of whether a patient has decreased color vision and should be monitored with the full CCT test. The cone contrast screening mode presents only a limited number, for example, a single line, of cone contrast levels. Letter presentation times are the same as the CCT test.

The specific cone contrast level presented is based on the cone contrast threshold of patients with normal vision. If the patient is unable to see the letters at this cone contrast level, the test results as considered abnormal. The CCT Screening report will display the lowest cone contrast level the patient is able to see for each cone type per eye and whether the results are "Normal" or "Abnormal Cone Contrast Vision". If the patient has Abnormal Cone Contrast Vision, the report will include a recommendation that the patient be monitored with the full CCT test. In an example embodiment, the cone contrast screening test presents only blue characters to determine whether the patient taking the test has normal or abnormal cone contrast vision based on blue cone function.

Changes in color vision may be able to detect pre-pathology changes in the retina, such as reduced macular pigment density. Thinning of the macular pigment has been linked with pre-AMD and may be slowed or reduced by nutraceuticals. In commencing the CCT test by displaying the lowest cone contrast level below human threshold and conducting the CCT test by measuring in small increments around this threshold, it is possible to detect pre-pathology changes in the patient's vision.

Viewing and Interpreting Results

Figure 19:
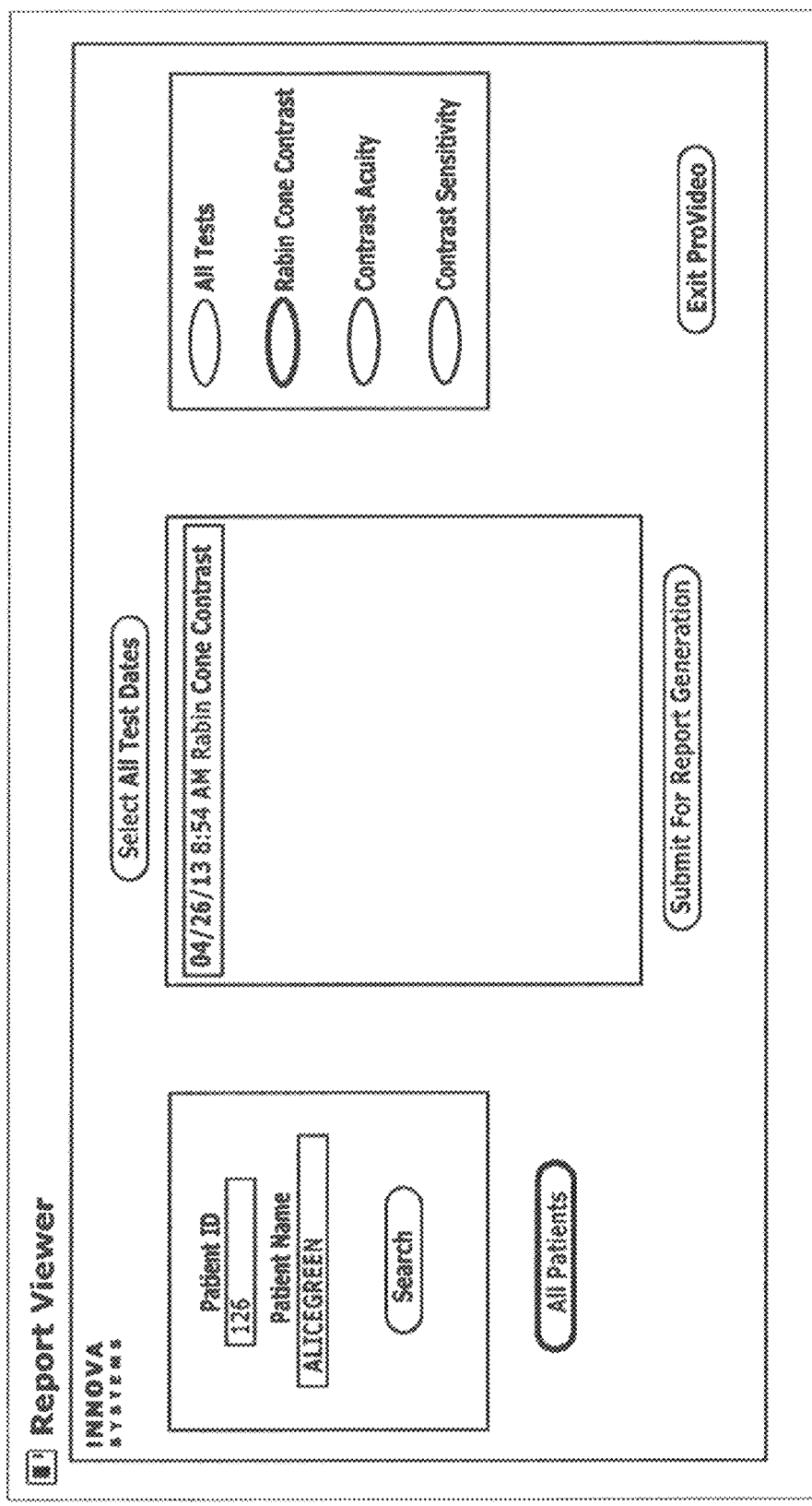
FIG. 19 is a screen shot of an inventive aspect.
Figure 21:
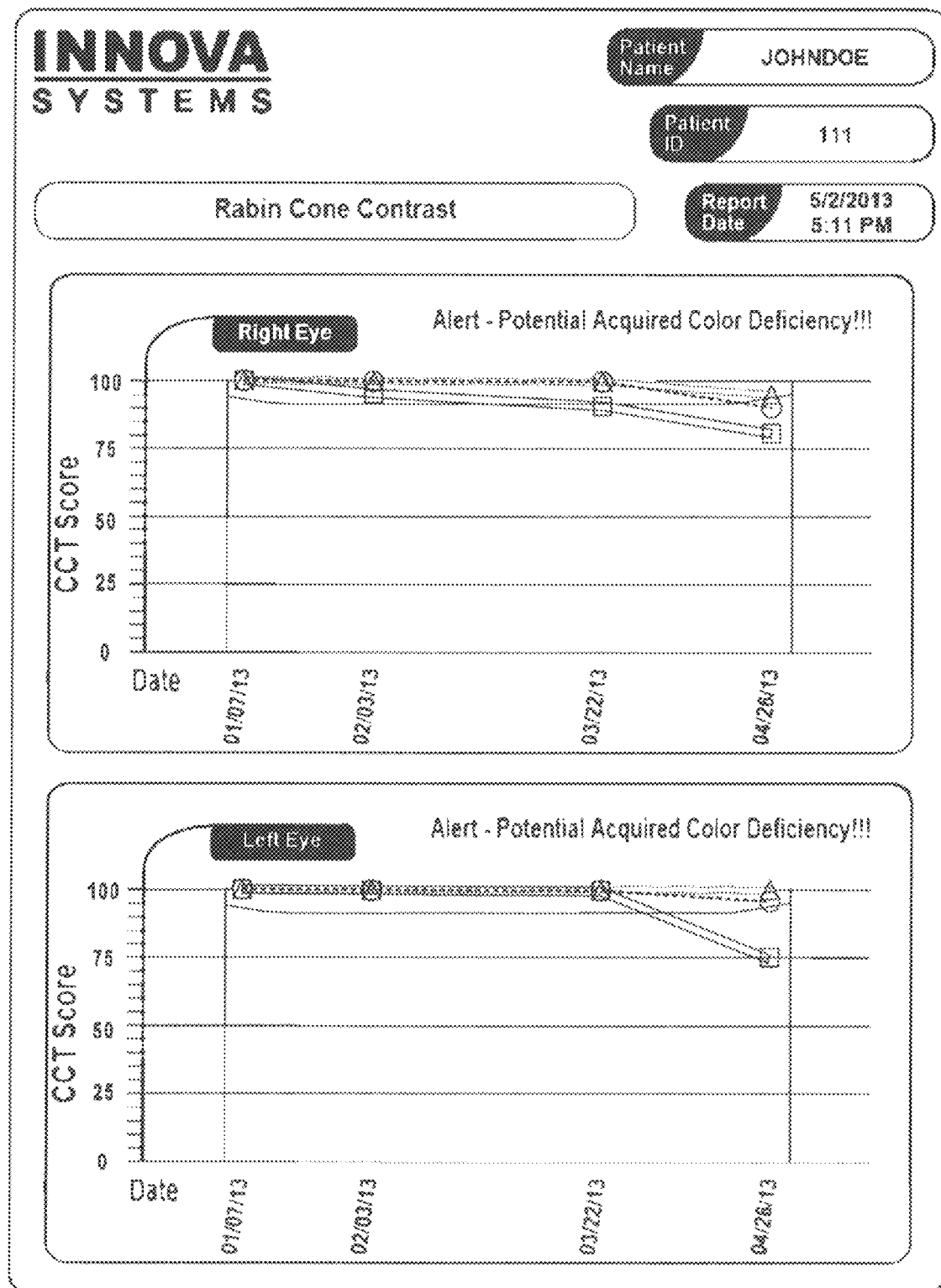
FIG. 21 is a report of an inventive aspect.
Figure 22:
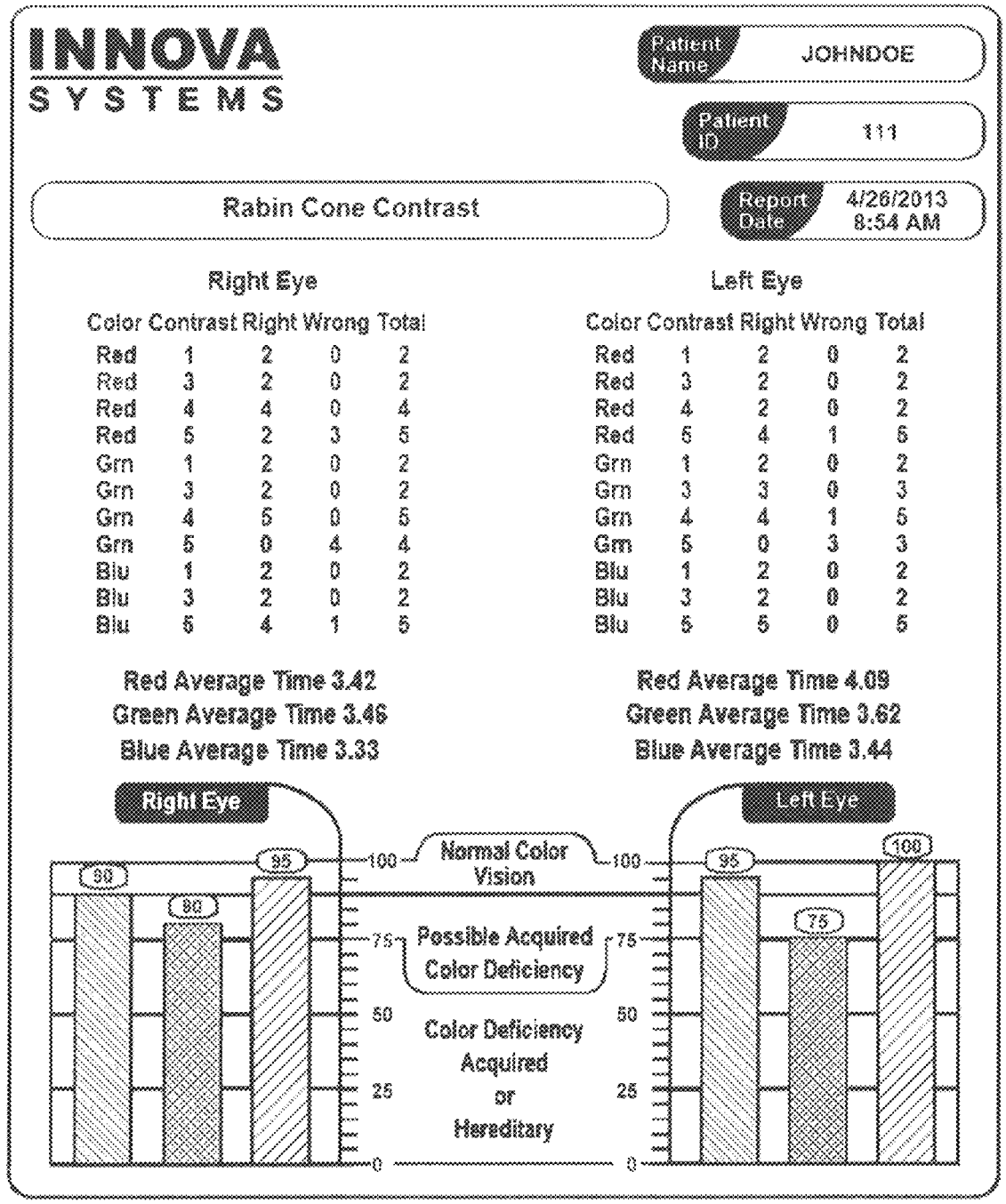
FIG. 22 is a report of an inventive aspect.
Figure 23:
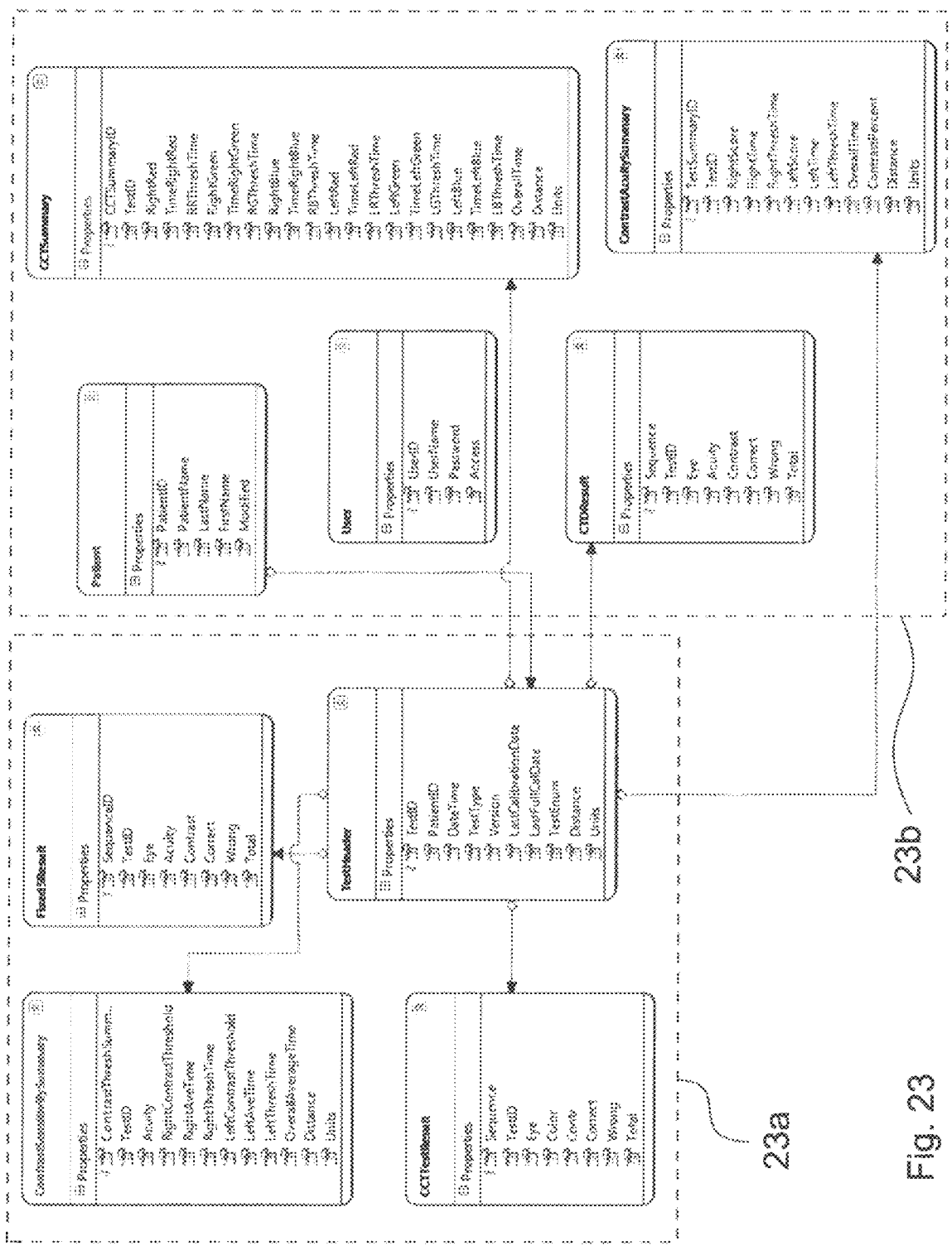
FIG. 23 is a diagram of an inventive aspect.
Figure 23A:
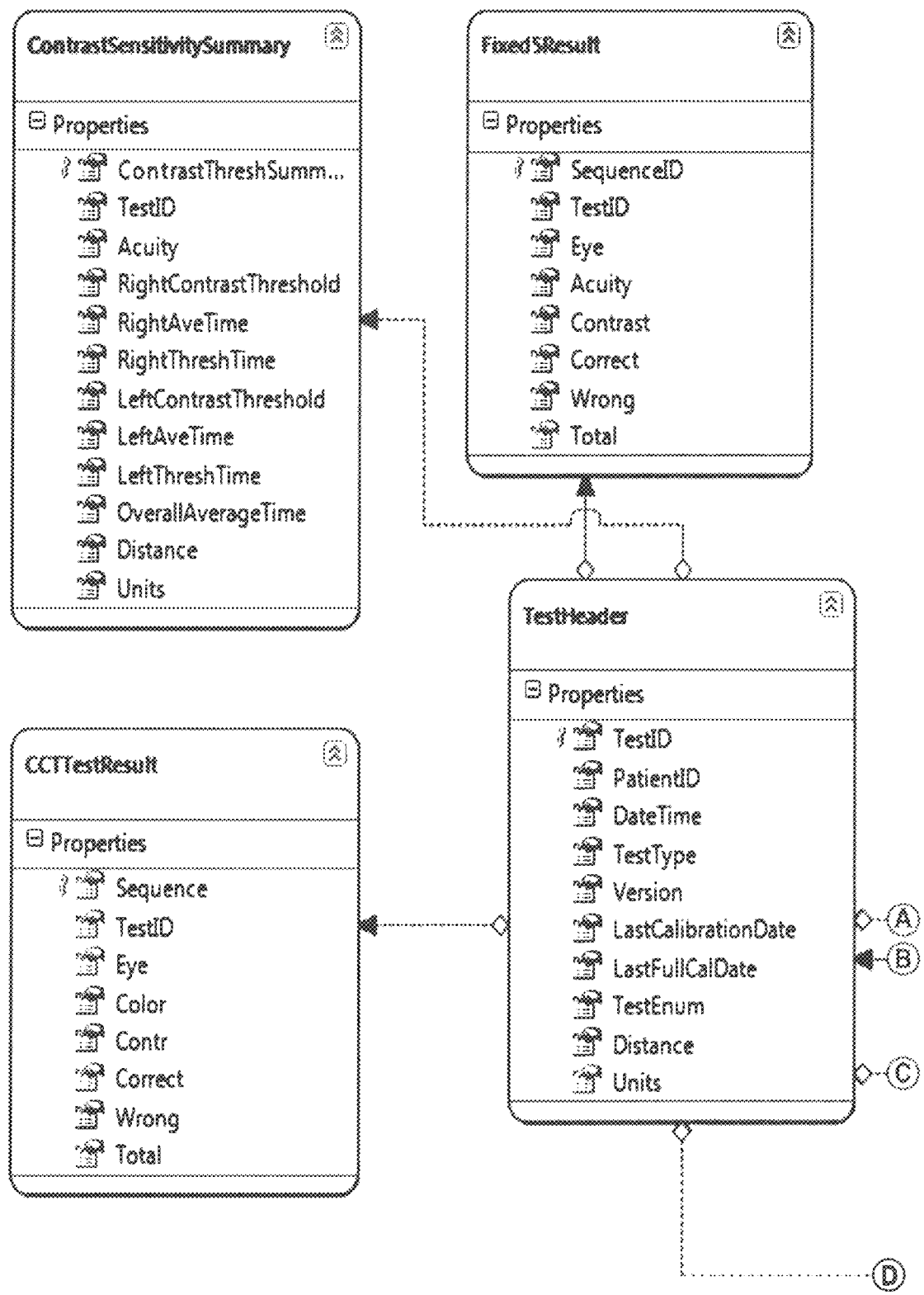
FIG. 23a is a diagram of an inventive aspect.
Figure 23B:
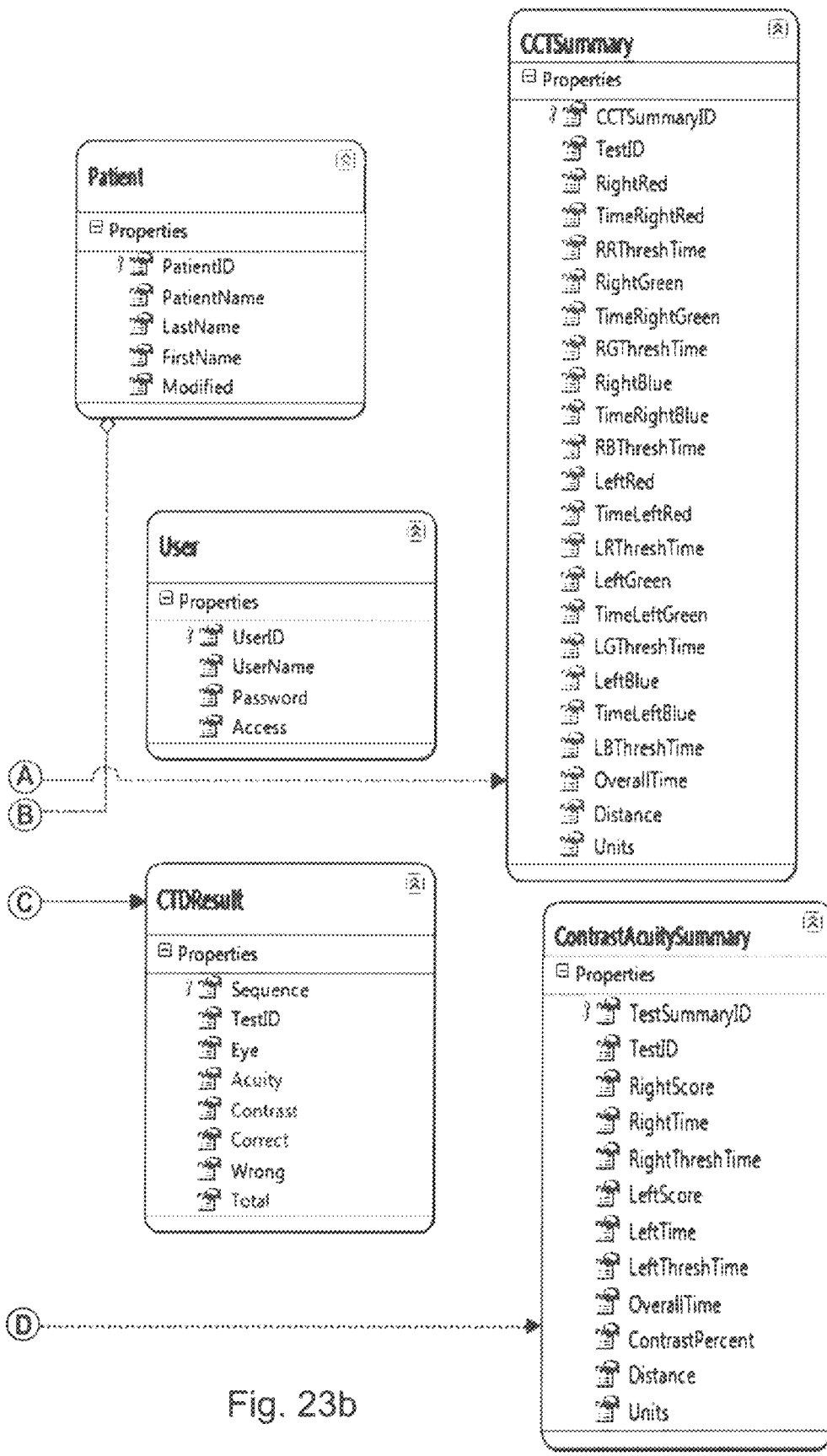
FIG. 23b is a diagram of an inventive aspect.
Figure 24:
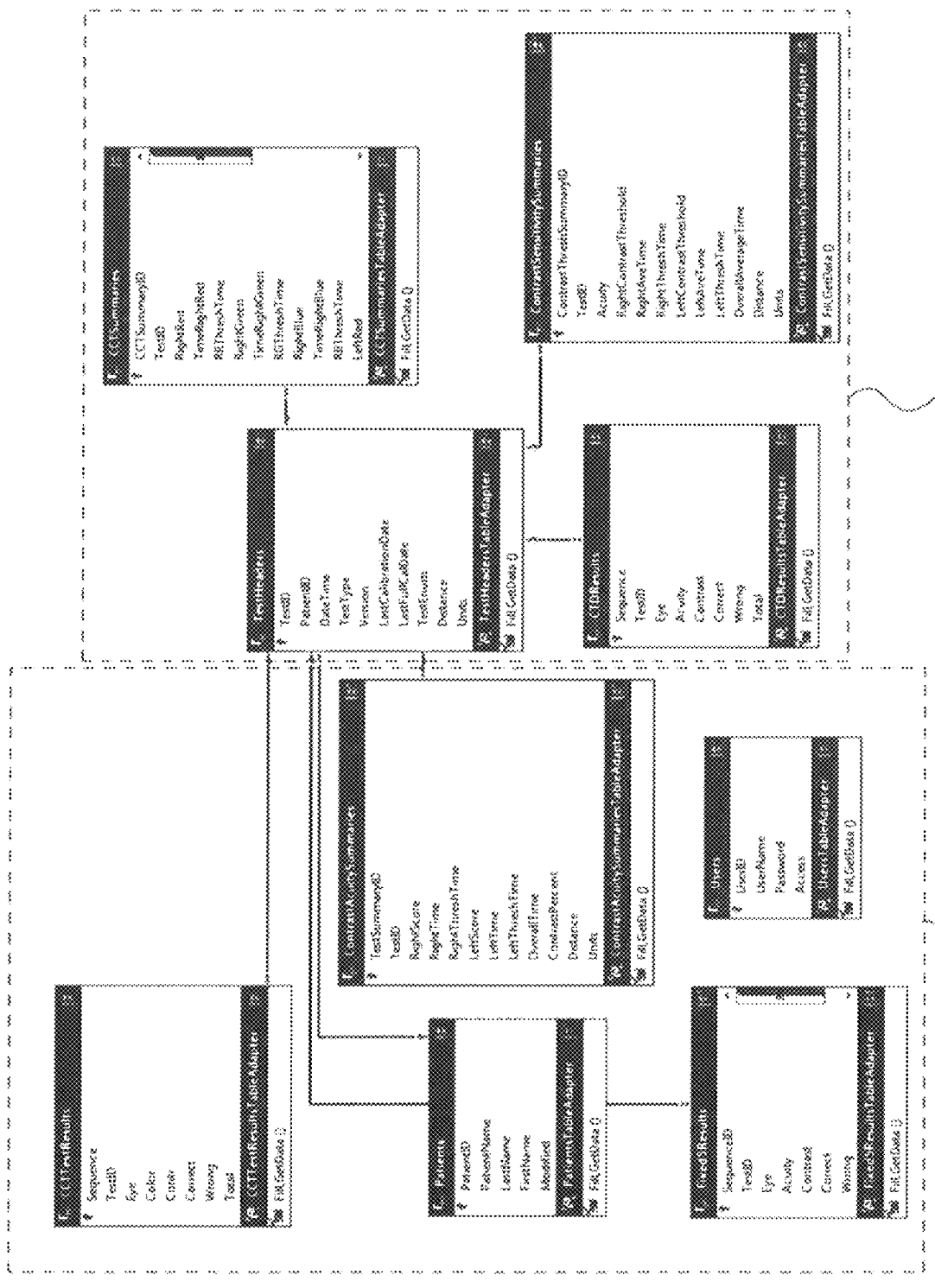
FIG. 24 is a diagram of an inventive aspect.
Figure 24A:
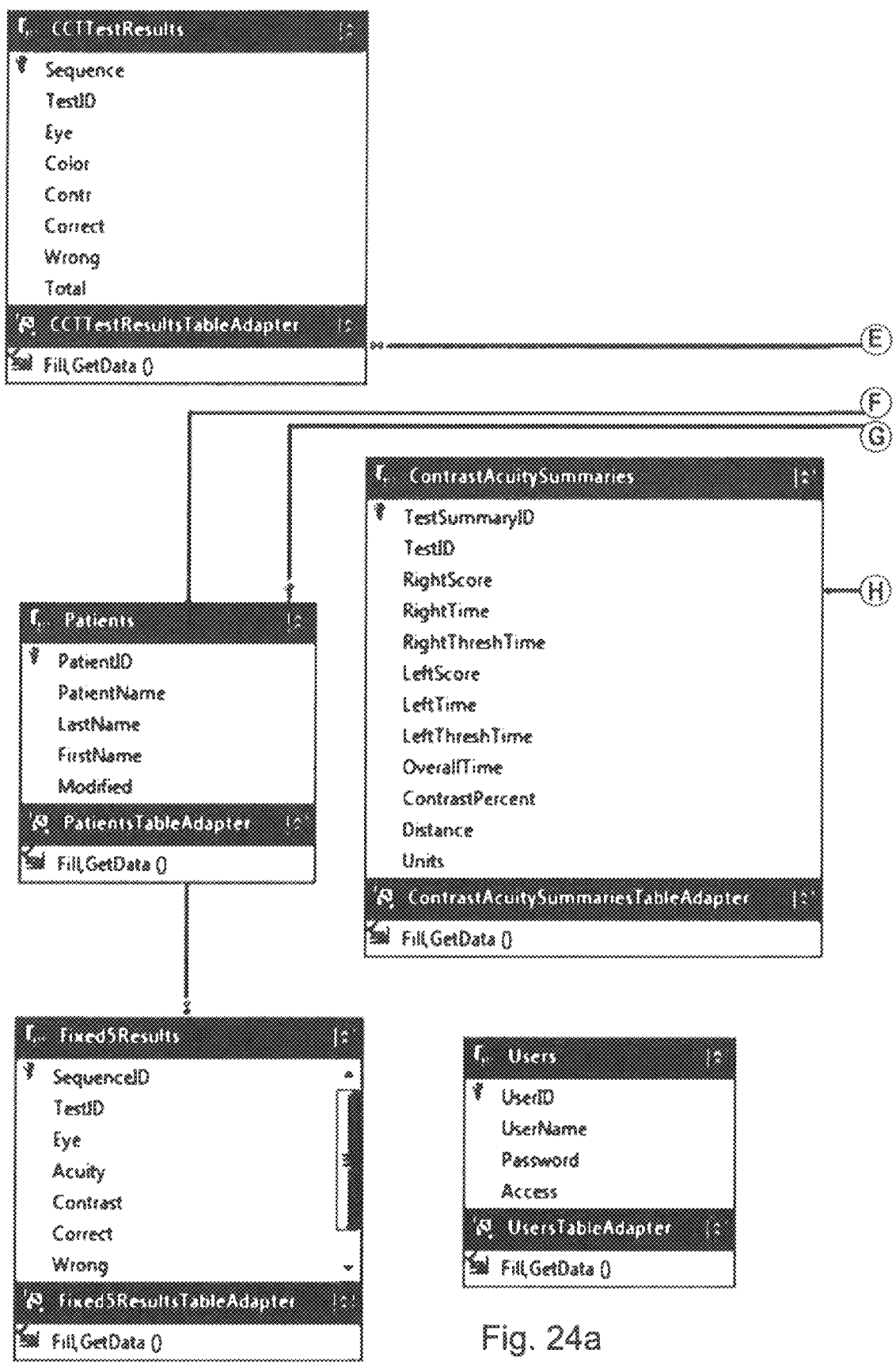
FIG. 24a is a diagram of an inventive aspect.
Figure 24B:
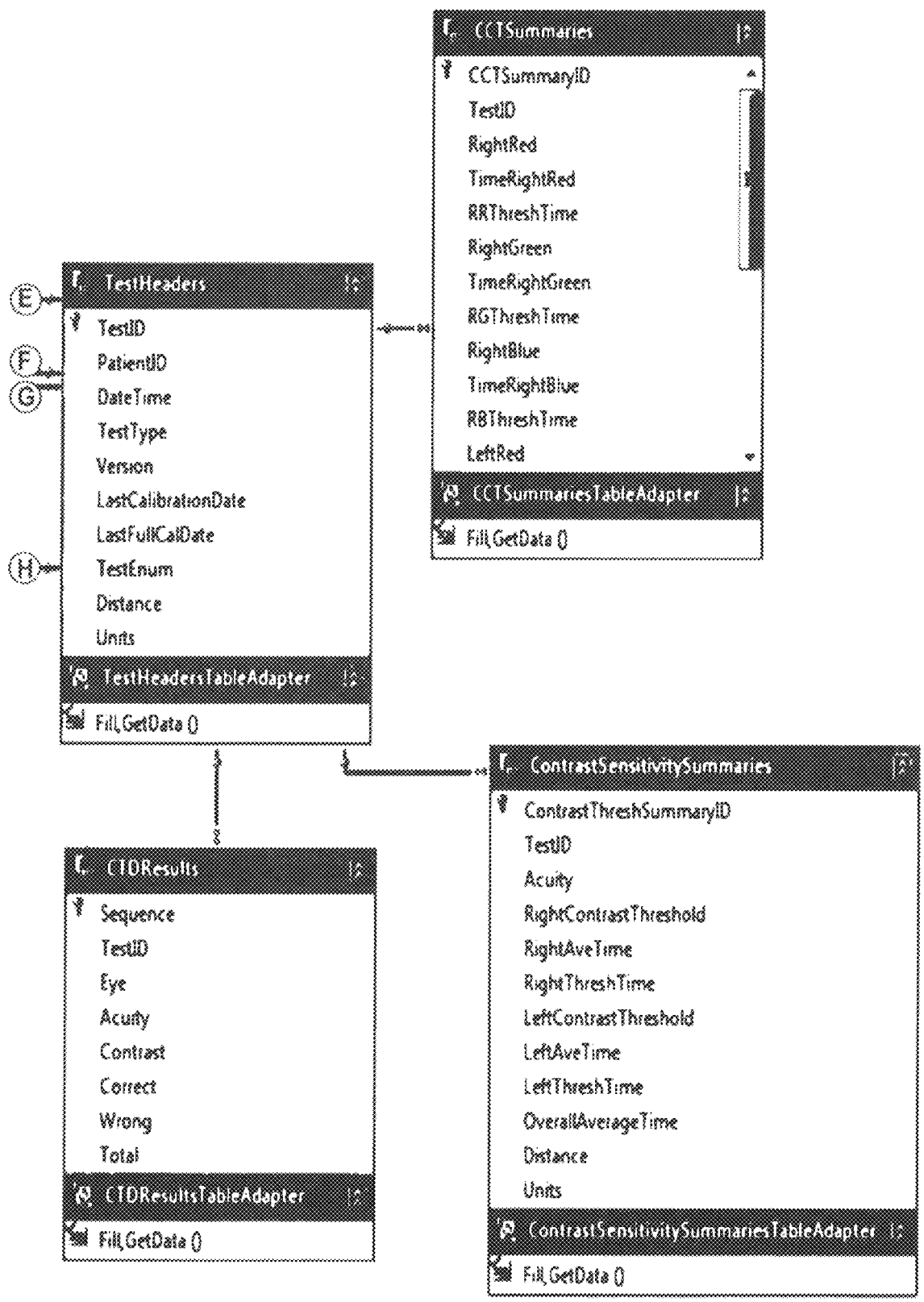
FIG. 24b is a diagram of an inventive aspect.

Reports may be generated by patient, type of report, and dates. To generate a report for a particular patient, testing software 100 is arranged to select data connected to a patient ID. You may display a list of all tests for a patient as shown in FIG. 19. Or, to print Comparison Reports, select the type of report to be displayed, and then select the date range for the report. Use the mouse or TAB key to move between the types of reports. Double click or hit ENTER on the specific report date to view specific exam results. Selecting Dates for Comparison Reports to view comparison results select the date range to be displayed. To display reports within a narrower time frame, for example, since the beginning of treatment, you may select a subset of the available tests. Hold down the SHIFT key to select a date range or hold down the CTRL key to select specific tests. Use the PgUp and PgDn buttons to select larger date ranges. When the desired test dates are selected, click or TAB to the Submit for Report Generation button to view the report.

Figure 14:
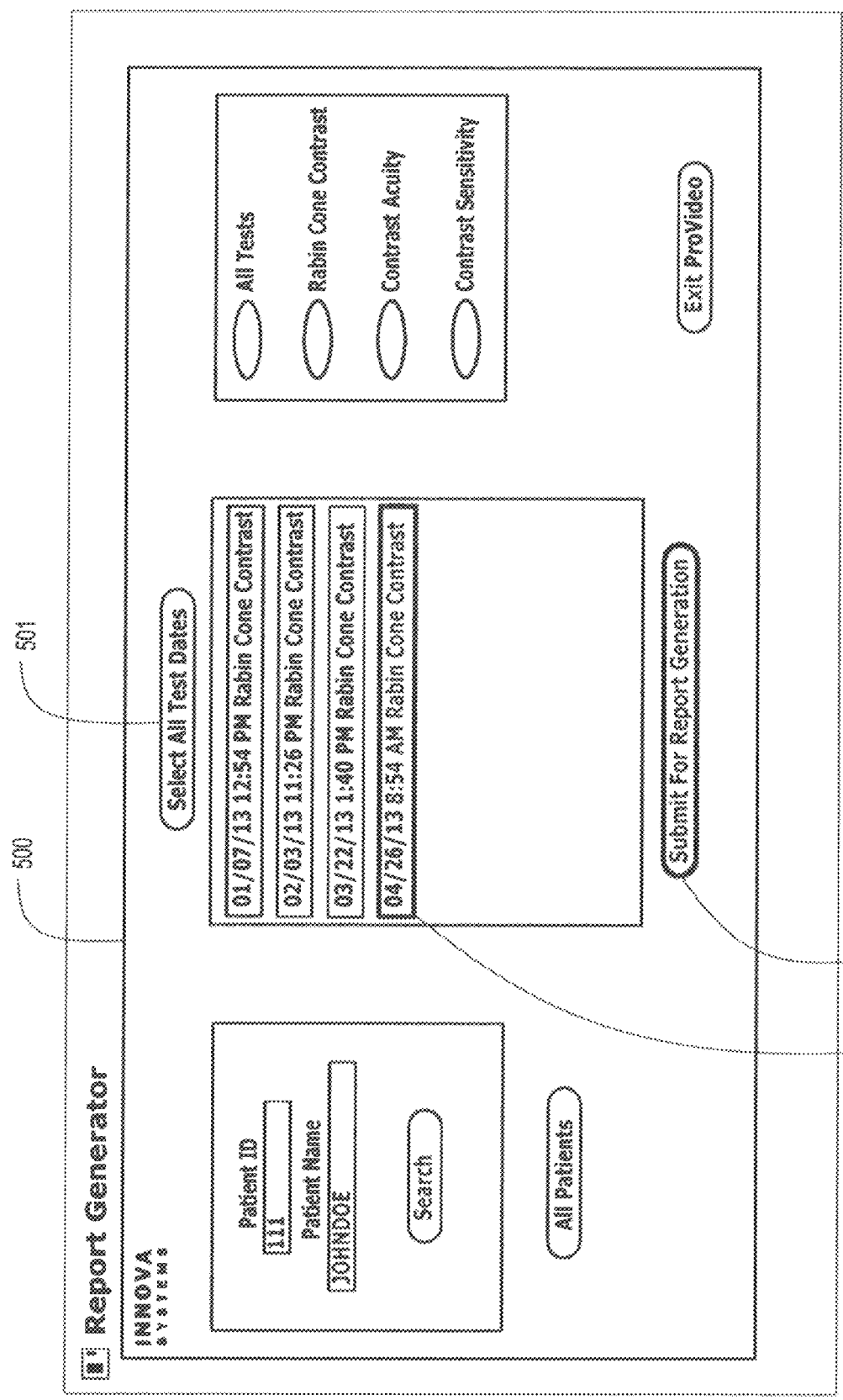
FIG. 14 is a screen shot of an inventive aspect.
Figure 15:
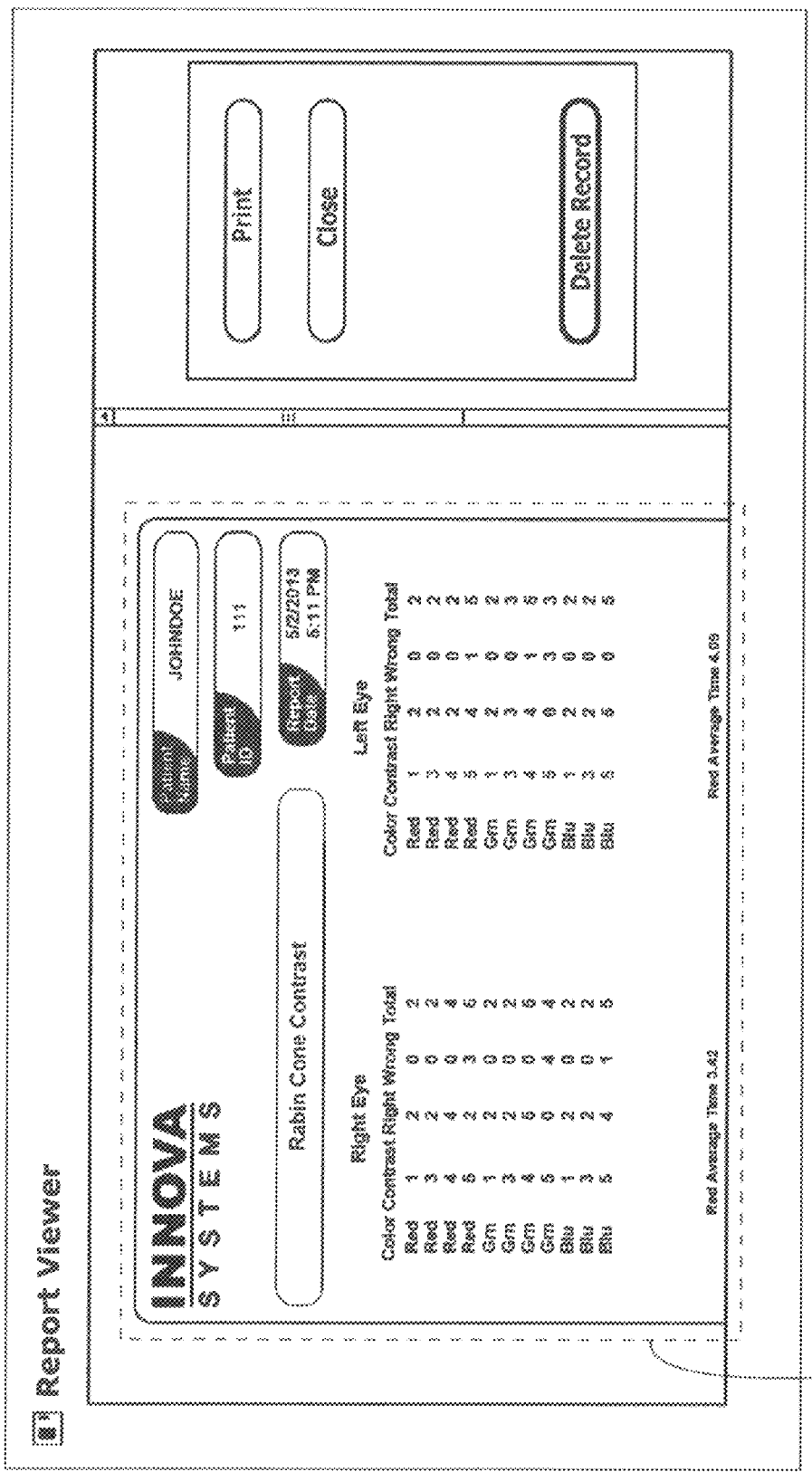
FIG. 15 is a report of an inventive aspect.
Figure 15A:
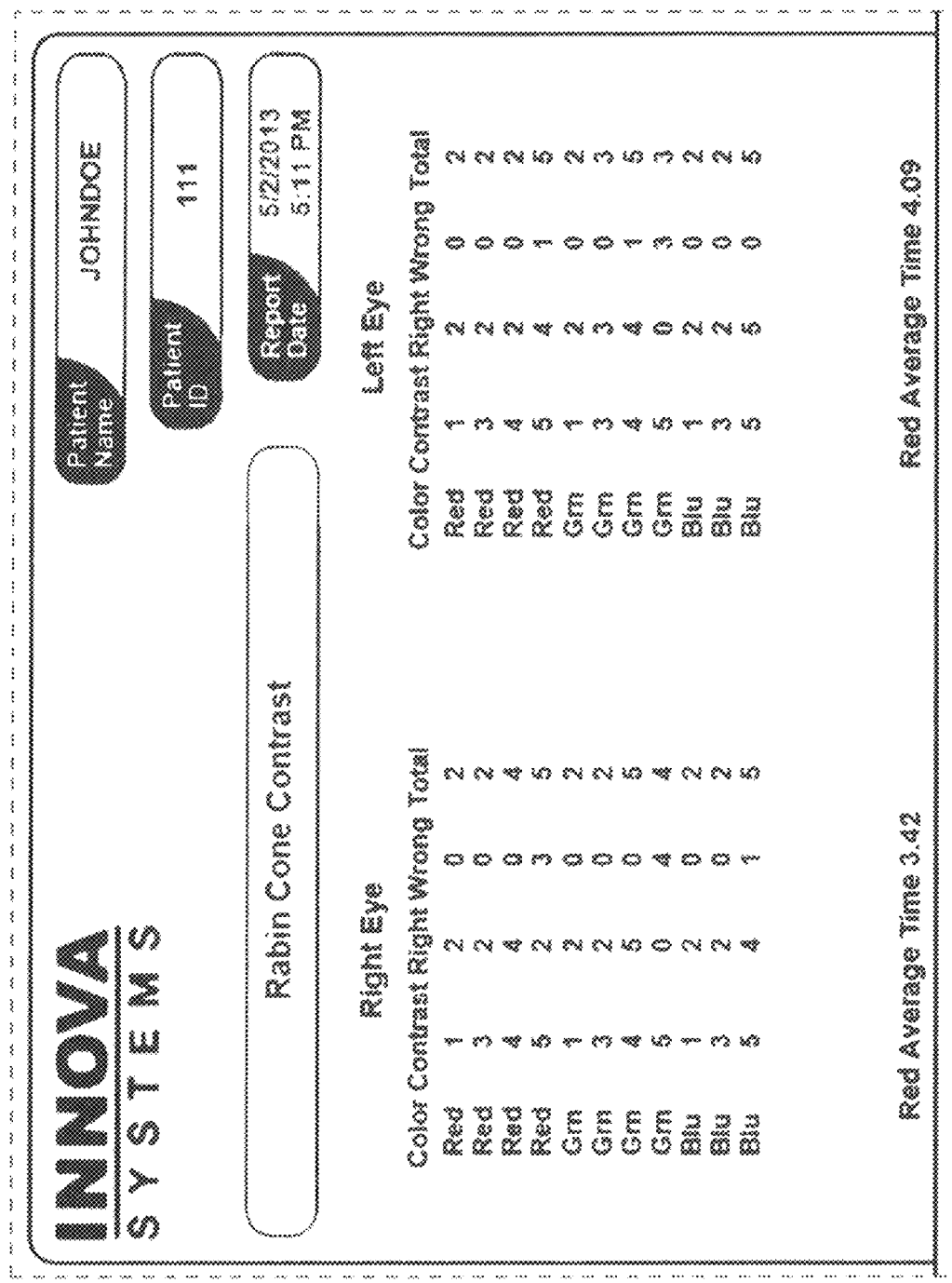
FIG. 15a is a report of an inventive aspect.
Figure 16:
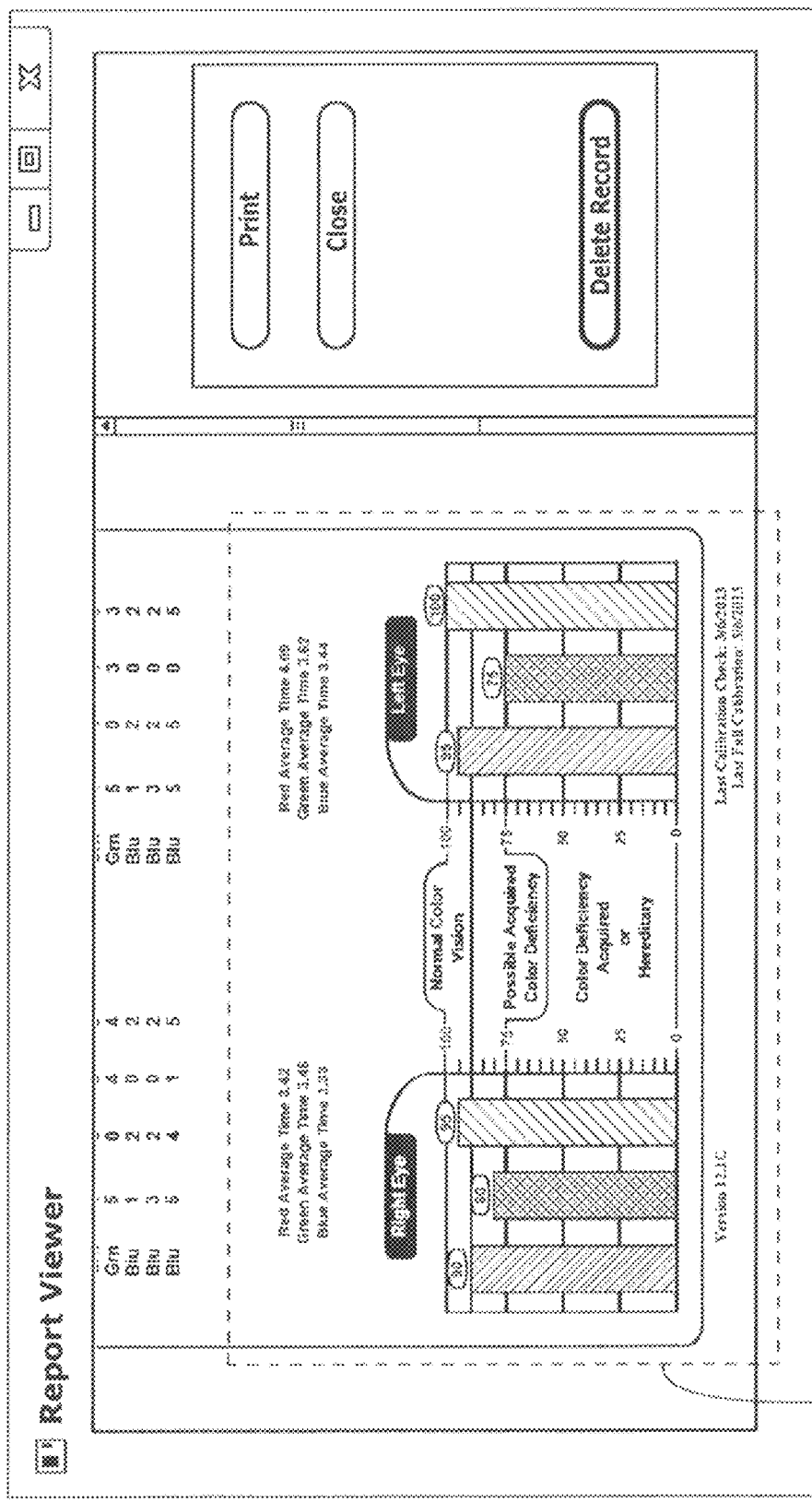
FIG. 16 is a report of an inventive aspect.
Figure 16A:
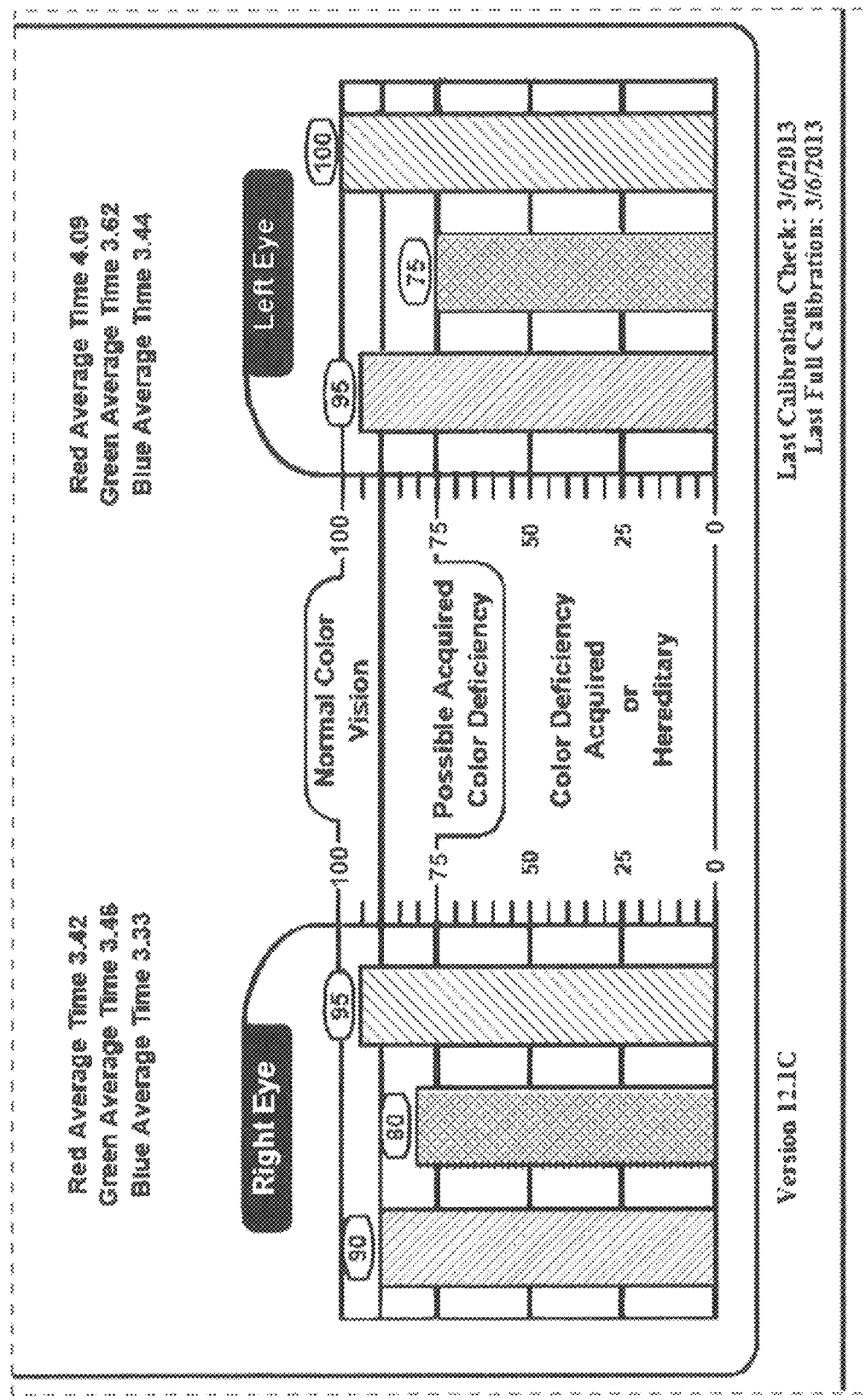
FIG. 16a is a report of an inventive aspect.

Reports button 113 shown in FIG. 2 can be accessed to review and generate test results. Similarly, FIG. 14 shows report generator screen 500. Report generator screen 500 comprises select all test dates button 501 and submit for report generation button 502. If select all test dates button 501 is selected, testing software 100 is directed to include all test data in generating reports for interpretation. If select all test dates button 501 is not selected, particular test dates can be selected from report generator screen 500. Once particular test dates are selected from report generator screen 500, for example, selected test date 503, selection of submit for report generation button 502 directs testing software 100 to generate reports.

Figure 17:
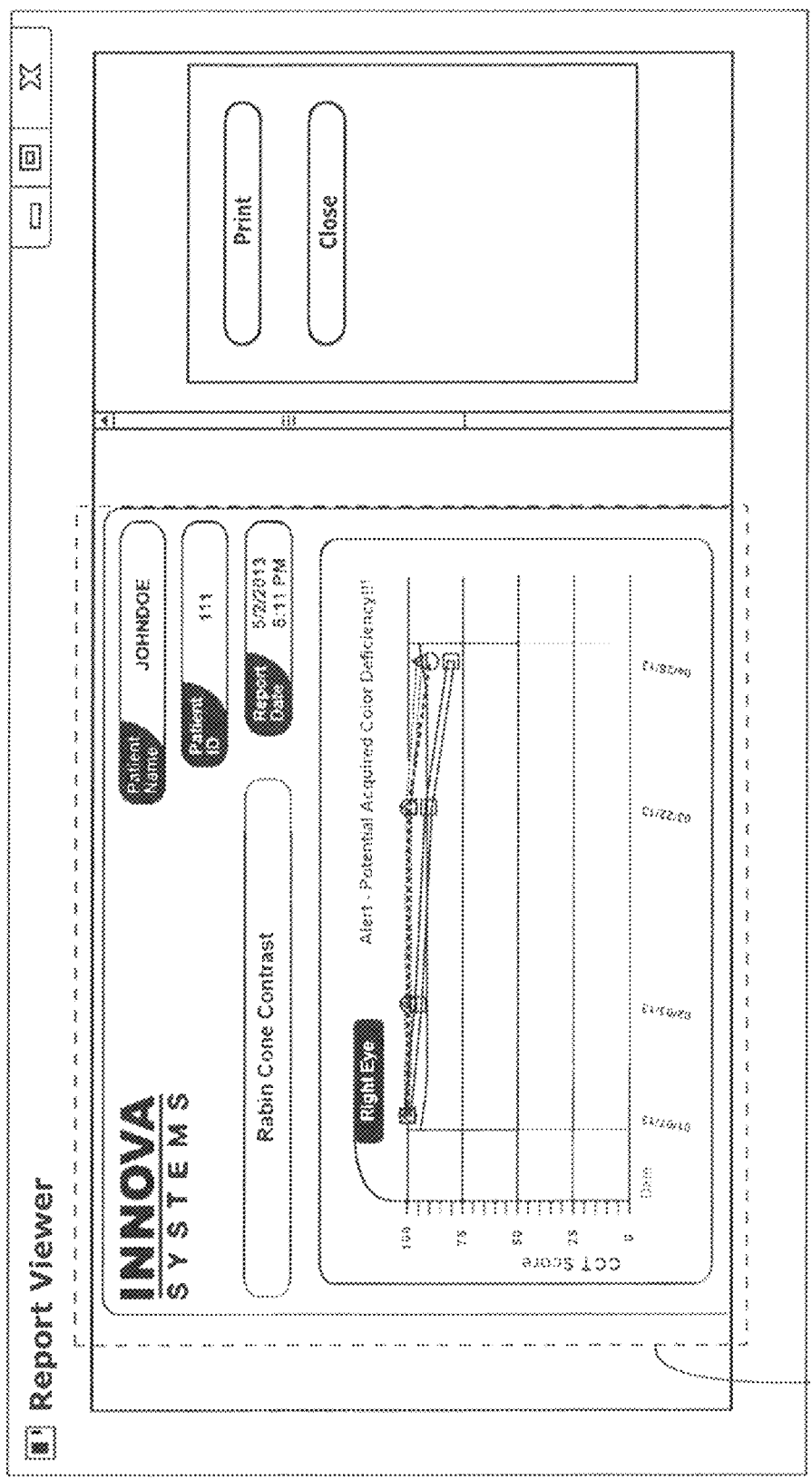
FIG. 17 is a report of an inventive aspect.
Figure 17A:
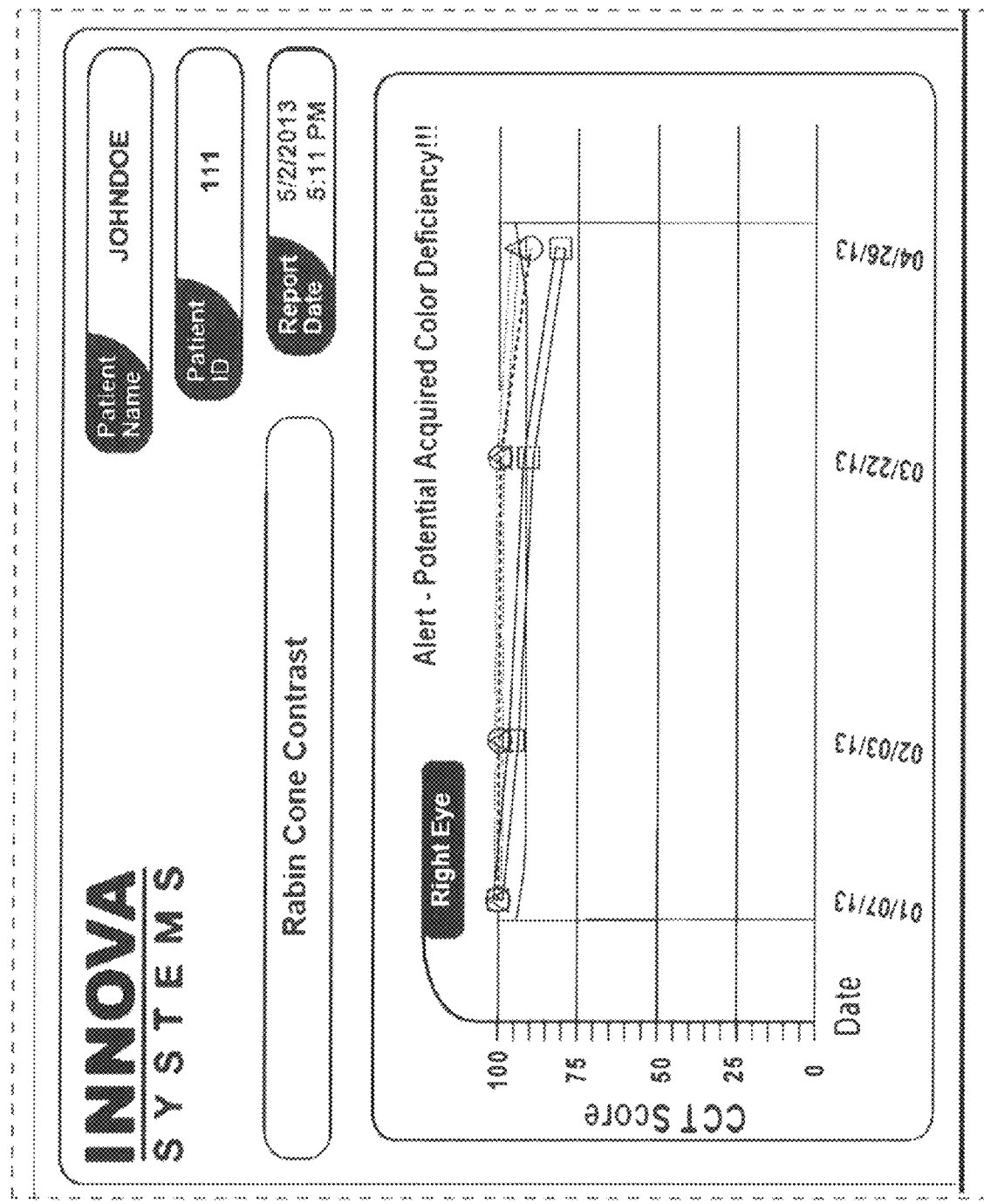
FIG. 17a is a report of an inventive aspect.
Figure 18:
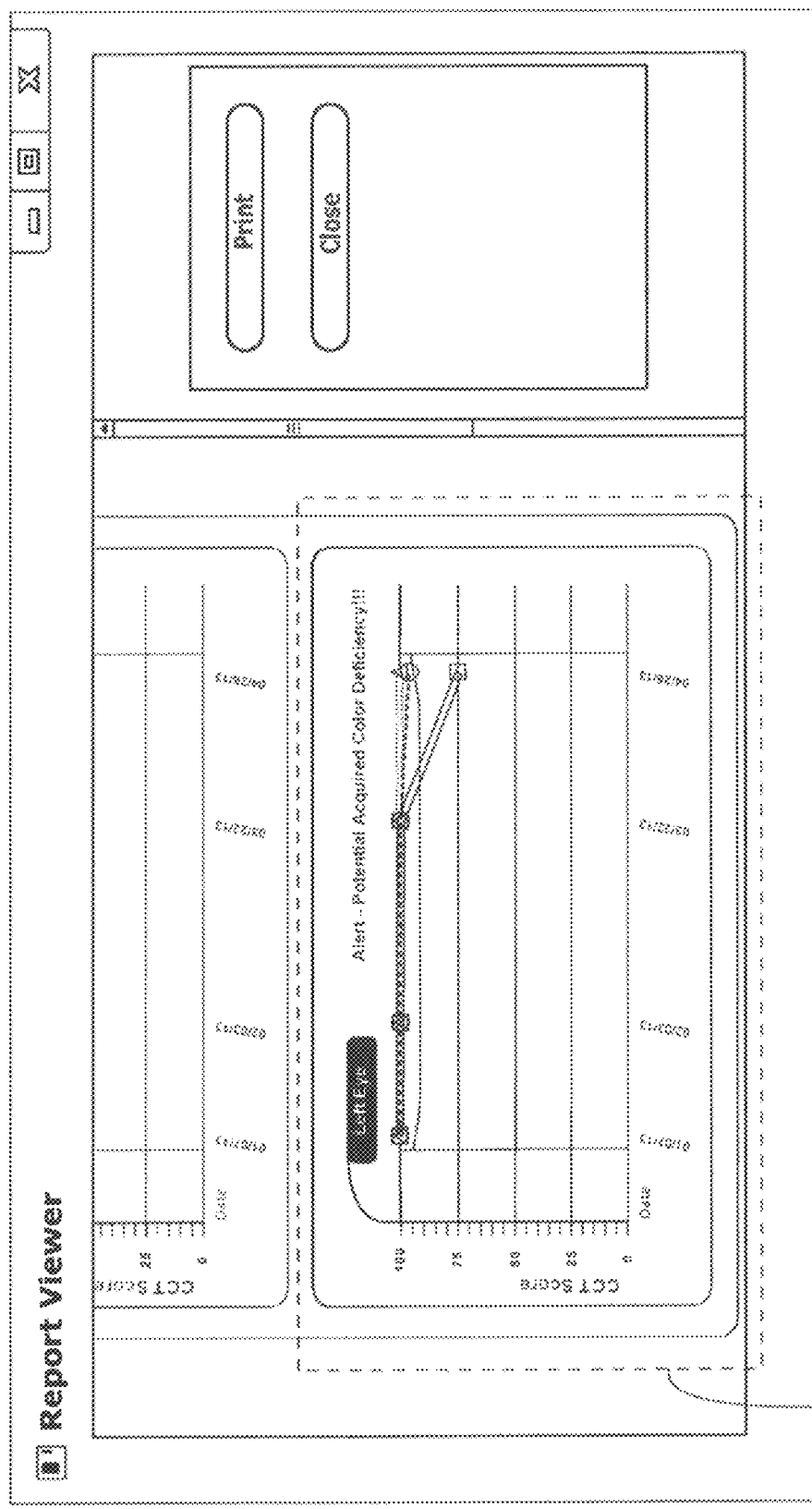
FIG. 18 is a report of an inventive aspect.
Figure 18A:
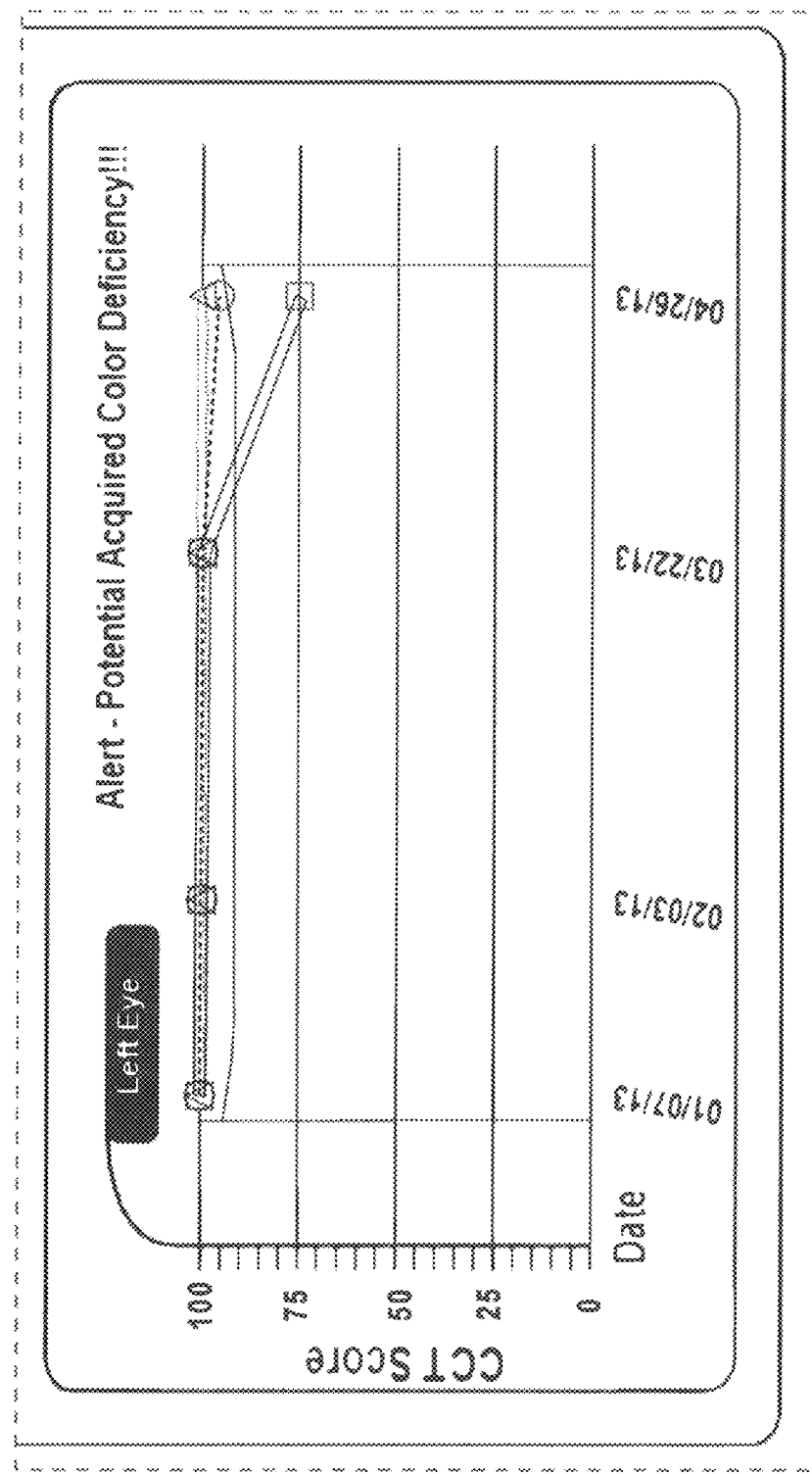
FIG. 18a is a report of an inventive aspect.

Reports are shown in FIGS. 15-18, 21-22. Significantly, CCT scores are shown in red, green and blue. Red CCT scores are shown with a single dashed line connecting circles. Green CCT scores are shown as a bar connecting squares. Blue CCT scores are shown as a double dashed line connecting triangles. The circles, squares and triangles refer to CCT scores. The lines connecting the CCT scores are generated to show trends and whether a patient's color vision is deteriorating. Some reports include bar graphs (FIG. 16) and line graphs (FIG. 17). The colors red, yellow and green are also used to indicate color deficiency, possible deficiency, and normal vision, respectively.

In an example embodiment, the test results, namely, the degree of cone sensitivity loss, are stored in an electronic health record (EHR) associated with the patient. An interface to EHR transfers patient test results from the CCT database to the EHR database. An interface from the computer systems implementing the CCT test to the computer systems storing EHR data ensures that all patient records are stored in a single location. Unlike the central network database and central cloud database which transfers CCT data to a central CCT database, the EHR interface transfers CCT data to an EHR database, allowing CCT data to be stored along with the patient's other medical records. The EHR interface is a one-way interface moving data only from the CCT database to the EHR database. An interface to EHR incorporates the transfer of individual test reports in a format such as .pdf, individual test scores, or both. For each test, the EHR interface transfers the patient's CCT test resulting including: patient name, test comments, red cone contrast score left eye, green cone contrast score left eye, blue cone contrast score left eye, red cone contrast score right eye, green cone contrast score right eye, and blue cone contrast score right eye.

The EHR interface is complementary to the integration of multiple CCT Devices over a computer network. Without the ability to store test data on the local CCT device or ensure it is accessible on the local CCT device, such as transferring it over the Internet or from a cloud of computers, progression analysis reports, a key component for patient management, would not be available.

In an example embodiment, at the conclusion of the patient test, the information is stored in a temporary EHR upload file. Upon the next sync function, all records in the temporary EHR upload file are transferred to the EHR. A DICOM interface is a standardized information format for patient records transfer. Transfer of data can be made directly to a specific EHR database or to EHR collection software, such as the MHS GENESIS® product used by the United States Department of Defense Military Health System.

Acquired and hereditary color deficiency can be interpreted based on a less than normal cone score in a single visit or as a drop in a specific cone score of more than 10 points from a patient's base-line. Normal color vision is indicated by a CCT score between 90-100. Possible color vision deficiency is indicated by a CCT score between 75-89. Color deficiency, hereditary or acquired, is indicated by a CCT score between 0-74. Acquired and hereditary color deficiency overlap. However, there are several characteristics that can help identify acquired vs. hereditary color deficiency. Hereditary color deficiency is indicated by selective degradation of red or green tests. Moreover, cone sensitivity scores are substantially symmetrical in the left and right eyes. In contrast, acquired color deficiency is not as selective to cone types and may show decreases on red, green and blue tests. Acquired color deficiency also usually features asymmetrical cone sensitivity scores in the left and right eyes as the disease advances at different rates in each eye.

In an example embodiment, a patient's results in the CCT test can be used to create and display a simulated depiction of the patient's vision, so that people with normal vision can perceive how the cone sensitivity loss affects the patient's vision. Patients with decreased visual function often have difficulty communicating the vision loss they experience and how it impacts their daily living. This is especially true when their loss of vision has not yet impacted their visual acuity, i.e., they are 20/20 or near 20/20, but it is affecting their "quality of vision" (e.g., color vision, contrast sensitivity, low luminance vision). Family and caregivers may find it difficult to understand the patient's reduced abilities and may accordingly be unable to accommodate the patient for their abnormal vision. It is important for family or caregivers to better understand how the patient sees in specific situations so they can better aid the patient in these situations.

This simulated cone sensitivity loss is designed specifically for family members or caregivers to "experience" how the patient sees. It consists of a series of images which show the difference between how a normal person sees a particular image and how the patient sees that image. Images depicting normal color vision, normal low luminance vision, normal contrast vision, etc. are first displayed. Each of these images is then altered based on the specific patient's test scores for the color vision test, low luminance test, contrast sensitivity test, contract acuity test, etc. to demonstrate how the specific patient sees the same image(s). A single image may also be altered to combine the impact of the patient's test results from multiple tests into a single image.

In addition to the above, testing equipment, devices and/or methodologies can also be provided for purposes of addressing the problems associated with the use of CCT testing devices and procedures that require individuals to refocus their gaze, identify and select an appropriate character from among a plurality of characters, and/or that utilize letters, numbers, or characters that can be difficult for individuals with low visual acuity to perceive.

Generally, in some aspects a so-called "Forced Choice" type stimulus presentation is implemented wherein a cone-isolating colored stimulus is presented in one of several sections of a display screen and the remaining sections are presented as a grey "background" color. In such procedures, a patient may respond by, for example, touching or clicking on the color stimulus on the display screen in the case of a touchscreen display, using a direction-oriented keypad, or providing a verbal response, i.e., 1st, 2nd, 3rd, 4th quadrant or up, down, left, right, etc., or via the use of eye tracking device and/or software. Other presentations options include multi-section pie shapes, 3-D space, etc. Based on the patient's correct or incorrect response, the color contrast level of the colored stimulus may be decreased or increased. The grey sections can remain constant. The location of the colored stimulus can be deliberate or random and change with each presentation. Testing continues until the patient's threshold for each color is determined and each cone-isolating color (red, green, and blue) is repeated in the same fashion for each eye.

In another aspect, a color contrast stimulus is presented that does not require the recognition of a letter, therefore eliminating several problems associated with a stimulus with matching including: the need for the patient to look away from the stimulus to find a response; the interference of visual acuity; and/or the limitations of administering the test on a smaller, computer-based device, such as a smartphone. A block-type stimulus, or other relatively large area or regions, is used in combination with the Forced Choice stimulus presentation manner described above. In this presentation, a colored block, area or region is presented in one of several sections, with the remaining sections presented as a grey "background" color. The block, area or region may be in the shape of a square, circle, pie, blob, etc., and the patient can respond by touching or clicking on the colored area or region on the screen, by using a direction-oriented keypad, by providing a verbal response, or through eye tracking device and/or software. Based on the patient's correct or incorrect response, the color contrast level of the colored block, area or region is decreased or increased. The grey sections remain constant. The location of the colored block can be deliberate or random and can change with each presentation. The test continues until the patient's threshold for each color is determined and each cone-isolating color (red, green, and blue) is repeated in the same fashion for each eye.

In further aspects, sine wave gratings, for example as described in "Perception Lecture Notes: Spatial Frequency Channels" (Prof. Michael Landy, https://www.cns.nyu.edu/~david/courses/perception/lecturenotes/channels/channels.html, last accessed Oct. 9, 2020), which is incorporated herein by reference in its entirety, which can be utilized for purposes of grey scale contrast sensitivity testing by plotting a sinusoidal function of lightness, varying the contrast across different frequencies. The highest contrast level is created by varying the color presented in a full range of black to white. Varying the frequency of the sinusoidal function yields lines or circles which are closer or farther apart. Specific contrast levels are achieved by varying the intensity of the sinusoidal function for each spatial frequency. In the case of cone contrast testing, a sinusoidal function which varies in luminance of cone-isolating colors (red, green, and blue) across a grating pattern is used to stimulate each cone type independently. Either linear or concentric circle patterns can be presented for testing purposes. In such case, the linear or circular pattern can be presented as patterns of colors, with each color pattern fading in intensity of the same color from a higher contrast to lower contrast level presenting a stimulus pattern of dark, medium, light, medium, dark intensity of the same color. In some presentations, the area around the sinusoidal pattern, or the "background" is grey. While grey-scale contrast sensitivity can be measured by varying the contrast levels over many different spatial frequencies, this method may not work effectively relative to cone-isolating colors as the number of presentations must be multiplied by three to accommodate the three cone types, which can make the testing procedures too long or cumbersome so to be effectively used in practice. Hence, in some aspects, in such a cone-isolating color version, a limited number of spatial frequencies can be used to reduce the number of stimuli required to complete the test. A preferred number of spatial frequencies is one, the peak of the contrast curve. In such procedures, a sine wave grating may be presented as a single stimulus (either static or modified in real-time) or as one of several areas or regions as described above. In such cases, a patient may identify whether the sinusoidal image is perceived by identifying in which area or region the sinusoidal image is present. Based on the patient's correct or incorrect response, the color contrast level of the sinusoidal pattern is decreased or increased. The grey "background" color contrast level remains constant. The location of the sinusoidal stimulus can be deliberate or random and may change with each presentation. The patient's threshold for that cone-isolating color may then be determined by the lowest color contrast sinusoidal image the patient can see for that color. The test continues until the patient's threshold for each color is determined and each cone-isolating color (red, green, and blue) can be repeated in the same fashion for each eye.

Additionally, current procedures typically utilize a computer's ability to produce color contrast at low contrast levels. However, off-the-shelf computers are typically only able to present a limited number of color contrast levels, which can limit the ability to measure very fine differences in color perception required for the earliest detection of disease, disease progression, and/or therapy improvement, and there is a need to create additional color contrast levels.

"Spatial dithering" is a method to produce additional colors by varying the individual colors making up the colored stimulus pattern. Much like impressionistic paintings, a patient's overall perception of the color contrast stimulus will comprise the diffusion of the color contrast levels of the individual components of the stimulus pattern, i.e., the diffusion of the dots, squares, blobs, etc., within the pattern. In computer graphics, for example, spatial dithering is the use of two or more different colors in a pattern creating a different, third, color.

Accordingly, in some aspects, the current devices, procedures, and methods can utilize a similar "spatial dithering" method of presenting the color stimulus by varying the color contrast of the individual pixels or areas making up the colored stimulus, wherein a single cone-isolating color is presented as a stimulus pattern, area, or region formed from, for example, dots, squares, blobs, etc., in varying contrast levels to control the overall perception of color contrast. This method produces additional perceivable color contrast levels of the same color not creating additional colors through the use of differing colors as in computer graphics. This method allows for many more color contrast levels to be achieved using off-the-shelf computers not otherwise capable producing or presenting such colors. The result is a finer presentation of cone contrast levels and a more precise measurement of a patient's change in color perception, resulting in a more sensitive instrument for earlier detection of disease, disease progression and visual improvements from therapies, etc. These devices, procedures, and methods differ from pseudo-isochromatic color vision tests, which use random dot patterns of differing colors (e.g., red, green) to determine if a patient can distinguish between them, in that the same cone-isolating colors are presented in differing color contrast levels to create additional contrast levels to determine the threshold of specific cone types.

In aspects of such procedures, a stimulus may be presented as a plurality of colored dots of the same cone-isolating color (red, green, or blue) or, alternatively, cone-isolating color plus grey. The actual color contrast level is controlled by varying the color contrast of the individual dots making up the stimulus, for example color contrast 1, color contrast 2, and/or grey, where color contrast 1 and color contrast 2 are both contrast levels of the same color. The background is grey. By varying the color contrast over 2 or more contrast levels, the perception of the color contrast can be further controlled. The size of the color contrast dots may vary within the stimulus to further refine the color contrast level achieved. The overall grouping of the plurality of dots may represent a letter, an image, or can simply comprise a colored section area or region. The colored stimulus may be presented as a single stimulus or in a forced choice pattern as defined above. Presentations may be two-dimensional or multi-dimensional. Based on a patient's correct or incorrect response, the color contrast level of the some or all of the dots making up the stimulus will decrease or increase. The patient's threshold for that cone-isolating color may then be determined by the lowest color contrast image the patient can see for that color. The test continues until the patient's threshold for each color is determined and each cone-isolating color (red, green, and blue) is repeated in the same fashion for each eye.

In some further aspects, temporal dithering can also be utilized for purposes of creating additional color contrast levels. According to this method, additional color contrast levels can be created by rapidly changing the color contrast (cc) level of a same cone-isolation color (red, green, or blue) of a single stimulus. In such cases, colors can be rapidly presented in a pattern such as: cc1, cc2, cc1, cc2, where, for example, cc1 is equivalent to color 1 at contrast level 1 and cc2 is color 1 at contrast level 2, and the rapid change from cc1 to cc2 is imperceptible to a patient. The underlying effect, however, is that the perceivable color contrast level is a diffusion of the color contrast levels presented. Alternatively, additional presentation patterns could further control the perceived color contrast levels. For example, cc1, cc1, cc2, cc1, cc1, cc2, would create a different color contrast level than the previous example. In this way, many additional color contrast levels can be presented using off-the-shelf computer technology. Accordingly, where such testing procedures are utilized, the color contrast level of the colored section can be increased or decreased based on a patient's response. Much like the previous examples, the grey "background" color remains constant and the patient's threshold for a particular cone-isolating color is determined by the lowest color contrast image the patient can see for that color. Each cone-isolating color (red, green, and blue) is repeated in the same fashion. The test continues until the patient's threshold for each color is determined and each cone-isolating color (red, green, and blue) is repeated in the same fashion for each eye. In such cases, the colored stimulus can be presented as a single stimulus or in a forced choice pattern as described above. Also, presentations may be two-dimensional or multi-dimensional.

In further aspects, remote monitoring of patients is becoming more and more necessary as diabetes and eye disease continues to rise exponentially while the number of ophthalmologists is declining and only a portion of optometry is medical. Additionally, scheduling an eye exam weeks or months in advance can allow critical eye disease to advance and cause irreversible vision loss. Moreover, many older people are fearful of contracting COVID-19, making them less likely to schedule regular exams. Hence, there is a great need for an affordable, at-home or other tele-health device that can monitor disease progression in between eye exams. Computer tablets with good display characteristics capable of producing precise color contrast levels are expensive and can easily be dropped or broken such that alternative testing devices are needed. In accordance therewith, in some aspects, an alternative testing device for at-home or tele-health use can include a smartphone, smart watch, or computer-driven headset where color contrast stimuli may be presented as 2 or 3-D images. Any of the above stimuli described stimuli may be presented in sections. And, while the number of sections can vary, a preferred method is to present 4-6 sections in a ring format to create enough differentiation in eye movement to utilize eye tracking. In such procedures, a patient can be instructed to view the colored stimulus. If using a headset, eye tracking software monitors the patient's gaze and determines whether the patient has identified the colored stimuli. If the patient gazes at the colored stimulus for a predetermined period of time, for example, the response may be recorded as correct. By contrast, if the patient looks away from the colored stimulus for a predetermined number of seconds or directs his gazes inconsistently at both the colored stimulus and grey area, the response may be recorded as incorrect. In an alternate presentation, where voice recognition software is utilized, a patient can respond via a verbal command. Based on a patient's correct or incorrect response, the color contrast level of the colored section can be decreased or increased. Much like the previous examples, the grey "background" color contrast level remains constant. The patient's threshold for that cone-isolating color is determined by the lowest color contrast stimulus the patient can see for that color. The test continues until the patient's threshold for each color is determined and each cone-isolating color (red, green, and blue) is repeated in the same fashion for each eye.

Turning now to FIGS. 27A-31B, which illustrate examples of the previously discussed "Forced Choice" type testing procedures, the use of sine wave gratings, as well as the use of spatial and temporal dithering for purposes of assessing cone contrast levels in a patient.

Figure 27A:
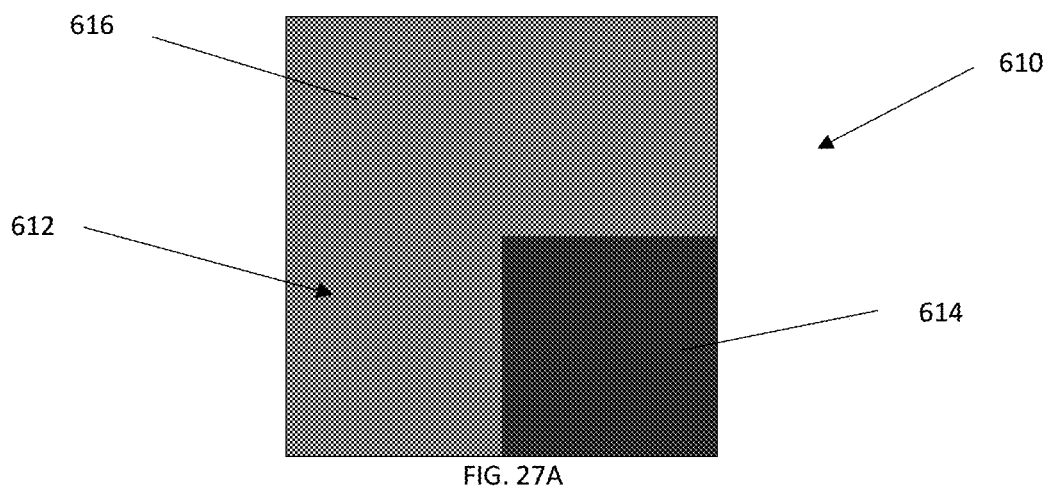
FIGS. 27A-27C schematically illustrate a region or area-type cone contrast color vision test utilizing a quadrant-type system.
Figure 27B:
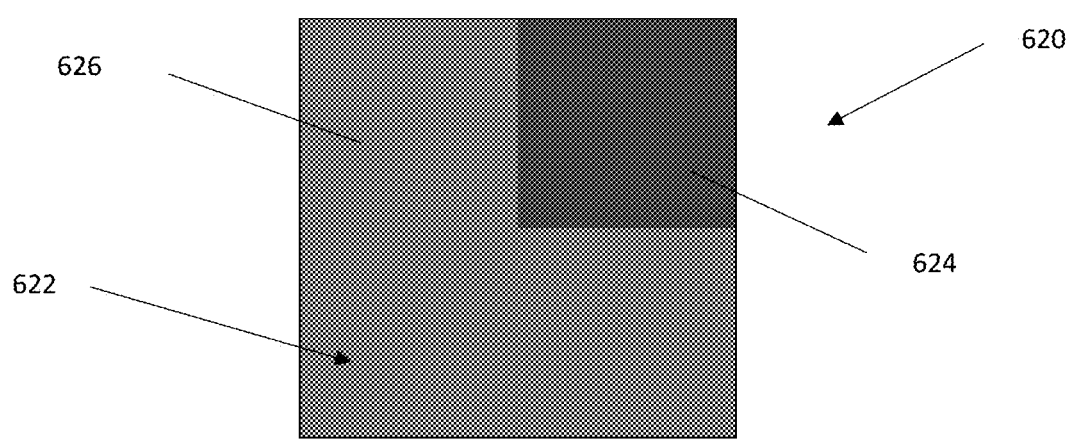
Figure 27C:
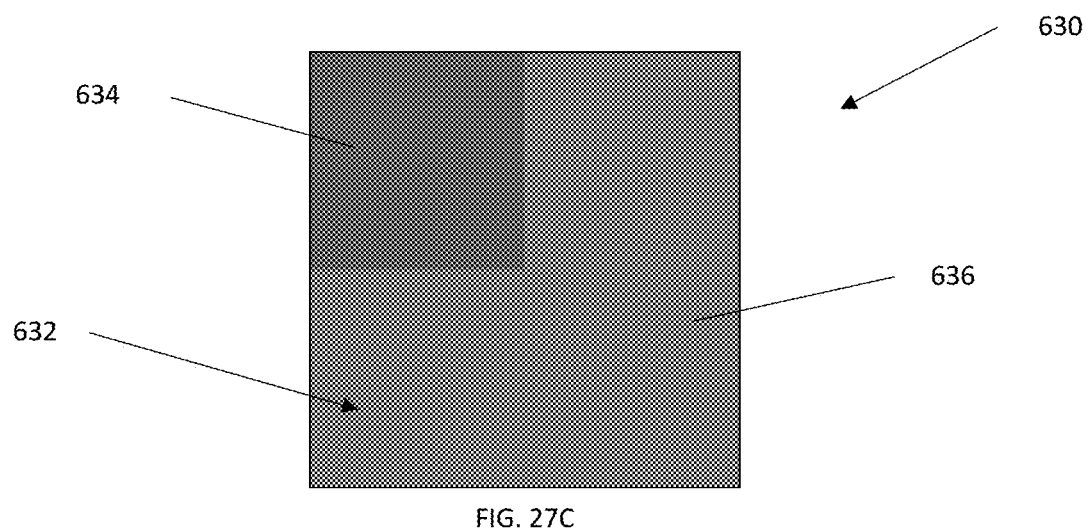

FIGS. 27A-27C illustrate an example of one type of "Forced Choice" color contrast level testing procedure. As shown in FIG. 27A, during such test, a first testing screen 610 comprising a testing field 612 including a first color at a first contrast level in a first sub-region 614 and a second color (grey) at a first contrast level in a second sub-region 616 may be displayed to a patient. As compared to CCT testing procedures utilizing characters requiring visual acuity, it is seen that the testing field 612, and first sub-region 614 and second sub-region 616 thereof, are configured to encompass a large or substantial portion of the testing screen 610 such that patients with low visual acuity and/or individuals performing testing on smaller devices, such as smart phones, may readily perceive sub-region 614. In accordance therewith, testing field 612 can utilize a quadrant-type system wherein a first color for which color contrast level is to be tested (red, green or blue) is randomly presented in a first one of four quadrants, and the second color (grey) is presented in the remaining three quadrants of the testing field 612. As shown in FIG. 27A, the first color is shown as occupying the lower right quadrant and the second color is shown as occupying the remaining quadrants. Hence, where the first contrast level of the first color in the first region 614 is perceived by a patient to occupy the lower right quadrant of testing field 612, the patient may provide an appropriate input thereof by touching the touchscreen at that position, by inputting a signal via a directional-type touchpad or input device, by providing an appropriate voice indication thereof to a computer executing voice recognition software, or such input may be provided by monitoring and/or recording the patient's eye movements or gaze, which is input to a computer executing eye-tracking software. Where a patient is unable to ascertain the first color presented, a patient may provide a "pass"-type input by means of a touchscreen icon (not shown), by inputting a signal via a directional-type touchpad or input device, by providing a voice indication thereof, or by monitoring and/or recording the patient's eye movements or gaze. Based on the patient's correct or incorrect response, the color contrast level of the first color can be decreased or increased as appropriate and a new or refreshed testing screen presented.

As shown in FIG. 27B, where a correct response is input by the patient or measured at testing screen 610, a new screen may be presented or refreshed such that testing screen 620 displayed. As may be appreciated, testing screen 620 is similar to testing screen 610 in that it also comprises a quadrant-type system wherein the first color for which color contrast level is being tested (red, green or blue) is deliberately or randomly presented in a first one of four quadrants, and the second color (grey) is presented in the remaining three quadrants of the testing field 622. However, as compared to testing screen 610, the contrast level of the first color has been modified and the location of the first color has also been shifted to occupy sub-region 624 located at the upper right quadrant thereof and the second color (grey) has shifted to occupy the remaining sub-regions of 626. That is, the first color has shifted to occupy third sub-region 624 and the second color has shifted to occupy fourth sub-region 626. Additionally, as compared to testing screen 610, the contrast level of the first color of third sub-region 624 has been changed to comprise a second contrast level that is lower than that of first sub-region 614. Accordingly, where the second contrast level of the first color in the third sub-region 624 is perceived by a patient to occupy the upper right quadrant of testing field 622, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software. Where a patient is unable to ascertain the first color, the patient may provide a "pass"-type input by means of a touchscreen icon (not shown), by inputting a signal via a directional-type touchpad or input device, by providing a voice indication thereof, or by monitoring and/or recording the patient's eye movements or gaze. Based on the patient's correct or incorrect response, the color contrast level of the first color can be increased or decreased, as appropriate and a new or refreshed testing screen presented.

As shown in FIG. 27C, where a correct response is input by the patient or measured at testing screen 620, a new screen may be presented or refreshed such that testing screen 630 displayed. As may be appreciated, testing screen 630 is similar to testing screens 610 and 620 in that they also comprise a quadrant-type system wherein the first color for which color contrast level is being tested (red, green or blue) is deliberately or randomly presented in a first one of four quadrants, and the second color (grey) is presented in the remaining three quadrants of the testing field 632. However, as compared to testing screens 610 and 620, the contrast level of the first color has been modified and the location of the first color has also shifted to occupy sub-region 634 located at the upper left quadrant thereof and the second color has shifted to occupy the remaining sub-regions 636. That is, the first color has shifted to occupy fifth sub-region 634 and the second color has shifted to occupy sixth sub-region 636. Additionally, as compared to testing screens 610 and 620, the contrast level of the first color of fifth sub-region 634 has been changed to comprise a third contrast level that is higher or lower that of the first and third sub-regions 614 and 624 based on the patients correct or incorrect response. Accordingly, where the third contrast level of the first color in the fifth sub-region 634 is perceived by a patient to occupy the upper left quadrant of testing field 632, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software. Where a patient is unable to ascertain the first color, the patient may provide a "pass"-type input by means of a touchscreen icon (not shown), by inputting a signal via a directional-type touchpad or input device, by providing a voice indication thereof, or by monitoring and/or recording the patient's eye movements or gaze.

As may be appreciated, additional testing screens may be presented and different contrast levels presented until the patient's threshold for a specific color is determined. Upon completion of a specific color phase in the testing process, testing software will continue to the next color phase for the tested eye. If all color phases have been completed for the tested eye, testing software displays an eye selection screen and continues the testing process with the next eye to be tested. If all color phases for both eyes have been completed, the test process is complete. As may be appreciated, while the above primarily describes decreasing contrast levels in the case of a correct response, one or more first color contrast levels and their positions may be randomly presented, or re-presented as needed, for example, in the case of a pass-type input, a delay in providing an input, or lack of an input within a specified time limit.

Figure 28A:
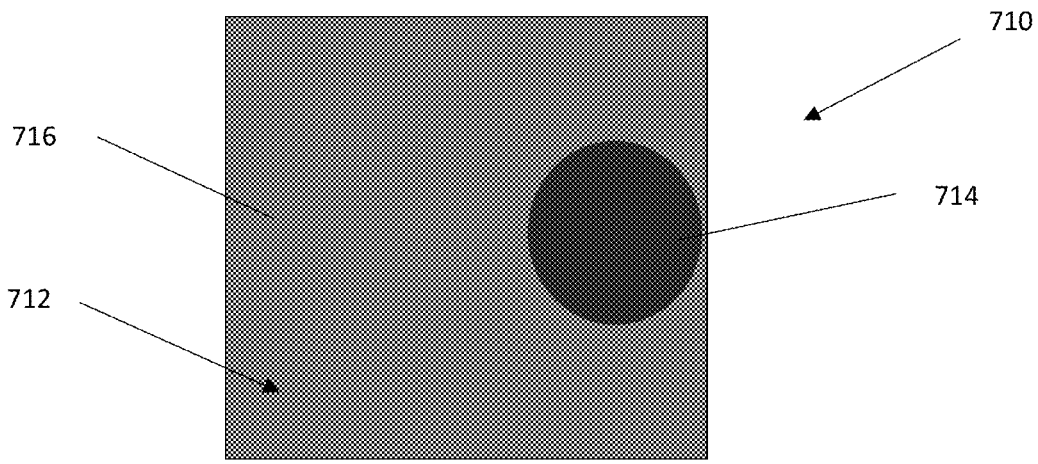
FIGS. 28A-28C schematically illustrate a region or area-type cone contrast color vision test utilizing a directional-type system.
Figure 28B:
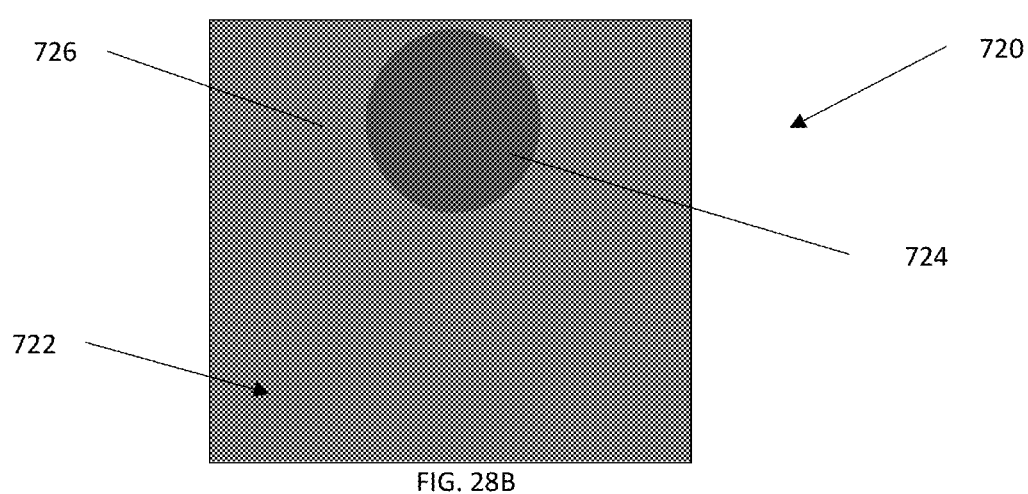
Figure 28C:
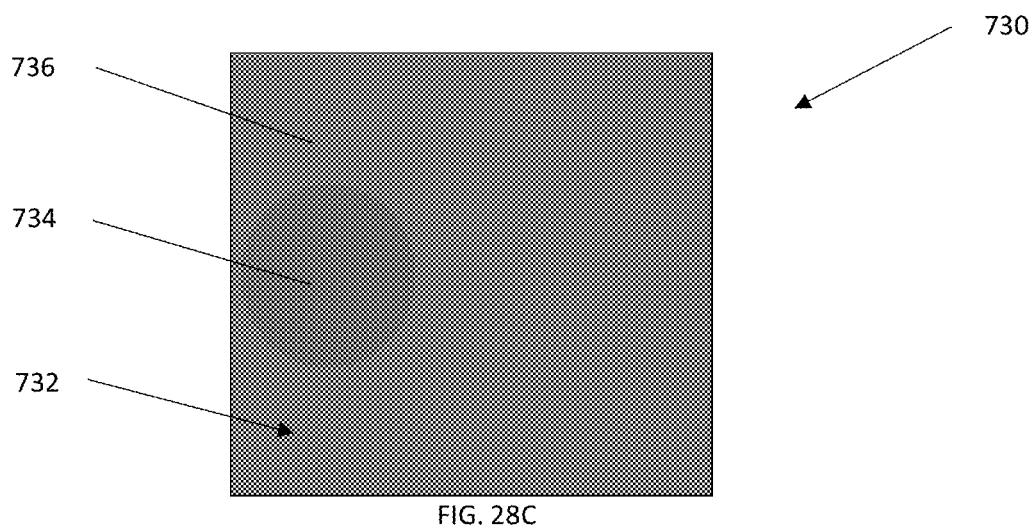

As shown in FIGS. 28A-28C, another example of a contrast level testing procedure is illustrated, which is similar to the procedure of FIGS. 27A-27C, but rather than utilizing quadrants, such procedure utilizes an area or region, e.g., (e.g., large circles) corresponding to a positional location of the display screen that may be readily perceived by individuals with low visual acuity. As may be appreciated by such figures, the areas or regions are displayed to the testing screen such that they are disposed at a plurality of readily identifiable testing screen positional locations, for example, at upper, lower, leftward or rightward positions. To this end, as shown in FIG. 28A, during a test, a first testing screen 710 comprising a testing field 712 including first color at a first contrast level in a first sub-region 714 and a second color (grey) in a second sub-region 616 may be displayed to a patient. As compared to CCT testing procedures utilizing characters requiring both color vision and visual acuity, it is seen that the testing field 712, and first sub-region 714 and second sub-region 716 thereof, are configured to encompass a large, or substantial, portion of the testing screen 710 such that patients with low visual acuity and/or individuals performing testing on smaller devices, such as smart phones, may readily perceive sub-regions 714 and 716. In accordance therewith, testing field 712 can utilize an orientation system wherein a first color for which color contrast level is to be tested (red, green or blue) is randomly presented in a first one of an upper, lower, leftward or rightward screen position and the second color (grey) is presented in the remainder of the testing field 712. As shown in FIG. 28A, the first color is shown as occupying the rightward screen position and the second color is shown as occupying the remainder of the testing field 712, i.e., second sub-region 716. Hence, where the first contrast level of the first color in the first region 714 is perceived by a patient to occupy the rightward position of testing field 712, the patient may provide an appropriate input thereof by touching the touchscreen at that position, by inputting a signal via a directional-type touchpad or input device, by providing an appropriate voice indication thereof, or such input may be provided by monitoring, by recording the patient's eye movements or gaze via the use of eye-tracking software and/or patient's hand gestures via the use of hand-gesture software. Where a patient is unable to ascertain the first color, a patient may provide a "pass"-type input by means of a touchscreen icon (not shown), by inputting a signal via a touchpad or input device, by providing a voice indication thereof, by monitoring and/or recording the patient's eye movements or gaze and/or monitoring and/or recording the patient's hand gestures. Based on the patient's correct or incorrect response, the color contrast level of the first color can be decreased or increased, as appropriate and a new or refreshed testing screen presented.

As shown in FIG. 28B, where a correct response is input by the patient or measured at testing screen 710, a new screen may be presented or refreshed such that testing screen 720 displayed. As may be appreciated, testing screen 720 is similar to testing screen 710 in that it also comprises a positional-type system wherein the first color for which color contrast level is being tested (red, green or blue) is randomly or deliberately presented in a first one of four screen positions, and the second color (grey) is presented in the remainder of the testing filed 722. However, as compared to testing screen 710, the contrast level of the first color has been modified and the location of the first color has also shifted to occupy sub-region 724 located at the upper position thereof and the second color has shifted to occupy sub-region 726. That is, the first color has shifted to occupy third sub-region 724 and the second color has shifted to occupy fourth sub-region 726. Additionally, as compared to testing screen 710, the contrast level of the first color of third sub-region 724 has been changed to comprise a second contrast level that is lower that of first sub-region 714. Accordingly, where the second contrast level of the first color in the third sub-region 724 is perceived by a patient to occupy the upper position of testing field 722, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software. Where a patient is unable to ascertain the first color, the patient may provide a "pass"-type input by means of a touchscreen icon (not shown), by inputting a signal via a touchpad or input device, by providing a voice indication thereof, or by monitoring and/or recording the patient's eye movements or gaze. Based on the patient's correct or incorrect response, the color contrast level of the first color can be decreased or increased, as appropriate and a new or refreshed testing screen presented.

As shown in FIG. 28C, where a correct response is input by the patient or detected at testing screen 720, a new screen may be presented or refreshed such that testing screen 730 displayed. As may be appreciated, testing screen 730 is similar to testing screens 710 and 720 in that it also comprises a positional-type system wherein the first color for which color contrast level is being tested (red, green or blue) is randomly or deliberately presented in a first one of four positions, and the second color (grey) is presented in the remainder of testing field 732. However, as compared to testing screens 710 and 720, the contrast level of the first color has been modified and the location of the first color has also shifted to occupy sub-region 734 located at the leftward position thereof and the second color has shifted to occupy the remaining sub-region 736. That is, the first color has shifted to occupy fifth sub-region 734 and the second color has shifted to occupy sixth sub-region 736. Additionally, as compared to testing screens 710 and 720, the contrast level of the first color of fifth sub-region 734 has been changed to comprise a third contrast level that is higher or lower that of the first and third sub-regions 714 and 724. Accordingly, where the third contrast level of the first color in the fifth sub-region 734 is perceived by a patient to occupy the leftward position of testing field 732, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software, or by an appropriate hand gesture thereof, or such input may be provided by monitoring and/or recording the patient's hand gestures and the use of hand-gesture software. Where a patient is unable to ascertain the first color, the patient may provide a "pass"-type input by means of a touchscreen icon (not shown), by inputting a signal via a touchpad or input device, by providing a voice indication thereof, by monitoring and/or recording the patient's eye movements or gaze, or by monitoring and/or recording the patient's hand gesture.

As may be appreciated, additional testing screens may be presented and different contrast levels presented until the patient's threshold for a specific color is determined. Upon completion of a specific color phase in the testing process, testing software will continue to the next color phase for the tested eye. If all color phases have been completed for the tested eye, testing software can display an eye selection screen and continue the testing process with the next eye to be tested. If all color phases for both eyes have been completed, the test process is complete. As may be appreciated, while the above primarily describes decreasing contrast levels in the case of a correct response, increasing contrast levels are presented in the case of an incorrect response, including a pass-type input, a delay in providing an input, or lack of an input. In addition, one or more first color contrast levels and their positions may be randomly presented, or re-presented. Additionally, while the above examples describe a total of four quadrants or screen positions, it should be appreciated that the subject matter is not particularly limited to a total four quadrants or four screen positions, and the number of sub-regions or positions may be higher or lower.

Referring now to FIGS. 29A-29D, in addition to the above use of quadrants and the screen position of sub-regions, the quadrants and sub-regions or areas can be configured to utilize sine wave gratings for purposes of assessing cone contrast sensitivity.

Figure 29A:
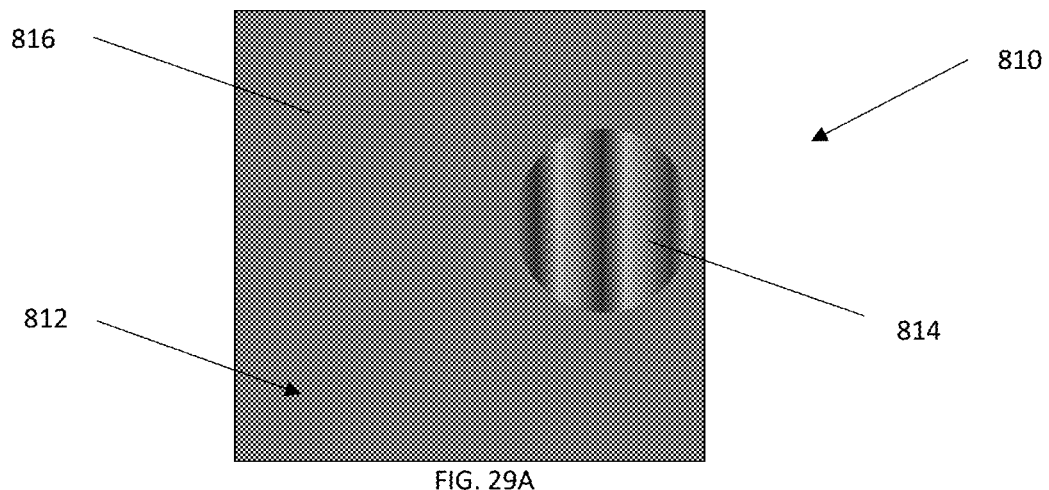
FIGS. 29A-29D schematically illustrate a region or area-type cone contrast color vision test utilizing a linear and/or circular sine-wave grating system.

As shown in FIG. 29A, during a test, a first testing screen 810 comprising a testing field 812 including a linear sine wave grating of a first color at a first contrast level in a first sub-region 814 and a second color (grey) at a set contrast level in a second sub-region 816 may be displayed to a patient. As compared to CCT testing procedures utilizing characters requiring both color vision and visual acuity, it is seen that the testing field 812, and first sub-region 814 and second sub-region 816 thereof, are configured to encompass a large, or substantial, portion of the testing screen 810 such that patients with low visual acuity and/or individuals performing testing on smaller devices, such as smart phones, may readily perceive sub-regions 814 and 816. In accordance therewith, testing field 812 can utilize an orientation system wherein a first color for which color contrast level is to be tested (red, green or blue) is randomly presented in a first one of an upper, lower, leftward or rightward screen position and the second color is presented in the remainder of the testing field 812. As shown in FIG. 29A, the first color is shown as occupying the rightward screen position and the second color is shown as occupying the remainder of the testing field 812, i.e., second sub-region 816. Hence, where the first contrast level of the first color in the first region 814 is perceived by a patient to occupy the rightward position of testing field 812, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze via the use of eye-tracking software or by providing an appropriate hand gesture indication thereof, or such input may be provided by monitoring and/or recording the patient's hand gestures. Where a patient is unable to ascertain the first color, a patient may provide a "pass"-type input by means of a touchscreen icon (not shown), by inputting a signal via a touchpad or input device, by providing a voice indication thereof, by monitoring and/or recording the patient's eye movements or gaze, or by monitoring and/or recording the patient's hand gestures. Based on the patient's correct or incorrect response, the color contrast level of the first color can be decreased or increased, as appropriate and a new or refreshed testing screen presented.

Figure 29B:
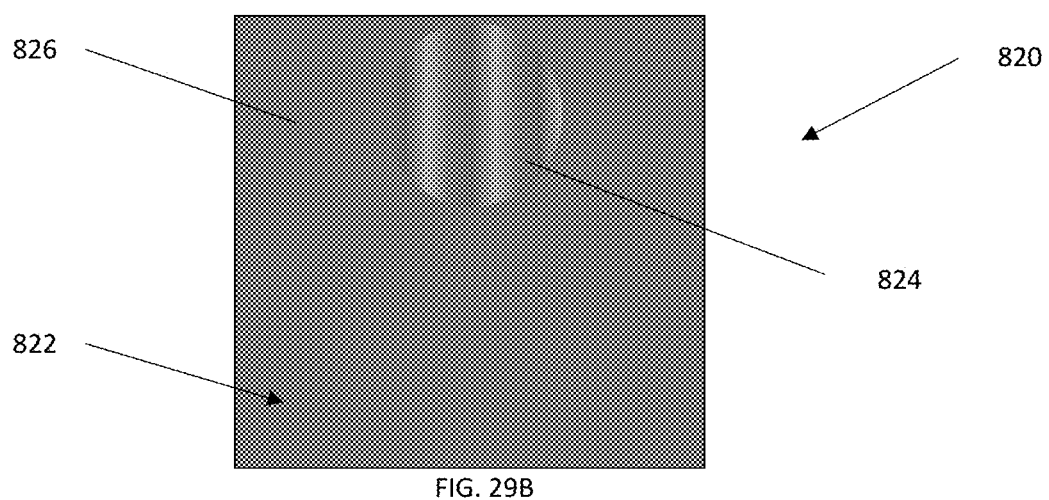

As shown in FIG. 29B, where a correct response is input by the patient or measured at testing screen 810, a new screen may be presented or refreshed such that testing screen 820 displayed. As may be appreciated, testing screen 820 is similar to testing screen 810 in that it also comprises a positional-type system wherein the first color for which color contrast level is being tested (red, green or blue) is randomly or deliberately presented in a first one of several screen positions, and the second color (grey) is presented in the remainder of the testing field 822. However, as compared to testing screen 810, the contrast level of the first color has been modified and the location of the first color has also shifted to occupy sub-region 824 located at the upper position thereof and the second color has shifted to occupy sub-region 826. That is, the first color has shifted to occupy third sub-region 824 and the second color has shifted to occupy fourth sub-region 826. Additionally, as compared to testing screen 810, the contrast level of the first color of third sub-region 824 has been changed to comprise a second contrast level that is higher or lower that of first sub-region 814 based on the patient's correct or incorrect response. Accordingly, where the second contrast level of the first color in the third sub-region 824 is perceived by a patient to occupy the upper position of testing field 822, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software or by providing an appropriate hand gesture indication thereof, or such input may be provided by monitoring and/or recording the patient's hand gestures and the use of hand-gesture software. Where a patient is unable to ascertain the first color, the patient may provide a "pass"-type input by means of a touchscreen icon (not shown), by inputting a signal via a touchpad or input device, by providing a voice indication thereof, by monitoring and/or recording the patient's eye movements or gaze or by monitoring and/or recording the patient's hand gestures. Based on the patient's correct or incorrect response, the color contrast level of the first color can be decreased or increased, as appropriate and a new or refreshed testing screen presented.

Figure 29C:
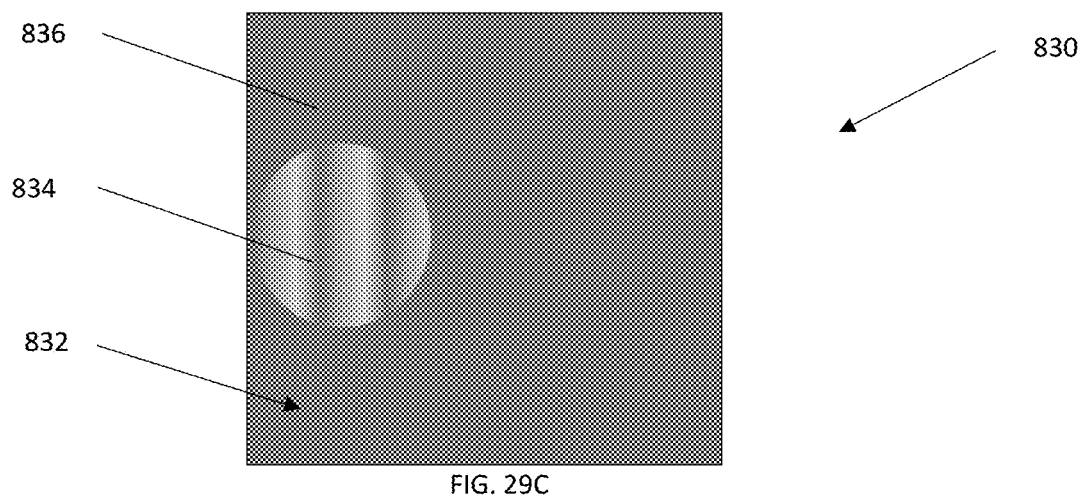

As shown in FIG. 29C, where a correct response is input by the patient or measured at testing screen 820, a new screen may be presented or refreshed such that testing screen 830 displayed. As may be appreciated, testing screen 830 is similar to testing screens 810 and 820 in that it also comprises a positional-type system wherein the first color for which color contrast level is being tested (red, green or blue) is randomly or deliberately presented in a first one of several positions, and the second color (grey) is presented in the remainder of testing field 832. However, as compared to testing screens 810 and 820, the contrast level of the first color has been modified and the location of the first color has also shifted to occupy sub-region 834 located at the leftward position thereof and the second color has shifted to occupy the remaining sub-region 836. That is, the first color has shifted to occupy fifth sub-region 834 and the second color has shifted to occupy sixth sub-region 836. Additionally, as compared to testing screens 810 and 820, the contrast level of the first color of fifth sub-region 834 has been changed to comprise a third contrast level that is higher or lower, based on the patient's response, that of the first and third sub-regions 814 and 824. Accordingly, where the third contrast level of the first color in the fifth sub-region 834 is perceived by a patient to occupy the leftward position of testing field 832, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software, or by providing an appropriate hand gesture indication thereof, or such input may be provided by monitoring and/or recording the patient's hand gestures and the use of hand-gesture software. Where a patient is unable to ascertain the first color, the patient may provide a "pass"-type input by means of a touchscreen icon (not shown), by inputting a signal via a touchpad or input device, by providing a voice indication thereof, by monitoring and/or recording the patient's eye movements or gaze or monitoring and/or recording the patient's hand gestures.

Figure 29D:
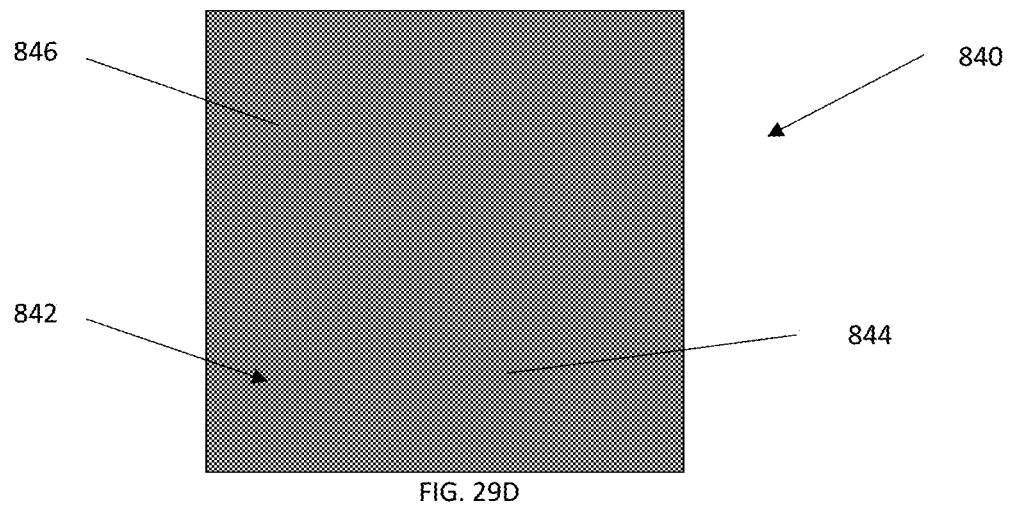

As shown in FIG. 29D, testing procedures utilizing sine wave gratings can also be configured to comprise circular type gratings and apply similar methods set forth relative to FIGS. 29A-29C. Hence, testing screen 840 is shown as including a testing field 842 including first sub-region 844 and second sub-region 846, wherein first sub-region is shown as occupying a lower screen position, and second sub-region 846 occupying the remainder of field 846.

As may be appreciated, additional testing screens may be presented and different contrast levels presented until the patient's threshold for a specific color is determined. Upon completion of a specific color phase in the testing process, testing software will continue to the next color phase for the tested eye. If all color phases have been completed for the tested eye, testing software displays an eye selection screen and continue the testing process with the next eye to be tested. If all color phases for both eyes have been completed, the test process is complete. As may be appreciated, while the above primarily describes decreasing contrast levels in the case of a correct response, one or more first color contrast levels and their positions may be randomly presented, or re-presented as needed, for example, in the case of a pass-type input, a delay in providing an input, or lack of an input. Additionally, while the above examples describe a total of four quadrants or screen positions, it should be appreciated that the subject matter is not particularly limited to a total four quadrants or four screen positions, and the number of sub-regions or positions may be higher or lower.

Referring now to FIGS. 30A-30D, in addition to the above use of quadrants and the screen position of sub-regions, the quadrants and sub-regions or areas can be configured to utilize spatial or temporal dithering for purposes of assessing cone contrast sensitivity.

Figure 30A:
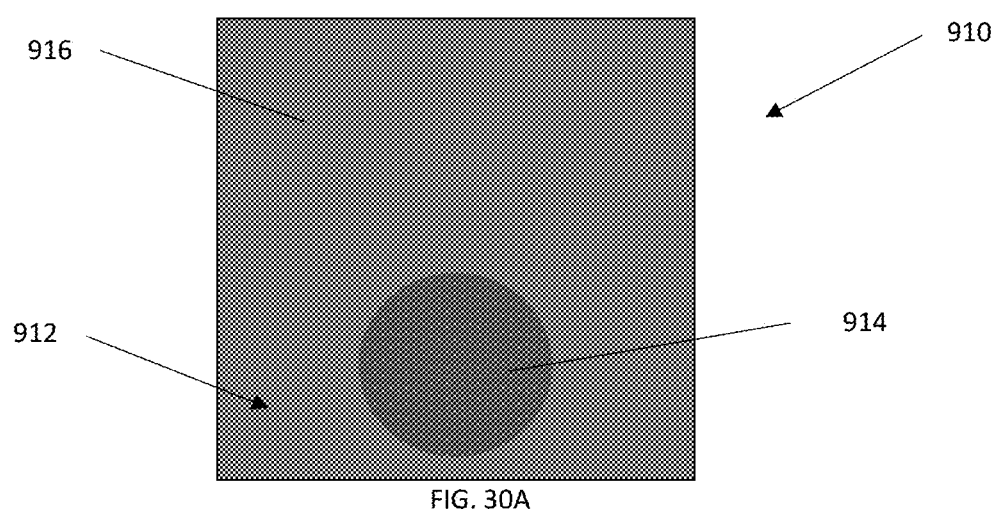
FIGS. 30A-30C schematically illustrate a region or area-type cone contrast color vision test utilizing spatial or temporal dithering.

As shown in FIG. 30A, during a test, a first testing screen 910 comprising a testing field 912 including a first color at a first contrast level in a first sub-region 914 provided via the use of spatial or temporal dithering, and a second color (grey) at a first contrast level in a second sub-region 916 may be displayed to a patient. As compared to CCT testing procedures utilizing characters requiring both color vision and visual acuity, it is seen that the testing field 912, and first sub-region 914 and second sub-region 916 thereof, are configured to encompass a large, or substantial, portion of the testing screen 910 such that patients with low visual acuity and/or individuals performing testing on smaller devices, such as smart phones, may readily perceive sub-regions 914 and 916. In accordance therewith, testing field 912 can utilize an orientation system wherein a first color for which color contrast level is to be tested (red, green or blue) is randomly or deliberately presented in a first one of an upper, lower, leftward or rightward screen position and the second color is presented in the remainder of the testing field 912. As shown in FIG. 30A, the first color is shown as occupying the lower screen position and the second color is shown as occupying the remainder of the testing field 912, i.e., second sub-region 916. Hence, where the first contrast level of the first color in the first region 914 is perceived by a patient to occupy the lower position of testing field 912, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze via the use of eye-tracking software, or by providing an appropriate hand gesture indication thereof, or such input may be provided by monitoring and/or recording the patient's hand gestures via the use of hand-gesture software. Where a patient is unable to ascertain the first color, a patient may provide a "pass"-type input by means of a touchscreen icon (not shown), by inputting a signal via a touchpad or input device, by providing a voice indication thereof, by monitoring and/or recording the patient's eye movements or gaze, or by monitoring and/or recording the patient's hand gestures. Based on the patient's correct or incorrect response, the color contrast level of the first color can be decreased or increased, as appropriate and a new or refreshed testing screen presented.

Figure 30B:
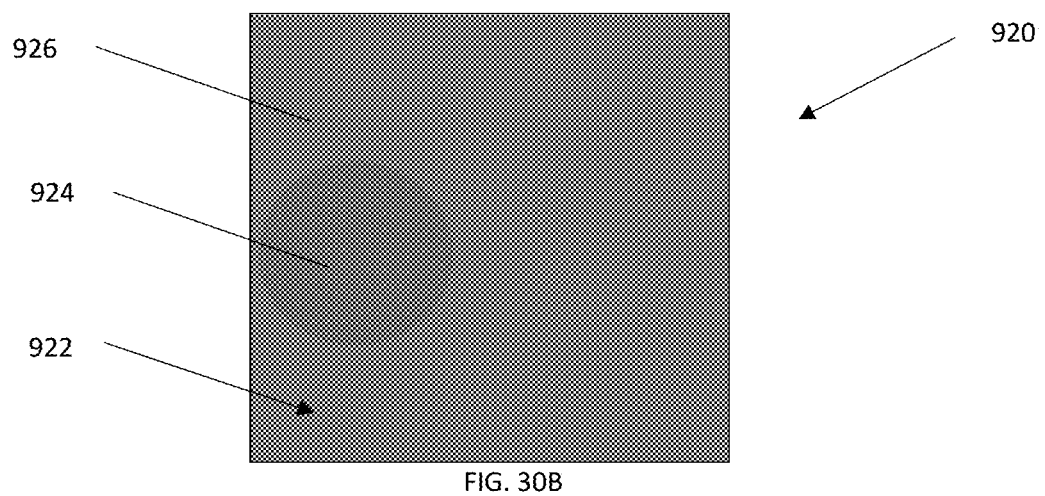

As shown in FIG. 30B, where a correct response is input by the patient or measured at testing screen 910, a new screen may be presented or refreshed such that testing screen 920 displayed. As may be appreciated, testing screen 920 is similar to testing screen 910 in that it also comprises a positional-type system wherein the first color for which color contrast level is being tested (red, green or blue) is randomly or deliberately presented in a first one of four screen positions, and the second color (grey) is presented in the remainder of the testing field 922. However, as compared to testing screen 910, the contrast level of the first color has been modified and the location of the first color has also shifted to occupy sub-region 924 located at the leftward position thereof and the second color has shifted to occupy sub-region 926. That is, the first color has shifted to occupy third sub-region 924 and the second color has shifted to occupy fourth sub-region 926. Additionally, as compared to testing screen 910, and by the processes of spatial or temporal dithering, the contrast level of the first color of third sub-region 924 has been changed to comprise a second contrast level that is lower that of first sub-region 914. Accordingly, where the second contrast level of the first color in the third sub-region 924 is perceived by a patient to occupy the leftward position of testing field 922, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software, or by providing an appropriate hand gesture thereof, or such input may be provided by monitoring and/or recording the patient's had gestures and the use of hand-gesture software. Where a patient is unable to ascertain the first color, the patient may provide a "pass"-type input by means of a touchscreen icon (not shown), by inputting a signal via a touchpad or input device, by providing a voice indication thereof, by monitoring and/or recording the patient's eye movements or gaze, or by monitoring and/or recording the patient's hand gestures. Based on the patient's correct or incorrect response, the color contrast level of the first color can be decreased or increased, as appropriate and a new or refreshed testing screen presented.

Figure 30C:
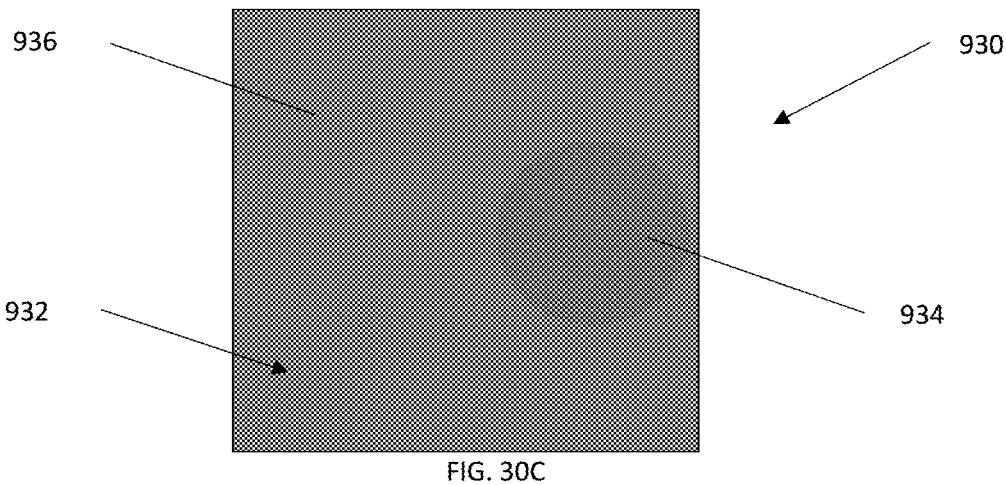

As shown in FIG. 30C, where a correct response is input by the patient or measured at testing screen 920, a new screen may be presented or refreshed such that testing screen 930 displayed. As may be appreciated, testing screen 930 is similar to testing screens 910 and 920 in that it also comprises a positional-type system wherein the first color for which color contrast level is being tested (red, green or blue) is randomly or deliberately presented in a first one of four positions, and the second color (grey) is presented in the remainder of testing field 932. However, as compared to testing screens 910 and 920, the contrast level of the first color has been modified by spatial or temporal dithering processes and the location of the first color has also shifted to occupy sub-region 934 located at the rightward position thereof and the second color has shifted to occupy the remaining sub-region 936. That is, the first color has shifted to occupy fifth sub-region 934 and the second color has shifted to occupy sixth sub-region 936. Additionally, as compared to testing screens 910 and 920, the contrast level of the first color of fifth sub-region 934 has been changed to comprise a third contrast level that is lower that of the first and third sub-regions 914 and 924. Accordingly, where the third contrast level of the first color in the fifth sub-region 934 is perceived by a patient to occupy the rightward position of testing field 932, the patient may provide an appropriate input thereof by touching the touchscreen at that position, by inputting a signal via a directional-type touchpad or input device, by providing an appropriate voice indication thereof, or such input may be provided by monitoring and/or recording the patient's eye movements or gaze and the use of eye-tracking software, or by providing an appropriate hand gesture indication thereof, or such input may be provided by monitoring and/or recording the patient's hand gestures and the use of hand-gesture software. Where a patient is unable to ascertain the first color, the patient may provide a "pass"-type input by means of a touchscreen icon (not shown), by inputting a signal via a touchpad or input device, by providing a voice indication thereof, or by monitoring and/or recording the patient's eye movements or gaze.

As may be appreciated, additional testing screens may be presented and different contrast levels presented until the patient's threshold for a specific color is determined. Upon completion of a specific color phase in the testing process, testing software will continue to the next color phase for the tested eye. If all color phases have been completed for the tested eye, testing software displays an eye selection screen and continues the testing process with the next eye to be tested. If all color phases for both eyes have been completed, the test process is complete. As may be appreciated, while the above primarily describes decreasing contrast levels in the case of a correct response, one or more first color contrast levels and their positions may be randomly presented, or re-presented as needed, for example, in the case of a pass-type input, a delay in providing an input, or lack of an input. Additionally, while the above examples describe a total of four quadrants or screen positions, it should be appreciated that the subject matter is not particularly limited to a total four quadrants or four screen positions, and the number of sub-regions or positions may be higher or lower.

Figure 31A:
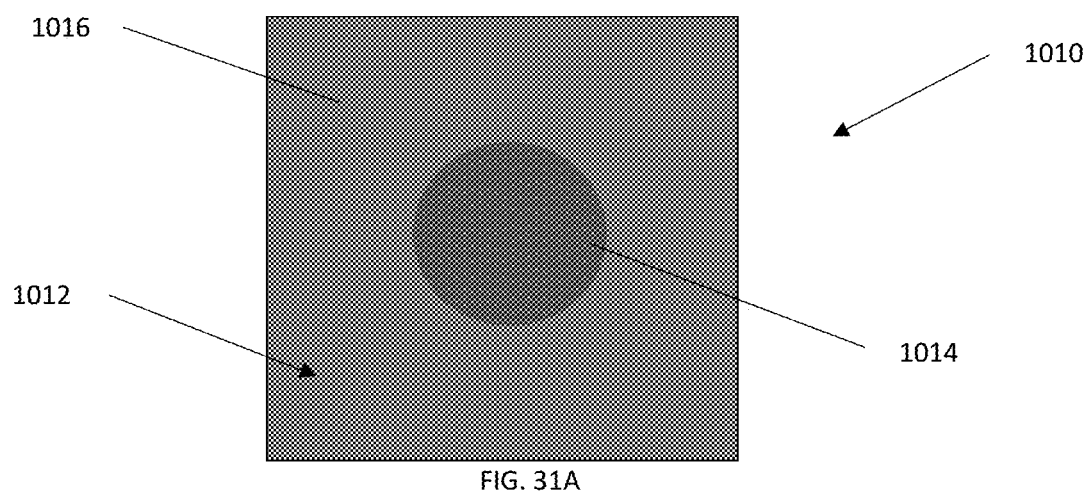
FIGS. 31A-31B schematically illustrate a so-called real-time region or area-type cone contrast color vision test; and,
FIGS. 32A and 32B schematically illustrate a region or area-type cone contrast color vision test.
Figure 31B:
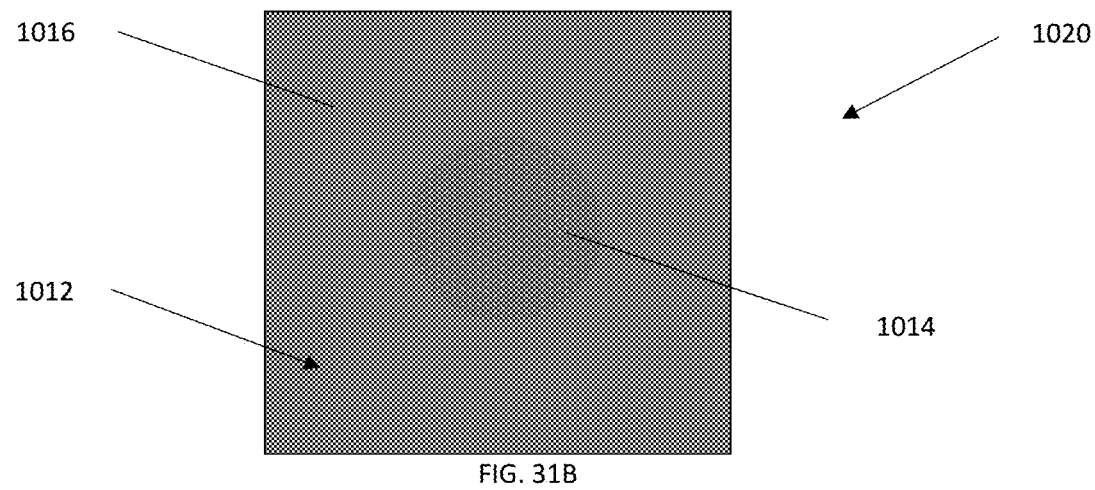

Referring now to FIGS. 31A-31B, while the previously described methodologies, e.g., "Forced Choice" type testing procedures, sine wave gratings, and spatial and temporal dithering, all describe the use of presenting a plurality of testing screens and subsequent testing screens wherein a sub-area or sub-region of a color to be tested can be deliberately or randomly presented in a different positional location on the each testing screen that is displayed, a so-called "real-time" testing screen may also be utilized. In such "real-time" testing screen, the positional location of a sub-region for which a color contrast level is to be tested can remain constant, but the contrast level of the first color at that same position can be progressively incremented or decremented in real-time, for example, to pass from being perceptible to imperceptible, or vice-versa. In such case, where a first color sub-region passes from being perceptible to imperceptible, for example, a patient may provide an appropriate input thereof by touching a touchscreen at the position, by inputting a signal via touchpad or input device, by providing an appropriate voice indication thereof, or such input may be provided by monitoring and/or recording the patient's eye movements or gaze and the use of eye-tracking software, or by providing and appropriate hand gesture indication thereof, or such input may be provided by monitoring and/or recording the patient's hand gestures and the use of hand-gesture software. Where a patient is unable to ascertain the first color, the patient may provide a "pass"-type input by means of a touchscreen icon (not shown), by inputting a signal via a touchpad or input device, by providing a voice indication thereof, by monitoring and/or recording the patient's eye movements or gaze, or by monitoring and/or recording the patient's hand gestures. In accordance with the above, as shown in FIGS. 31A and 31B, testing screen 1010 comprising testing field 1012 including a first color at a first contrast level in a first sub-region 1014 can be progressively incrementally displayed according to one or more of the previously discussed procedures, e.g., including but not limited to spatial or temporal dithering, and a second color (grey) at a first contrast level in a second sub-region 1016 may be displayed to a patient. As compared to CCT testing procedures utilizing characters requiring both color vision and visual acuity, it is seen that the testing field 1012, and first sub-region 1014 and second sub-region 1016 thereof, are configured to encompass a large, or substantial, portion of the testing screen 1010 such that patients with low visual acuity and/or individuals performing testing on smaller devices, such as smart phones, may readily perceive sub-regions 1014 and 1016. In accordance therewith, a first color for which color contrast level is to be tested (red, green or blue) can be progressively presented at, for example, a central position of testing field 1012 and the second color (grey) presented at the remaining portions of the testing field 1012. As may be appreciated from FIGS. 31A and 31B, the color contrast level of first sub-region 1014 is shown as being progressively desaturated from the higher contrast level shown in FIG. 31A to the lower contrast shown in FIG. 31B. While not shown, during such procedure, for example, as the contrast level of first region 1014 is progressively decreased, it passes from being perceptible to being imperceptible, wherein at such point a patient may provide an appropriate input to acknowledge that the first region 1014 is no longer perceptible. Of course, other previously discussed inputs may also be utilized.

Figure 32A:
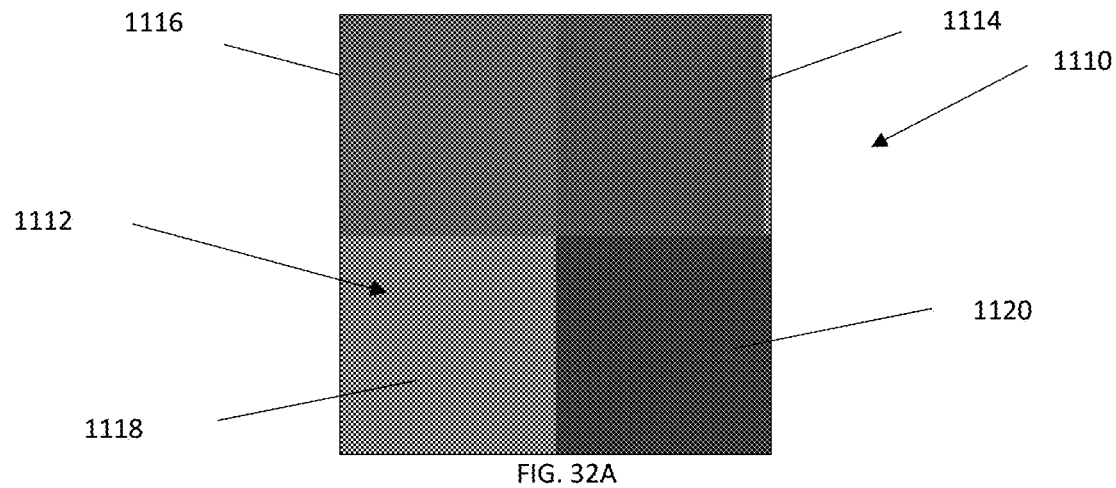
Figure 32B:
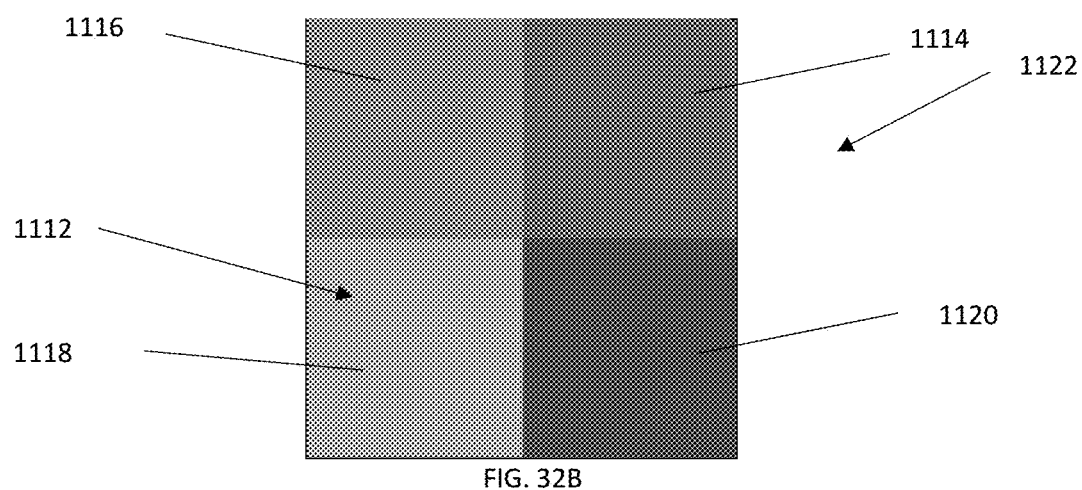

FIGS. 32A-32B illustrate an example of another color contrast level testing procedure, wherein, for example, cone-isolating color contrast levels may be presented in multiple quadrants at a time. In such tests, each quadrant can display a different color contrast level of a color and a patient identifies which of the lowest contrast levels are perceptible. This type of test is believed to significantly speed up the testing process as the patient can identify the lowest contrast quadrant that is perceptible without having to navigate through a plurality of screens. The test typically proceeds at or around the patient's lowest contrast level with repetitive presentations of either multiple quadrants or single presentations. In most cases, the color presented in each quadrant can be the same, however, to increase the confidence of the response, one or more of the quadrants may be a background color (grey). If the patient selects a quadrant corresponding to the background color, the test can re-present the same color contrast levels for the color being tested in a randomized fashion before proceeding to the next phase of testing, i.e., presenting a subsequent screen with quadrants or regions of a differing contrast. Where a patient is unable to perceive any of the quadrants or regions, the pass options discussed relative to the previously discussed tests would be available. As shown in FIG. 32A, for example, during such test, a first testing screen 1100 comprising a testing field 1112 including first sub-region 1114, second sub-region 1116, third sub-region 1118, and fourth sub-region 1118 may be presented to a patient. As compared to CCT testing procedures utilizing characters requiring visual acuity, it is seen that the testing field 1112, and first through fourth sub-regions 1114-1120, are configured to encompass a large or substantial portion of the testing screen 1110 such that patients with low visual acuity and/or individuals performing testing on smaller devices, such as smart phones, may readily perceive sub-regions several sub-regions. In accordance therewith, testing field 1112 is shown as utilizing a quadrant-type system wherein a first color for which color contrast level is to be tested (red, green or blue) is deliberately or randomly presented at varying contrast levels in each of the four quadrants. A second color (grey) may, optionally, be presented in one of the four quadrants of the testing field 1112. As shown in FIG. 32A, the contrast levels of each of sub-regions one through four vary relative to one another with sub-region 1120 having the highest contrast and sub-region 1118 having the lowest contrast thereof. Hence, where the lowest contrast level of the first color in sub-region 1118 is perceived by a patient to occupy the lower left quadrant of testing field 1118, the patient may provide an appropriate input thereof by touching the touchscreen at that position, by inputting a signal via a directional-type touchpad or input device, by providing an appropriate voice indication thereof to a computer executing voice recognition software, or such input may be provided by monitoring and/or recording the patient's eye movements or gaze, which is input to the computer executing eye-tracking software. Where a patient is unable to ascertain the first color presented, a patient may provide a "pass"-type input by means of a touchscreen icon (not shown), by inputting a signal via a directional-type touchpad or input device, by providing a voice indication thereof, or by monitoring and/or recording the patient's eye movements or gaze. Based on the patient's correct or incorrect response, the color contrast level of the first color can be decreased or increased as appropriate and a new or refreshed testing screen presented.

As shown in FIG. 32B, where a correct response is input by the patient or measured at testing screen 1110, a new screen may be presented or refreshed such that testing screen 1122 is displayed. As may be appreciated, testing screen 1122 is similar to testing screen 1110 in that it also comprises a quadrant-type system wherein the first color for which color contrast level is being tested (red, green or blue) is deliberately or randomly presented at different contrast levels in the four quadrants. A second color (grey) may, optionally, be presented in one of the four quadrants of the testing field 1112. However, as compared to testing screen 1110, the contrast level of sub-regions one through four have been modified and/or rearranged relative to screen 1110, and the contrast of the sub-regions of screen 1122 vary relative to one another with sub-region 1120 having the highest contrast and sub-region 1118 having the lowest contrast thereof. Hence, where the lowest contrast level of the first color in sub-region 1118 is perceived by a patient to occupy the lower left quadrant of testing field 1118, the patient may provide an appropriate input thereof by touching the touchscreen at that position, by inputting a signal via a directional-type touchpad or input device, by providing an appropriate voice indication thereof to a computer executing voice recognition software, or such input may be provided by monitoring and/or recording the patient's eye movements or gaze, which is input to the computer executing eye-tracking software. Where a patient is unable to ascertain the first color presented, a patient may provide a "pass"-type input by means of a touchscreen icon (not shown), by inputting a signal via a directional-type touchpad or input device, by providing a voice indication thereof, or by monitoring and/or recording the patient's eye movements or gaze. Based on the patient's correct or incorrect response, the color contrast level of the first color can be decreased or increased as appropriate and a new or refreshed testing screen presented.

As may be appreciated, different contrast levels are progressively presented until the patient's threshold for a specific color is determined. Upon completion of a specific color phase in the testing process, testing software will continue to the next color phase for the tested eye. If all color phases have been completed for the tested eye, testing software displays an eye selection screen and continue the testing process with the next eye to be tested. If all color phases for both eyes have been completed, the test process is complete.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A method for administering a cone contrast color vision test to a patient using a computer, comprising the steps of:
    (a) simultaneously displaying a first color at a first contrast level in a first region of a display and a second color at a first contrast level in a second region of the display, which display is in communication with the computer;
    (b) receiving a first input signal from the patient via an input device in communication with the computer, where the first input signal is indicative of whether the patient recognizes the first color displayed in the first region at the first contrast level;
    (c) displaying the first color at a second contrast level in a third region of the display and the second color at a second contrast level in a fourth region of the display, where the second contrast level of the first color is not equivalent to the first contrast level of the first color;
    (d) receiving a second input signal from the patient via the input device, where the second input signal is indicative of whether the patient recognizes the first color displayed in the third region at the second contrast level;
    (e) assigning a score to the first and second input signals, the score related to a cone sensitivity of the patient to the first color at the first and second contrast levels;
    (f) storing the score in a storage device;
    (g) comparing the score to at least one previous score associated with the patient to calculate a progression of a cone sensitivity loss in the patient; and,
    (h) displaying a graphical representation of the progression of the cone sensitivity loss in the patient.

2. The method recited in claim 1, wherein the first color comprises one of red, green, or blue cone-isolating colors, and the second color is grey.

3. The method recited in claim 2, wherein the second contrast level of the first color differs from the first contrast level of the first color.

4. The method recited in claim 3, wherein
when the first and second region are simultaneously displayed, the first region does not simultaneously occupy the second region; and,
when the third and fourth region are simultaneously displayed, the third region does not simultaneously occupy the fourth region.

5. The method recited in claim 4, wherein the first and third regions are displayed in one of an upper, leftward, rightward, or lower region of the display and a position of the first and third regions are randomly selected.

6. The method recited in claim 4, the first and third regions are displayed in a quadrant of the display and the quadrant of the first and third regions is randomly selected.

7. The method recited in claim 1, wherein the first and second input signals comprise at least one of a touch input, a voice input, an eye tracking input, or a hand gesture input, the input device is in communication with the computer.

8. The method recited in claim 1, wherein at least one of the first and second contrast levels is set to a predetermined default value if there are no prior cone contrast color vision test records associated with the patient.

9. The method recited in claim 8, wherein steps (a) through (f) are repeated sequentially using values for the first and second contrast levels based on the patient's cone contrast threshold level in a prior iteration of the cone contrast color vision test to determine a lowest cone sensitivity of the patient.

10. The method recited in claim 2, wherein the first and second contrast levels of the first and third regions are provided by:
modifying saturation of the first color,
spatial dithering, or
temporal dithering.

11. The method recited in claim 2, wherein the first and third regions comprise a sine wave grating pattern formed from the first color presented between the first and second color saturation or intensity level, where the color saturation is increased or decreased based on the patient response until the patient reaches his contrast sensitivity threshold of the linear or concentric circle sinusoidal gratings.

12. The method recited in claim 11, wherein the sine wave grating pattern is formed by varying the spatial frequency of the gratings formed from the first color presented between the first and second color saturation or intensity level, where the color saturation is increased or decreased based on the patient response until the patient reaches his contrast sensitivity threshold of the linear or concentric circle sinusoidal gratings.

13. The method recited in claim 12, wherein the first and third regions are disposed in one of an upper, leftward, rightward, or lower region of the display and a position of the first and third regions is randomly selected.

14. The method recited in claim 12, wherein the first and third regions are disposed in a quadrant of the display and the quadrant of the first and third regions is randomly selected.

15. The method recited in claim 1, wherein the first contrast level of the second color is the same as the second contrast level of the second color.

16. The method recited in claim 1, wherein the first contrast level of the second color is different from the second contrast level of the second color.

17. A method for administering a cone contrast color vision test to a patient using a computer, comprising the steps of:
(a) displaying a first display screen simultaneously displaying at least a first color and a second color in at least two regions of the display, the first color being displayed at a first contrast level and the second color being displayed at a second contrast level, the display screen being in communication with the computer;
(b) receiving an input signal from the patient via an input device in communication with the computer, where the input signal is indicative of whether the patient recognizes one or more of the first and second color;
(c) displaying a second display screen simultaneously displaying at least the first color and the second color in the at least two regions at third and a fourth contrast levels, respectively; and
(d) receiving a second input signal from the patient via the input device, where the second input signal is indicative of whether the patient recognizes the one or more of the first and second color;
(e) assigning a score to the first and second input signals, the score related to a cone sensitivity of the patient to the first and second colors;
(f) storing the score in a storage device;
(g) comparing the score to at least one previous score associated with the patient to calculate a progression of a cone sensitivity loss in the patient; and,
(h) displaying a graphical representation of the progression of the cone sensitivity loss in the patient.

18. The method recited in claim 17, wherein the first and second color are the same.

19. The method of claim 17, wherein at least one of the first and second color are different.

20. The method of claim 19, wherein the at least one of the second color is grey.

* * * * *